US011033539B2

(12) United States Patent
Harriott et al.

(10) Patent No.: US 11,033,539 B2
(45) Date of Patent: Jun. 15, 2021

(54) COMPOUNDS OF FORMULAS (VII), (VIII), (IX), (XI), (XII), (XIII), AND (XIV) AS MUSCARINIC RECEPTOR 4(M4) ANTAGONISTS FOR TREATING NEUROLOGICAL DISEASES

(71) Applicant: Neurocrine Biosciences, Inc., San Diego, CA (US)

(72) Inventors: Nicole Harriott, San Diego, CA (US); Nicholas Pagano, San Diego, CA (US)

(73) Assignee: Neurocrine Biosciences, Inc., San Diego, CA (US)

( * ) Notice: Subject to any disclaimer, the term of this patent is extended or adjusted under 35 U.S.C. 154(b) by 260 days.

(21) Appl. No.: 15/773,915

(22) PCT Filed: Nov. 4, 2016

(86) PCT No.: PCT/US2016/060659
§ 371 (c)(1),
(2) Date: May 4, 2018

(87) PCT Pub. No.: WO2017/079641
PCT Pub. Date: May 11, 2017

(65) Prior Publication Data
US 2018/0325887 A1 Nov. 15, 2018

Related U.S. Application Data

(60) Provisional application No. 62/275,708, filed on Jan. 6, 2016, provisional application No. 62/252,179, filed on Nov. 6, 2015.

(51) Int. Cl.
| *A61K 31/445* | (2006.01) |
| *C07D 211/14* | (2006.01) |
| *A61K 31/4545* | (2006.01) |
| *C07D 401/12* | (2006.01) |
| *C07D 211/40* | (2006.01) |
| *C07D 211/26* | (2006.01) |
| *A61P 25/28* | (2006.01) |
| *A61P 25/18* | (2006.01) |
| *A61P 25/16* | (2006.01) |
| *A61K 31/444* | (2006.01) |
| *A61K 31/496* | (2006.01) |
| *A61K 31/506* | (2006.01) |
| *A61K 31/519* | (2006.01) |

(52) U.S. Cl.
CPC ........ *A61K 31/4545* (2013.01); *A61K 31/444* (2013.01); *A61K 31/496* (2013.01); *A61K 31/506* (2013.01); *A61K 31/519* (2013.01); *A61P 25/16* (2018.01); *A61P 25/18* (2018.01); *A61P 25/28* (2018.01); *C07D 211/26* (2013.01); *C07D 211/40* (2013.01); *C07D 401/12* (2013.01)

(58) Field of Classification Search
CPC .. C07D 403/12; C07D 403/14; C07D 401/12; C07D 401/14; C07D 211/14; A61K 31/445
USPC .......................................... 514/317; 546/192
See application file for complete search history.

(56) References Cited

U.S. PATENT DOCUMENTS

| 6,410,566 B1 * | 6/2002 | Shiota | C07D 333/20 514/318 |
| 6,451,842 B1 * | 9/2002 | Shiota | C07D 209/42 514/422 |
| 7,390,830 B1 * | 6/2008 | Shiota | A61K 31/5377 514/426 |
| 2007/0249701 A1 * | 10/2007 | Shiota | C07D 207/09 514/408 |

(Continued)

FOREIGN PATENT DOCUMENTS

| EP | 0 718 287 A2 | 6/1996 |
| EP | 1724262 | 11/2006 |

(Continued)

OTHER PUBLICATIONS

CAS Index of RN 1081119-58-5 (2008) (Year: 2008).*

(Continued)

*Primary Examiner* — Douglas M Willis
(74) *Attorney, Agent, or Firm* — Fish & Richardson P.C.

(57) ABSTRACT

Provided herein are small molecule compounds of the following formula (I): or a stereoisomer, tautomer, solvate, ester or pharmaceutically acceptable salt thereof, wherein A, B, C, $L_1$, $L_2$, $R_2$, $R_3$, $R_4$, $R_5$, w, x, y and z are as defined herein. Methods for treating diseases/disorders by antagonizing muscarinic receptors, including specifically antagonizing muscarinic receptor 4 (M4), are also disclosed. Such diseases/disorders are e.g. neurological diseases/disorders such as e.g. Alzheimer's Disease, Lewy Body Dementia and the cognitive deficits associated with schizophrenia, Parkinson's Disease, drug induced Parkinsonism, dyskinesias, dystonia, chorea, levodopa induced dyskinesia, cerebral palsy, progressive supranuclear palsy, and Huntington's disease. Preferred compounds are e.g. N-[2-(1-benzylpiperidin-4-yl)ethyl]-4-(pyrazin-2-yl)-piperazine-1-carboxamide derivatives and related compounds wherein the pyrazine has been replaced by e.g. pyridazine, pyrimidine, pyridine or phenyl.

17 Claims, No Drawings

(56) References Cited

U.S. PATENT DOCUMENTS

2010/0292214 A1* 11/2010 Deligny .............. C07D 417/14
            514/214.02
2015/0266825 A1   9/2015 Hood et al.

FOREIGN PATENT DOCUMENTS

| JP | 2006511554 | | 4/2006 |
|---|---|---|---|
| WO | WO 01/21590 | | 3/2001 |
| WO | 03/062234 A1 | | 7/2003 |
| WO | 2007/075629 A2 | | 7/2007 |
| WO | 2007/130383 A2 | | 11/2007 |
| WO | 2008/130570 A1 | | 10/2008 |
| WO | 2011/059048 A1 | | 5/2011 |
| WO | WO 2013/076090 | | 5/2013 |
| WO | 2014/074517 A1 | | 5/2014 |
| WO | 2014/079787 A1 | | 5/2014 |
| WO | 2014/147611 A1 | | 9/2014 |
| WO | 2014/163161 A1 | | 10/2014 |
| WO | 2015/036759 A1 | | 3/2015 |
| WO | WO 17/079641 | * | 5/2017 |

OTHER PUBLICATIONS

CAS Index of RNs 929865-73-6 and 921056-21-5 (2007) (Year: 2007).*
Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Vippagunta, et al. Advanced Drug Delivery Reviews, 48, 2001, 18.*
Singapore Search Report in Singapore Appln. No. 11201803757U, dated Jul. 18, 2019, 4 pages.
[No Author Listed], "Editor's Note Regarding 'Mechanism of Corticotropin-Releasing Factor Type 1 Receptor Regulation by Nonpeptide Antagonists'" Mol. Pharmacol., 2005, 68(1):260.
Bundgard, "Design of Prodrugs," 1985, pp. 7-9, 21-24.
Constantino et al., "Modeling of Poly (ADP-ribose) Polymerase (PARP) inhibitors. Docking of Ligands and Quantitative Structure—Activity Relationship Analysis," Journal of Medicinal Chemistry, 2001, 44(23):3786-3794.
Erosa-Rivero et al., "The potency and efficacy of anticholinergics to inhibit haloperidol-induced catalepsy in rats correlates with their rank order of affinities for the muscarinic receptor subtypes," Neuropharmacology, 2014, 81:176-87.
Forest, "Recent advances in the diagnosis and management of congenital adrenal hyperplasia due to 21-hydroxylase deficiency," Human Reproduction Update, 2004, 10(6):469-485.
Higuchi T. et al., "Pro-drugs as Novel Delivery Systems," A.C.S. Symposium Series, vol. 14.
Hoare et al., "Mechanism of Corticotropin-Releasing Factor Type 1 Receptor Regulation by Nonpeptide Antagonists," Mol. Pharmacol. 2003 63(3):751-65.
Merke et al., "Future directions in the study and management of congenital adrenal hyperplasia due to 21-hydroxylase deficiency," Ann Intern Med, 2002, 136:320-334.
Merke et al., "New Ideas for Medical Treatment of Congenital Adrenal Hyperplasia," Endocrinology and Metabolism Clinics of North America, Mar. 2001, 30(1):121-35.
Riffell et al., "Tankyrase-targeted therapeutics: expanding opportunities in PARP family," Nature Reviews Drug Discovery, 2012, 11(12):923-936.
Croy et al., "Characterization of PCS1055, a Novel Muscarinic M4 Receptor Antagonist," European Journal of Pharmacology, Jul. 5, 2016, 782:70-6.
International Search Report and Written Opinion in International Application No. PCT/US2016/006059, dated Dec. 16, 2016, 15 pages.
International Preliminary Report on Patentability in International Application No. PCT/US2016/060659, dated May 8, 2018, 8 pages.
RN 1216662-47-3 Registry,Database Registry [Online] Retrieved from STN, Apr. 4, 2010, Date of Retrieval: Sep. 23, 2020.
RN 1277586-37-4 Registry,Database Registry [Online] Retrieved from STN, Apr. 10, 2011, Date of Retrieval: Sep. 23, 2020.
RN 1302253-24-2 Registry,Database Registry [Online] Retrieved from STN, May 29, 2011, Date of Retrieval: Sep. 23, 2020.
RN 1322465-14-4 Registry,Database Registry [Online] Retrieved from STN, Aug. 24, 2011, Date of Retrieval: Sep. 23, 2020.
RN 1322465-36-0 Registry,Database Registry [Online] Retrieved from STN, Aug. 24, 2011, Date of Retrieval: Sep. 23, 2020.
RN 1648258-27-8 Registry,Database Registry [Online] Retrieved from STN, Feb. 16, 2015, Date of Retrieval: Sep. 23, 2020.
RN 929865-73-6 Registry,Database Registry [Online] Retrieved from STN, Apr. 13, 2007, Date of Retrieval: Aug. 6, 2020.
Scarr, "Muscarinic receptors: their roles in disorders of the central nervous system and potential therapeutic targets," CNS Neuroscience & Therapeutics, 2012, 18:369-379.

* cited by examiner

COMPOUNDS OF FORMULAS (VII), (VIII), (IX), (XI), (XII), (XIII), AND (XIV) AS MUSCARINIC RECEPTOR 4(M4) ANTAGONISTS FOR TREATING NEUROLOGICAL DISEASES

BACKGROUND

Technical Field

Compounds are provided herein that selectively antagonize muscarinic receptors, in particular muscarinic receptor 4 (M4), as well as methods for treating diseases and/or disorders that would benefit from the same.

Description of the Related Art

Muscarinic acetylcholine receptors are autonomic receptors that form G protein-receptor complexes in the cell membranes of certain neurons and other cell types (e.g., endothelial cells of blood vessels). Muscarinic receptors are located postsynaptically at the parasympathetic neuroeffector junction, from where the receptors function to increase or decrease the activity of the effector cells. Extrapyramidal symptoms are observed in patients treated with antipsychotic therapeutics and in patients who have neuroleptic malignant syndrome, brain damage (e.g., athetotic cerebral palsy), encephalitis, and meningitis. Drugs other than antipsychotics also cause extrapyramidal symptoms, for example antidopaminergic drugs (e.g., the antiemetic metoclopramide and the antidepressant amoxapine) and selective serotonin reuptake inhibitors (SSR*), which indirectly decrease dopamine. Conditions associated with extrapyramidal symptoms include acute dystonic reactions, akathisia, pseudoparkinsonism, and tardive dyskinesia. Extrapyramidal symptoms caused by antipsychotic therapeutics are being treated with anticholinergic drugs that lack selectivity for any of the five muscarinic receptor subtypes (see, e.g., Erosa-Rivero et al., *Neuropharmacology* 81:176-87 (2014)). Because anticholinergic drugs that effect multiple muscarinic receptors may cause distinct and in certain instances opposing effects, therapeutics that exhibit selectivity for particular receptors are desired.

BRIEF SUMMARY

Provided herein are compounds that antagonize muscarinic receptors. In particular embodiments, compounds are provided that selectively antagonize muscarinic receptor 4 (M4). Such compounds are useful in the treatment of a number of diseases and/or disorders, particularly neurological conditions, diseases, and disorders including cognitive disorders such as Alzheimer's Disease, Lewy Body Dementia and the cognitive deficits associated with schizophrenia. In other embodiments, methods are provided for treating or preventing movement disorders which may include Parkinson's Disease, drug induced Parkinsonism, dyskinesias, dystonia, chorea, levodopa induced dyskinesia, cerebral palsy and progressive supranuclear palsy, and Huntington's disease, particularly chorea associate with Huntington's disease.

In one embodiment, compounds are provided having the structure of formula (I):

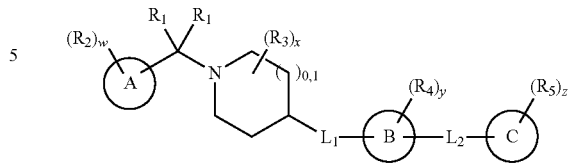

or a stereoisomer, tautomer, solvate, ester, prodrug, or pharmaceutically acceptable salt thereof, wherein A, B, C, $L_1$, $L_2$, $R_1$, $R_2$, $R_3$, $R_4$, $R_5$, w, x, y and z are as defined below. More specific embodiments are also described within Tables 1-14, as well as the more specific formulas noted herein below.

In another embodiment, pharmaceutical compositions are provided comprising a compound of formula (I), including one or more of the specific compounds described herein, and at least one pharmaceutically acceptable excipient. The compounds, as well as the pharmaceutical compositions comprising the compounds, may be used for antagonizing a muscarinic receptor, such as muscarinic receptor 4 (M4). In certain embodiments, the compound is a selective M4 antagonist.

These and other embodiments will be apparent upon reference to the following detailed description. To this end, various references are set forth herein that describe in more detail certain background information, procedures, compounds and compositions, and are each hereby incorporated by reference in their entirety.

DETAILED DESCRIPTION

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising," are to be construed in an open, inclusive sense, that is, as "including, but not limited to." In addition, the term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features. Headings provided herein are for convenience only and do not interpret the scope or meaning of the claimed embodiments.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Also, as used in this specification and the appended claims, the singular forms "a," "an," and "the" include plural referents unless the content clearly dictates otherwise. Thus, for example, reference to "a non-human animal" may refer to one or more non-human animals, or a plurality of such animals, and reference to "a cell" or "the cell" includes reference to one or more cells and equivalents thereof (e.g., plurality of cells) known to those skilled in the art, and so forth. When steps of a method are described or claimed, and the steps are described as occurring in a particular order, the description of a first step occurring (or being performed) "prior to" (i.e., before) a second step has the same meaning if rewritten to state that the second step occurs (or is performed) "subsequent" to the first step. The term "about" when referring to a number or a numerical range means that the number or numerical range referred to is an approximation within experimental variability (or within statistical experimental error), and thus the number or numerical range may vary between 1% and 15% of the stated number or numerical range. It should also be noted that the term "or" is generally employed in its sense including "and/or" unless the content clearly dictates otherwise. The term, "at least one," for example, when referring to at least one compound or to at least one composition, has the same meaning and understanding as the term, "one or more."

Provided herein are compounds useful for treating diseases and/or disorders treatable by antagonizing one or more muscarinic receptors. In particular embodiments, compounds are provided that are selective for muscarinic receptor 4 (M4) (also referred herein as the M4 receptor).

Provided herein are compounds having a structure of the following formula (I):

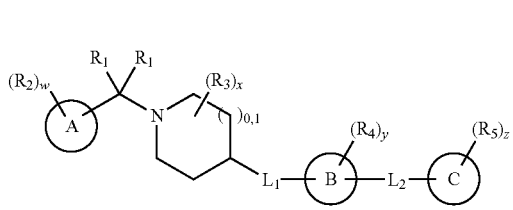
(I)

or a stereoisomer, tautomer, solvate, ester, prodrug, or pharmaceutically acceptable salt thereof, wherein:
  A, B and C are each independently a carbocycle or heterocycle;
  $R_1$ is, at each occurrence, H, $C_{1-4}$alkyl, C(=O)O$C_{1-4}$alkyl or aryl;
  $R_2$, $R_3$, $R_4$ and $R_5$ are each independently —OH, —NH$_2$, —NH($C_{1-4}$alkyl), —N($C_{1-4}$alkyl)$_2$, —C≡N(=O)NH$_2$, halo, $C_{1-4}$alkylOH, $C_{1-4}$haloalkyl, $C_{1-4}$alkoxy or $C_{1-4}$haloalkoxy;
  w, x, y and z are each independently 0, 1, 2 or 3;
  $L_1$ is a heteroalkylene linker having at least one N, O or S heteroatom, and wherein the heteroalkylene may be a straight chain or cyclized and optionally substituted with oxo, —OH, $C_{1-4}$alkyl or $C_{1-4}$alkoxy; and
  $L_2$ is an optional linker that is not present or, when present, is —O(CH$_2$)$_m$- where m is 0 or 1.
In one embodiment of formula (I), $R_1$ is H at both occurrences.
In one embodiment of formula (I), one $R_1$ is H and the other $R_1$ is methyl.
In one embodiment of formula (I), $R_1$ is methyl at both occurrences.
In one embodiment of formula (I), A is a non-aromatic carbocycle, and more specifically cyclohexyl.

In one embodiment of formula (I), A is an aromatic carbocycle, and more specifically aryl.
In one embodiment of formula (I), A is phenyl or naphthyl.
In one embodiment of formula (I), A is phenyl.
In one embodiment of formula (I), A is an aromatic heterocycle, and more specifically one of the following:

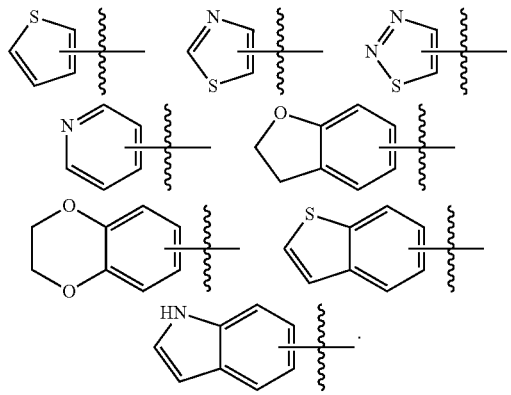

In one embodiment of formula (I), w is 0 and $R_2$ is not present.
In one embodiment of formula (I), w is 1, 2 or 3, and $R_2$ is at each occurrence —OH, —C≡N, halo, or $C_{1-4}$alkyl.
In one embodiment, compounds are provided of formula (I) wherein —A(R$_2$)$_w$ is:

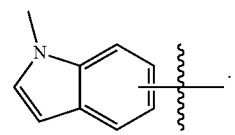

In one embodiment of formula (I), x is 0 and $R_3$ is not present.
In one embodiment of formula (I), x is 1 or 2 and $R_3$ is at each occurrence —OH or $C_{1-4}$alkyl-OH.
In one embodiment of formula (I), $L_1$ is a a heteroalkylene linker having at least one N or O heteroatom, and wherein the heteroalkylene may be a straight chain or cyclized and optionally substituted with oxo, —OH, $C_{1-4}$Alkyl or $C_{1-4}$alkoxy, and more specifically one of the following:

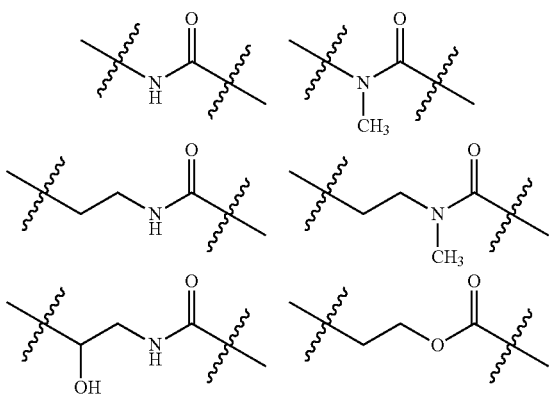

-continued

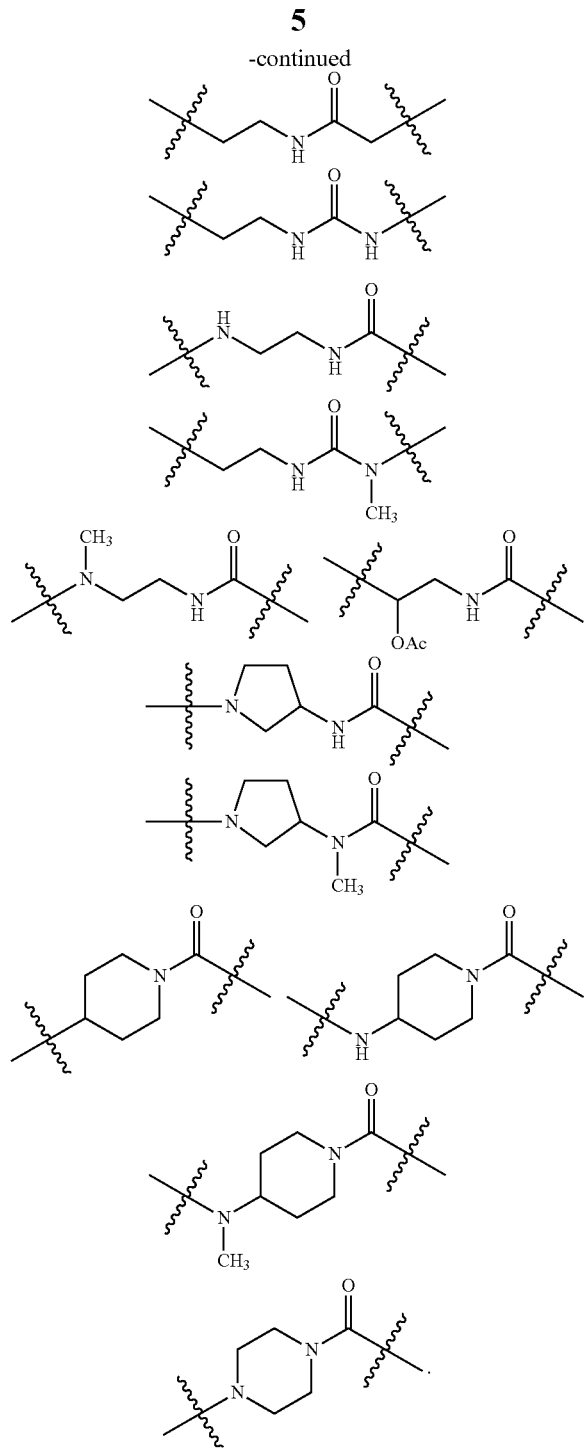

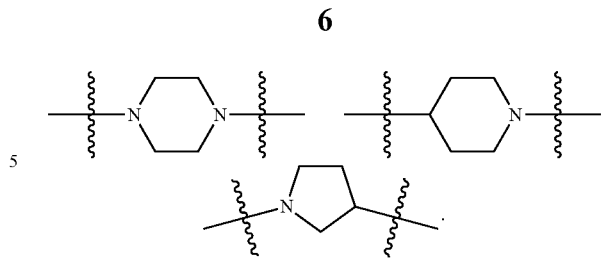

In one embodiment of formula (I), B an aromatic heterocycle, and more specifically

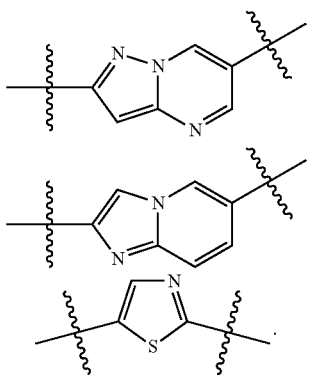

In one embodiment of formula (I), y is 0 and $R_4$ is not present.

In one embodiment of formula (I), y is 1 and $R_4$ is methyl.

In one embodiment of formula (I), B is piperazinyl, y is 1 and $R_4$ is methyl and, in a more specific embodiment, such moiety has the following structure:

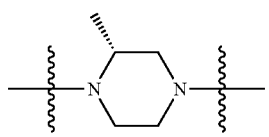 [SMILES: *N1CCN(*)[C@H](C)C1]

In one embodiment of formula (I), y is 2 and $R_4$ at both occurences is methyl.

In one embodiment of formula (I), B is piperazinyl, y is 2 and $R_4$ at both occurences is methyl and, in a more specific embodiment, such moiety has one of the following structures:

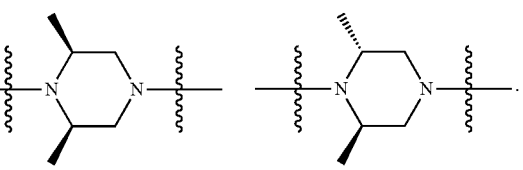

In one embodiment of formula (I), $L_2$ is not present.
In one embodiment of formula (I), $L_2$ is —O—
In one embodiment of formula (I), $L_2$ is —OCH$_2$—.
In one embodiment of formula (I), C is an aromatic 5-12 membered carbocycle or heterocycle.
In one embodiment of formula (I), C is an aromatic carbocycle, and more specifically aryl.

In one embodiment of formula (I), B is a non-aromatic carbocyle, and more specifically cyclohexyl.

In one embodiment of formula (I), B is an aromatic carbocyle, and more specifically aryl.

In one embodiment of formula (I), B is phenyl or naphthyl.

In one embodiment of formula (I), B is phenyl.

In one embodiment of formula (I), B is a non-aromatic heterocycle.

In one embodiment of formula (I), B is piperazinyl, piperadinyl or pyrrolidinyl, and more specifically one of the following:

In one embodiment of formula (I), C is phenyl.

In one embodiment of formula (I), C is an aromatic heterocycle, and more specifically one of the following:

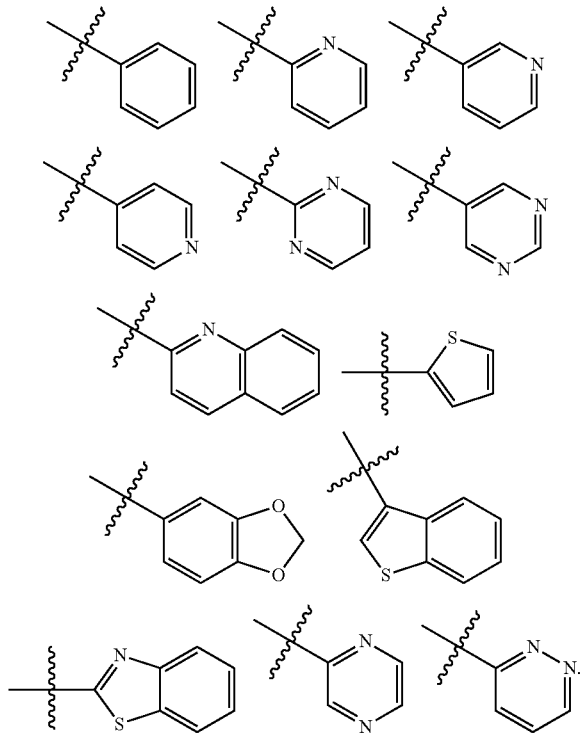

In one embodiment of formula (I), z is 0 and $R_5$ is not present.

In one embodiment of formula (I), z is 1, 2 or 3, and each occurrence of $R_5$ is independently -OH, $-NH_2$, $-NH(C_{1-4}alkyl)$, $-N(C_{1-4}alkyl)_2$, $-C\equiv N$, halo, $C_{1-4}alkyl$, $C_{1-4}alkyl$-OH, $C_{1-4}haloalkyl$, $C_{1-4}alkoxy$ or $C_{1-4}haloalkoxy$.

In one embodiment of formula (I), compounds are provided having a structure of the following formula (II) or (III):

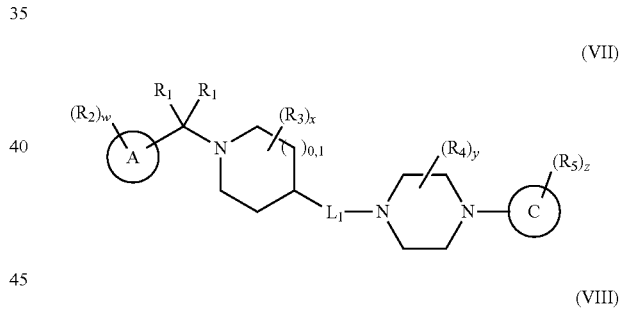

In one embodiment of formula (I), compounds are provided having a structure of the following formula (IV) or (V):

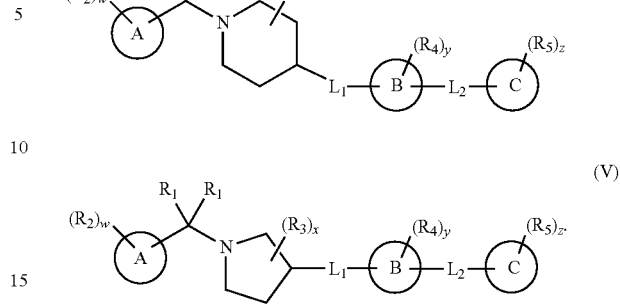

In one embodiment of formula (I), compounds are provided having a structure of the following formula (VI):

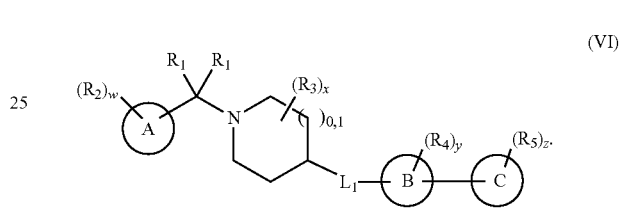

In one embodiment of formula (I), compounds are provided having a structure of the following formula (VII), (VIII) or (IX):

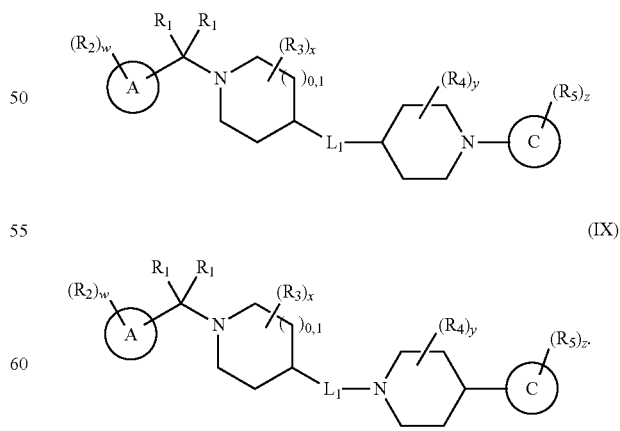

In one embodiment of formula (I), compounds are provided having a structure of the following formula (X) or (XI):

(X)

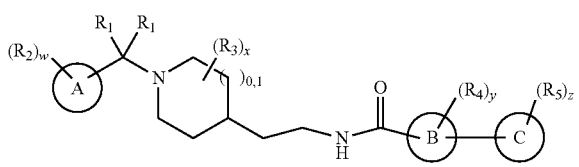

(XI)

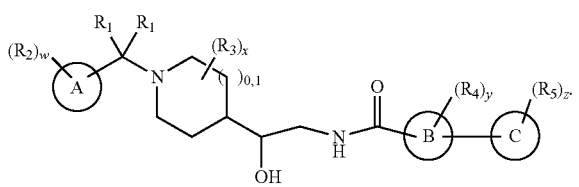

In one embodiment of formula (I), compounds are provided having a structure of the following formula (XII), (XIII) or (XIV):

(XII)

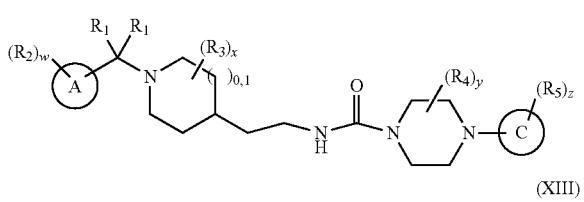

(XIII)

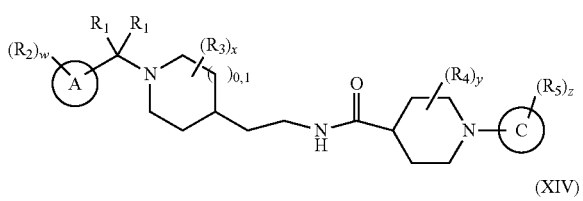

(XIV)

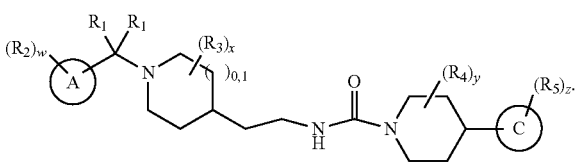

In one embodiment of formula (I), compounds are provided having a structure of the following formula (XV), (XVI) or (XVII):

(XV)

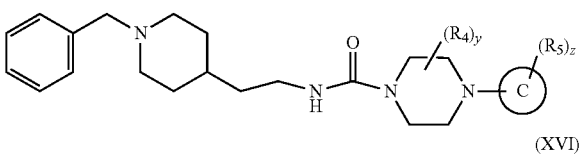

(XVI)

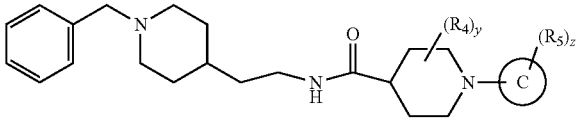

(XVII)

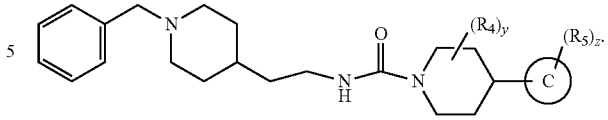

In one embodiment, compounds are provided of formula (XV), (XVI) or (XVII) wherein y is 0.

In one embodiment, compounds are provided of formula (XV), (XVI) or (XVII) wherein y is 1 or 2, and $R_4$ is at each occurrence $C_{1-4}$alkyl.

In one embodiment, compounds are provided of formula (XV), (XVI) or (XVII) wherein y is 1 or 2, and $R_4$ is at each occurrence methyl.

In one embodiment, compounds are provided of formula (XV), (XVI) or (XVII) wherein —C($R_5$)$_z$ is one of the following:

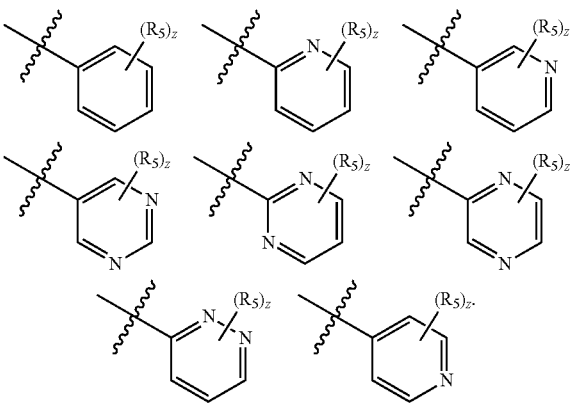

In one embodiment of the —C($R_5$)$_z$ groups noted immediately above, z is 0 and $R_5$ is not present.

In one embodiment of the —C($R_5$)$_z$ groups noted immediately above, z is 1, 2 or 3, and each occurrence of $R_5$ is independently -OH, —NH$_2$, —NH($C_{1-4}$alkyl), —N($C_{1-4}$alkyl)$_2$, —C≡N, halo, $C_{1-4}$alkyl, $C_{1-4}$alkyl-OH, $C_{1-4}$haloalkyl, $C_{1-4}$alkoxy or $C_{1-4}$haloalkoxy.

In one embodiment, a compound of formula (I) is one or more of the following compounds (with cal. ion m/z listed in parentheses):

(2R,6R)—N-[2-(1-benzylpiperidin-4-yl)ethyl]-4-(5-cyanopyrazin-2-yl)-2,6-dimethylpiperazine-1-carboxamide (462.3);

(2R,6R)—N-[2-(1-benzylpiperidin-4-yl)ethyl]-4-(6-cyanopyridazin-3-yl)-2,6-dimethylpiperazine-1-carboxamide (462.3);

(2R,6R)—N-[2-(1-benzylpiperidin-4-yl)ethyl]-4-(2-cyanopyrimidin-5-yl)-2,6-dimethylpiperazine-1-carboxamide (462.3);

(2R,6R)—N-[2-(1-benzylpiperidin-4-yl)ethyl]-4-(4-cyanophenyl)-2,6-dimethylpiperazine-1-carboxamide (460.3);

(2R,6R)—N-[2-(1-benzylpiperidin-4-yl)ethyl]-4-(5-cyanopyridin-2-yl)-2,6-dimethylpiperazine-1-carboxamide (461.3);

(2R,6R)—N-[2-(1-benzylpiperidin-4-yl)ethyl]-4-(5-cyano-4-methoxypyrimidin-2-yl)-2,6-dimethylpiperazine-1-carboxamide (492.3);

(2R,6R)—N-[2-(1-benzylpiperidin-4-yl)ethyl]-4-(5-chloropyrimidin-2-yl)-2,6-dimethylpiperazine-1-carboxamide (471.3);

(2R,6R)—N-[2-(1-benzylpiperidin-4-yl)ethyl]-4-(5-chloropyrazin-2-yl)-2,6-dimethylpiperazine-1-carboxamide (471.3);

(2R,6R)—N-[2-(1-benzylpiperidin-4-yl)ethyl]-4-(6-chloropyridazin-3-yl)-2,6-dimethylpiperazine-1-carboxamide (471.3);

(2R,6R)-4-(4-amino-5-chloropyrimidin-2-yl)-N-[2-(1-benzylpiperidin-4-yl)ethyl]-2,6-dimethylpiperazine-1-carboxamide (486.3);

(2R,6R)—N-[2-(1-benzylpiperidin-4-yl)ethyl]-4-(6-chloropyridin-3-yl)-2,6-dimethylpiperazine-1-carboxamide (470.3);

(2R,6R)—N-[2-(1-benzylpiperidin-4-yl)ethyl]-2,6-dimethyl-4-[6-(trifluoromethyl)pyridazin-3-yl]piperazine-1-carboxamide 505.3

(2R)—N-[2-(1-benzylpiperidin-4-yl)ethyl]-4-(5-methoxypyrimidin-2-yl)-2-methylpiperazine-1-carboxamide (453.3);

(2R,6S)—N-[2-(1-benzylpiperidin-4-yl)ethyl]-4-(5-methoxypyrimidin-2-yl)-2,6-dimethylpiperazine-1-carboxamide (467.3);

(2R,6R)—N-[2-(1-benzylpiperidin-4-yl)ethyl]-4-(5-methoxypyrimidin-2-yl)-2,6-dimethylpiperazine-1-carboxamide (467.3);

(2R,6R)—N-[2-(1-benzylpiperidin-4-yl)ethyl]-4-(5-methoxypyrazin-2-yl)-2,6-dimethylpiperazine-1-carboxamide (467.3);

(2R,6R)—N-[2-(1-benzylpiperidin-4-yl)ethyl]-4-(6-methoxypyridazin-3-yl)-2,6-dimethylpiperazine-1-carboxamide (467.3);

(2R,6R)—N-[2-(1-benzylpiperidin-4-yl)ethyl]-4-(2-methoxypyrimidin-5-yl)-2,6-dimethylpiperazine-1-carboxamide (467.3);

(2R)—N-[2-(1-benzylpiperidin-4-yl)ethyl]-4-[5-(difluoromethoxy)pyrimidin-2-yl]-2-methylpiperazine-1-carboxamide (489.3);

(2R,6S)—N-[2-(1-benzylpiperidin-4-yl)ethyl]-4-[5-(difluoromethoxy)pyrimidin-2-yl]-2,6-dimethylpiperazine-1-carboxamide (503.3);

(2R,6R)—N-[2-(1-benzylpiperidin-4-yl)ethyl]-4-[5-(difluoromethoxy)pyrimidin-2-yl]-2,6-dimethylpiperazine-1-carboxamide (503.3);

(2R,6R)—N-[2-(1-benzylpiperidin-4-yl)ethyl]-4-[5-(difluoromethoxy)pyrazin-2-yl]-2,6-dimethylpiperazine-1-carboxamide (503.3);

(2R,6R)—N-[2-(1-benzylpiperidin-4-yl)ethyl]-4-[6-(difluoromethoxy)pyridazin-3-yl]-2,6-dimethylpiperazine-1-carboxamide (503.3);

(2R,6R)—N-[2-(1-benzylpiperidin-4-yl)ethyl]-4-[2-(difluoromethoxy)pyrimidin-5-yl]-2,6-dimethylpiperazine-1-carboxamide (503.3);

(2R)—N-[2-(1-benzylpiperidin-4-yl)ethyl]-2-methyl-4-[5-(trifluoromethoxy)pyrimidin-2-yl]piperazine-1-carboxamide (507.3);

(2R,6S)—N-[2-(1-benzylpiperidin-4-yl)ethyl]-2,6-dimethyl-4-[5-(trifluoromethoxy)pyrimidin-2-yl]piperazine-1-carboxamide (521.3);

(2R,6R)—N-[2-(1-benzylpiperidin-4-yl)ethyl]-2,6-dimethyl-4-[5-(trifluoromethoxy)pyrimidin-2-yl]piperazine-1-carboxamide (521.3);

(2R,6R)—N-[2-(1-benzylpiperidin-4-yl)ethyl]-2,6-dimethyl-4-[5-(trifluoromethoxy)pyrazin-2-yl]piperazine-1-carboxamide (521.3);

(2R,6R)—N-[2-(1-benzylpiperidin-4-yl)ethyl]-2,6-dimethyl-4-[6-(trifluoromethoxy)pyridazin-3-yl]piperazine-1-carboxamide (521.3);

(2R,6R)—N-[2-(1-benzylpiperidin-4-yl)ethyl]-2,6-dimethyl-4-[2-(trifluoromethoxy)pyrimidin-5-yl]piperazine-1-carboxamide (521.3);

N-[2-(1-benzylpiperidin-4-yl)ethyl]-4-(5-methoxypyrimidin-2-yl)piperazine-1-carboxamide (439.3);

N-[2-(1-benzylpiperidin-4-yl)ethyl]-4-[5-(difluoromethoxy)pyrimidin-2-yl]piperazine-1-carboxamide (475.3); and N-[2-(1-benzylpiperidin-4-yl)ethyl]-4-[5-(trifluoromethoxy)pyrimidin-2-yl]piperazine-1-carboxamide (492.2).

In even more specific embodiments, specific compounds of formula I are as listed in Tables 1-19 herein.

In other embodiments, pharmaceutical compositions are provided that comprise a compound of Formula I, including one or more of the specific compounds described herein (see, e.g., Tables 1-19), and at least one pharmaceutically acceptable excipient.

In another embodiment, a method is provided for antagonizing a muscarinic receptor in a cell comprising contacting the cell and a compound of Formula I, including specific compounds described herein, for a time sufficient and under appropriate conditions to permit interaction between the cell and the compound. In certain embodiments, the cell is in a subject who is in need of treatment with a compound disclosed herein. For example, the subject may have or be at risk for developing a neurological disease, condition, or disorder including cognitive and movement neurological diseases, conditions, and disorders. In certain embodiments, methods are provided for preventing (i.e., reducing the likelihood of occurrence of) or treating Alzheimer's Disease, Lewy Body Dementia and the cognitive deficits associated with schizophrenia; Parkinson's Disease, drug induced Parkinsonism, dyskinesias, dystonia, chorea, levodopa induced dyskinesia, cerebral palsy and progressive supranuclear palsy, and Huntington's disease, including chorea associate with Huntington's disease. A person skilled in the medical or neurological art will readily appreciate that many of the aforementioned neurological diseases have both cognitive deficits and movement deficiencies or difficulties associated with them.

As used in the specification and appended claims, unless specified to the contrary, the following terms have the meaning indicated.

Certain chemical groups named herein are preceded by a shorthand notation indicating the total number of carbon atoms that are to be found in the indicated chemical group. For example; $C_1$-$C_4$alkyl describes an alkyl group, as defined below, having a total of 1 to 4 carbon atoms, and $C_4$-$C_{12}$cycloalkylalkyl describes a cycloalkylalkyl group, as defined below, having a total of 4 to 12 carbon atoms. The total number of carbons in the shorthand notation does not include carbons that may exist in substituents of the group described. For example, the following terms have the meaning indicated.

"$C_1$-$C_6$alkyl" refers to an alkyl radical as defined below containing one to six carbon atoms. The $C_1$-$C_6$alkyl radical may be optionally substituted as defined below for an alkyl group. "$C_1$-$C_4$alkyl" refers to an alkyl radical as defined below containing one to four carbon atoms. The $C_1$-$C_4$alkyl radical may be optionally substituted as defined below for an alkyl group.

"$C_2$-$C_4$alkenyl" refers to an alkenyl radical as defined below containing two to six carbon atoms. The $C_2$-$C_{12}$alkenyl radical may be optionally substituted as defined below for an alkenyl group.

"$C_2$-$C_6$alkynyl" refers to an alknyl radical as defined below containing two to six carbon atoms. The $C_2$-$C_{12}$alknyl radical may be optionally substituted as defined below for an alkenyl group.

"$C_1$-$C_4$alkoxy" refers to an alkoxy radical as defined below containing one to twelve carbon atoms. The alkyl part of the $C_1$-$C_4$alkoxy radical may be optionally substituted as defined below for an alkyl group.

"$C_2$-$C_6$alkoxyalkyl" refers to an alkoxyalkyl radical as defined below containing two to six carbon atoms. Each alkyl part of the $C_2$-$C_6$alkoxyalkyl radical may be optionally substituted as defined below for an alkyl group.

"$C_7$-$C_{12}$aralkyl" refers to an aralkyl group as defined below containing seven to twelve carbon atoms. The aryl part of the $C_7$-$C_{12}$aralkyl radical may be optionally substituted as described below for an aryl group. The alkyl part of the $C_7$-$C_{12}$aralkyl radical may be optionally substituted as defined below for an alkyl group.

"$C_7$-$C_{12}$aralkenyl" refers to an aralkenyl group as defined below containing seven to twelve carbon atoms. The aryl part of the $C_7$-$C_{12}$aralkenyl radical may be optionally substituted as described below for an aryl group. The alkenyl part of the $C_7$-$C_{12}$aralkenyl radical may be optionally substituted as defined below for an alkenyl group.

"$C_3$-$C_{12}$cycloalkyl" refers to a cycloalkyl radical as defined below having three to twelve carbon atoms. The $C_3$-$C_{12}$cycloalkyl radical may be optionally substituted as defined below for a cycloalkyl group.

"$C_4$-$C_{12}$cycloalkylalkyl" refers to a cycloalkylalkyl radical as defined below having four to twelve carbon atoms. The $C_4$-$C_{12}$cycloalkylalkyl radical may be optionally substituted as defined below for a cycloalkylalkyl group.

In addition to the foregoing, as used in the specification and appended claims, unless specified to the contrary, the following terms have the meaning indicated:

"Alkyl" refers to a straight or branched hydrocarbon chain radical consisting solely of carbon and hydrogen atoms, containing no unsaturation, having from one to twelve carbon atoms, one to eight carbon atoms, or one to six carbon atoms, or one to four carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, and the like.

"Alkenyl" refers to a straight or branched hydrocarbon chain radical group consisting solely of carbon and hydrogen atoms, containing at least one double bond, having from two to twelve carbon atoms, preferably two to eight carbon atoms and which is attached to the rest of the molecule by a single bond, e.g., ethenyl, prop-1-enyl, but-1-enyl, pent-1-enyl, penta-1,4-dienyl, and the like.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms or from one to four carbon atoms, e.g., methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon or any two carbons within the chain.

"Alkenylene" or "alkenylene chain" refers to a straight or branched divalent hydrocarbon chain linking the rest of the molecule to a radical group, consisting solely of carbon and hydrogen, containing at least one double bond and having from two to twelve carbon atoms, e.g., ethenylene, propenylene, n-butenylene, and the like. The alkenylene chain is attached to the rest of the molecule through a single bond and to the radical group through a double bond or a single bond. The points of attachment of the alkenylene chain to the rest of the molecule and to the radical group can be through one carbon or any two carbons within the chain.

"Carbocyclyl" refers to a stable 3- to 18-membered aromatic or non-aromatic ring radical which consists of 3 to 18 carbon atoms. Unless stated otherwise specifically in the specification, the carbocyclyl radical may be a monocyclic, bicyclic, tricyclic or tetracyclic ring system, which may include fused or bridged ring systems, and may be partially or fully saturated. Non-aromatic carbocyclyl radicals include cycloalkyl, while aromatice carbocyclyl redicals include aryl.

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptly, and cyclooctyl. Polycyclic radicals include, for example, adamantyl, norbornyl, decalinyl, 7,7-dimethyl-bicyclo-[2.2.1]heptanyl, and the like.

"Aryl" refers to a hydrocarbon ring system radical comprising hydrogen, 6 to 18 carbon atoms and at least one aromatic ring. The aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. In one embodiment, aryl is phenyl or naphthyl, and in another embodiment is phenyl.

"Heterocyclyl" refers to a stable 3- to 18-membered aromatic or non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples or aromatic hetercyclyl radicals are listed below in the definition of heteroaryls (i.e., heteroaryl being a subset of heterocyclyl). Examples of non-aromatic heterocyclyl radicals include, but are not limited to, dioxolanyl, thienyl [1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, pyrazolopyrimidinyl, quinuclidinyl, thiazolidinyl, tetrahydrofuryl, trioxanyl, trithianyl, triazinanyl, tetrahydropyranyl, thiomorpholinyl, thiamorpholinyl, 1-oxo-thiomorpholinyl, and 1,1-dioxo-thiomorpholinyl.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzthiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, benzoxazolinonyl, benzimidazolthionyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, pteridinonyl, purinyl, pyrrolyl, pyrazolyl, pyridinyl, pyridinonyl, pyrazinyl, pyrimidinyl, pryrimidinonyl, pyridazinyl, pyrrolyl, pyrido[2,3-d]pyrimidinonyl, quinazolinyl, quinazolinonyl, quinoxalinyl, quinoxalinonyl, quinolinyl, isoquinolinyl, tetrahydroquinolinyl, thiazolyl, thiadiazolyl, thieno[3,2-d]pyrimidin-4-onyl, thieno[2,3-d]pyrimidin-4-onyl, triazolyl, tetrazolyl, triazinyl, and thiophenyl (i.e. thienyl).

Unless stated otherwise specifically in the specification, each of alkyl, alkenyl, alkylene, alkenylene, carbocyclyl, cycloalkyl, aryl, heterocyclyl and heteroaryl as defined above may be optionally substituted by one or more substituents selected from the group consisting of alkyl, alkenyl, halo, haloalkyl, haloalkenyl, cyano, oxo, thioxo, nitro, aryl, aralkyl, cycloalkyl, cycloalkylalkyl, heterocyclyl, heterocyclylalkyl, heteroaryl, heteroarylalkyl, —$R^{41}$—$OR^{40}$, —$R^{41}$—$OC(O)$—$R^{40}$, —$R^{41}$—$N(R^{40})_2$, —$R^{41}$—$C(O)R^{40}$, —$R^{41}$—$C(O)OR^{40}$, —$R^{41}$—$C(O)N(R^{40})_2$, —$R^{41}$—$N(R^{40})C(O)OR^{42}$, —$R^{41}$—$N(R^{40})C(O)R^{42}$, —$R^{41}$—$N(R^{40})S(O)_tR^{42}$ (where t is 1 to 2), —$R^{41}$—$N=C(OR^{40})R^{40}$, —$R^{41}$—$S(O)_tOR^{42}$ (where t is 1 to 2), —$R^{41}$—$S(O)_pR^{42}$ (where p is 0 to 2), and —$R^{41}$—$S(O)_tN(R^{40})_2$ (where t is 1 to 2) where each $R^{40}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{41}$ is independently a direct bond or a straight or branched alkylene or alkenylene chain; and each $R^{42}$ is alkyl, alkenyl, haloalkyl, cycloalkyl, cycloalkylalkyl, aryl, aralkyl, heterocyclyl, heterocyclylalkyl, heteroaryl or heteroarylalkyl.

"Amino" refers to the —$NH_2$ radical.

"Cyano" refers to the —CN radical.

"Hydroxy" refers to the —OH radical.

"Nitro" refers to the —$NO_2$ radical.

"Oxo" refers to the =O substituent.

"Thioxo" refers to the =S substituent.

"Trifluoromethyl" refers to the —$CF_3$ radical.

"Trifluoromethoxy" refers to the —$OCF_3$ radical.

"Acyl" refers to a radical —C(O)R, wherein R is alkyl, aralkyl, carbocyclyl, aryl, heteroaryl, or heterocyclyl, as defined herein. When R is methyl, the acyl group is also referred to as acetyl.

"Heteroalkylene" or "heteroalkylene chain" refers to a straight or branched divalent hydrocarbon chain linking the rest of the molecule to a radical group, consisting of carbon and hydrogen and at least one heteroatom selected from N, O, and S.

"Alkoxy" refers to a radical of the formula —$OR_a$ where $R_a$ is an alkyl, or haloalkyl radical as defined above containing one to six carbon atoms. Representative alkoxy groups include methoxy and ethoxy. Unless stated otherwise specifically in the specification, an alkoxy group may be optionally substituted. An alkoxy that is substituted with halo may be called herein a haloalkoxy, which includes for example trifluoromethoxy, trichloromethoxy and the like.

"Heteroalkenylene" or "heteroalkenylene chain" refers to a straight or branched divalent hydrocarbon chain linking the rest of the molecule to a radical group, consisting of carbon and hydrogen and at least one heteroatom selected from N, O, and S.

"Aralkyl" refers to a radical of the formula —$R_b$—$R_c$ where $R_b$ is an alkylene chain as defined above and $R_c$ is one or more aryl radicals as defined above, for example, benzyl, diphenylmethyl and the like. The alkylene chain part of the aralkyl radical may be optionally substituted as described above for an alkylene chain. The aryl part of the aralkyl radical may be optionally substituted as described above for an aryl group.

"Cycloalkylalkyl" refers to a radical of the formula —$R_bR_g$ where $R_b$ is an alkylene chain as defined above and $R_g$ is a cycloalkyl radical as defined above. The alkylene chain and the cycloalkyl radical may be optionally substituted as defined above.

"Fused" refers to any ring system described herein which is fused to an existing ring structure in the compounds of the invention. When the fused ring system is a heterocyclyl or a heteroaryl, any carbon in the existing ring structure which becomes part of the fused ring system may be replaced with a nitrogen.

"Halo" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. The alkyl part of the haloalkyl radical may be optionally substituted as defined above for an alkyl group.

"Haloalkenyl" refers to an alkenyl radical, as defined above, that is substituted by one or more halo radicals, as defined above. The alkenyl part of the haloalkyl radical may be optionally substituted as defined above for an alkenyl group.

"Haloalkoxy" refers to an alkoxy radical, as defined above, that is substituted by one or more halo radicals, as defined above, e.g., trifluoromethoxy, difluoromethoxy, trichloromethoxy, 2,2,2-trifluoroethoxy, 3-bromo-2-fluoropropyloxy, and the like. The alkoxy part of the haloalkoxy radical may be optionally substituted as defined above for an alkoxy group.

"N-heterocyclyl" refers to a heterocyclyl radical as defined above containing at least one nitrogen. An N-heterocyclyl radical may be optionally substituted as described above for heterocyclyl radicals.

"Heterocyclylalkyl" refers to a radical of the formula —$R_bR_h$ where $R_b$ is an alkylene chain as defined above and $R_h$ is a heterocyclyl radical as defined above, and if the heterocyclyl is a nitrogen-containing heterocyclyl, the heterocyclyl may be attached to the alkyl radical at the nitrogen atom. The alkylene chain of the heterocyclylalkyl radical may be optionally substituted as defined above for an alkyene chain. The heterocyclyl part of the heterocyclylalkyl radical may be optionally substituted as defined above for a heterocyclyl group.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical may be optionally substituted as described above for heteroaryl radicals.

"Heteroarylalkyl" refers to a radical of the formula —$R_bR_i$ where $R_b$ is an alkylene chain as defined above and $R_i$ is a heteroaryl radical as defined above. The heteroaryl part of the heteroarylalkyl radical may be optionally substituted as defined above for a heteroaryl group. The alkylene chain part of the heteroarylalkyl radical may be optionally substituted as defined above for an alkylene chain.

"Hydroxyalkyl" refers to a radical of the formula —$R_b$OH where $R_b$ is an alkylene chain as defined above. The —OH group can be attached to any carbon in the alkylene chain. The alkylene chain part of the heteroarylalkyl radical may additionally be optionally substituted as defined above for an alkylene chain.

The compounds described herein may generally be used as the free acid or free base. Alternatively, the compounds may be used in the form of acid or base addition salts. Acid addition salts of the free amino compounds may be prepared by methods well known in the art, and may be formed from organic and inorganic acids. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Base addition salts included those salts that form with the carboxylate anion and include salts formed with organic and inorganic cations such as those chosen from the alkali and alkaline earth metals (for example, lithium, sodium, potassium, magnesium, barium and calcium), as well as the ammonium ion and substituted derivatives thereof (for example, dibenzylammonium, benzylammonium, 2-hydroxyethylammonium, and the like). Thus, the term "pharmaceutically acceptable salt" of the compounds described herein is intended to encompass any and all acceptable salt forms.

Compounds described herein may sometimes be depicted as an anionic species. One of ordinary skill in the art will recognize that the compounds exist with an equimolar ratio of cation. For instance, the compounds can exist in the fully protonated form, or in the form of a salt such as sodium, potassium, ammonium or in combination with any inorganic base as described above. When more than one anionic species is depicted, each anionic species may independently exist as either the protonated species or as the salt species.

With regard to stereoisomers, the compounds described herein may have one or more chiral (or asymmetric) centers and may thus give rise to enantiomers, diastereomers, and other stereoisomeric forms that may be defined, in terms of absolute stereochemistry, as (R)- or (S)-. When the compounds described herein contain olefinic double bonds or other centers of geometric asymmetry, and unless specified otherwise, it is intended that the compounds include both E and Z geometric isomers (e.g., cis or trans). Likewise, unless otherwise indicated, all possible isomers, as well as their racemic and optically pure forms, and all tautomeric forms are also intended to be included. It is therefore contemplated that various stereoisomers and mixtures thereof include "enantiomers," which refers to two stereoisomers whose molecules are nonsuperimposeable mirror images of one another. Thus, the compounds may occur in any isomeric form, including racemates, racemic mixtures, and as individual enantiomers or diastereomers.

Furthermore, some of the crystalline forms of the compounds may exist as polymorphs, which are contemplated herein. In addition, some of the compounds may also form solvates with water or other organic solvents. Such solvates are similarly included within the scope of the compounds described herein.

As one of skill in the art would appreciate, any of the aforementioned compounds may incorporate radioactive isotopes. Accordingly, also contemplated is use of isotopically-labeled compounds identical to those described herein, wherein one or more atoms are replaced by an atom having an atomic mass or mass number different from the atomic mass or mass number usually found in nature. Examples of isotopes that can be incorporated into these compounds include isotopes of hydrogen, carbon, nitrogen, oxygen, phosphorous, fluorine and chlorine, such as, but not limited to, $^{2}H$, $^{3}H$, $^{13}C$, $^{14}C$, $^{15}N$, $^{18}O$, $^{17}O$, $^{31}F$, $^{32}F$, $^{35}S$, $^{18}F$, and $^{36}Cl$, respectively. Certain isotopically-labeled compounds, for example those into which radioactive isotopes such as $^{3}H$ and $^{14}C$ are incorporated, are also useful in drug or substrate tissue distribution assays. Tritiated hydrogen ($^{3}H$) and carbon-14 ($^{14}C$) isotopes are particularly preferred for their ease of preparation and detectability. Substitution with heavier isotopes such as deuterium ($^{2}H$) can provide certain therapeutic advantages resulting from greater metabolic stability, for example increased in vivo half-life or reduced dose requirements and, therefore, may be preferred in some circumstances. To this end, reference to an element, such as hydrogen (H) or carbon (C), is intended to encompass all isotopes of the same. Thus, reference to H encompasses $^{1}H$ (protium), $^{2}H$ (deuterium) and $^{3}H$ (tritium), and reference to C encompasses $^{12}C$, $^{13}C$ and $^{14}C$. For example, compounds of formula (I) wherein both $R_1$ groups are $^{2}H$ (deuterium) are encompassed within the scope of this invention by reference to $R_1$ being, in one embodiment, hydrogen (H). Isotopically-labeled compounds can generally be prepared by performing procedures routinely practiced in the art.

"Prodrug" is meant to indicate a compound that may be converted under physiological conditions or by solvolysis to a biologically active compound described herein. Thus, the term "prodrug" refers to a metabolic precursor of a compound described herein that is pharmaceutically acceptable. A prodrug may be inactive when administered to a subject in need thereof, but is converted in vivo to an active compound as described herein. Prodrugs are typically rapidly transformed in vivo to yield the parent compound described herein, for example, by hydrolysis in blood. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers which release the active compound as described herein in vivo when such prodrug is administered to a mammalian subject. Prodrugs of a compound described herein may be prepared by modifying functional groups present in the compound described herein in such a way that the modifications are cleaved, either in routine manipulation or in vivo, to the parent compound described herein. Prodrugs include compounds described herein wherein a hydroxy, amino or mercapto group is bonded to any group that, when the prodrug of the compound is administered to a mammalian subject, cleaves to form a free hydroxy, free amino or free mercapto group, respectively. Examples of prodrugs include, but are not limited to, ester and amide derivatives of hydroxy, carboxy, mercapto or amino functional groups in the compounds described herein and the like.

In general, the compounds used in the reactions described herein may be made according to organic synthesis techniques known to those skilled in this art, starting from commercially available chemicals and/or from compounds described in the chemical literature. "Commercially available chemicals" may be obtained from standard commercial sources including Across Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hanover, Germany), Spectrum Quality Product, Inc. (New Brunswick, N.J.), TCI America (Portland Oreg.), Trans World Chemicals, Inc. (Rockville Md.), and Wako Chemicals USA, Inc. (Richmond Va.).

Methods known to one of ordinary skill in the art may be identified through various reference books and databases. Suitable reference books and treatise that detail the synthesis of reactants useful in the preparation of compounds of the present disclosure, or provide references to articles that describe the preparation, include for example, "Synthetic Organic Chemistry," John Wiley & Sons, Inc., New York; S. R. Sandler et al., "Organic Functional Group Preparations," 2nd Ed., Academic Press, New York, 1983; H. O. House, "Modem Synthetic Reactions", 2nd Ed., W. A. Benjamin, Inc. Menlo Park, Calif 1972; T. L. Gilchrist, "Heterocyclic Chemistry", 2nd Ed., John Wiley & Sons, New York, 1992; J. March, "Advanced Organic Chemistry: Reactions, Mechanisms and Structure," 4th Ed., Wiley-Interscience, New York, 1992. Additional suitable reference books and treatise that detail the synthesis of reactants useful in the preparation of compounds of the present disclosure, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Quin, L. D. et al. "A Guide to Organophosphorus Chemistry" (2000) Wiley-Interscience, ISBN: 0-471-31824-8; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services. A reference for the preparation and selection of pharmaceutical salts of the present disclosure is P. H. Stahl & C. G. Wermuth "Handbook of Pharmaceutical Salts," Verlag Helvetica Chimica Acta, Zurich, 2002.

Compound Synthesis

Detailed compound synthesis methods are described herein in the Examples. A person having ordinary skill in the chemical art would be able to make a compound of Formula I, including specific compounds described herein, by these methods or similar methods or other methods practiced by a person skilled in the art. In general, starting components may be obtained from commercial sources.

Methods of Treatment

Methods are provided herein for treating or preventing (i.e., reducing the likelihood of occurrence of neurological condition, disease or disorder including but not limited to Alzheimer's Disease, Lewy Body Dementia and the cognitive deficits associated with schizophrenia; Parkinson's Disease, drug induced Parkinsonism, dyskinesias, dystonia, chorea, levodopa induced dyskinesia, cerebral palsy and progressive supranuclear palsy, and Huntington's disease, including chorea associate with Huntington's disease. While some of these diseases are considered cognitive disorders (e.g., Alzheimer's disease), and other diseases are considered neurological movement diseases/disorders, several have both cognitive and movement deficiencies or conditions associated with them (e.g., Parkinson's disease, Huntington's disease).

The effectiveness of a muscarinic receptor antagonist, such as a selective M4 antagonist, with respect to treating a neurological condition, disease or disorder described herein can readily be determined by a person skilled in the medical and clinical arts. One or any combination of diagnostic methods appropriate for the particular disease or disorder, which methods are well known to a person skilled in the art, including physical examination, patient self-assessment, assessment and monitoring of clinical symptoms, performance of analytical tests and methods, including clinical laboratory tests, physical tests, and exploratory surgery, for example, may be used for monitoring the health status of the subject and the effectiveness of the inhibitor. The effects of the methods of treatment described herein can be analyzed using techniques known in the art, such as comparing symptoms of patients suffering from or at risk of a particular disease or disorder that have received the pharmaceutical composition comprising an antagonist with those of patients who were not treated with the inhibitor or who received a placebo treatment.

As understood by a person skilled in the medical art, the terms, "treat" and "treatment," refer to medical management of a disease, disorder, or condition of a subject (i.e., patient) (see, e.g., Stedman's Medical Dictionary). In general, an appropriate dose and treatment regimen provide the M4 antagonist in an amount sufficient to provide therapeutic and/or prophylactic benefit. Therapeutic benefit for subjects to whom the M4 antagonist compound(s) described herein are administered, includes, for example, an improved clinical outcome, wherein the object is to prevent or slow or retard (lessen) an undesired physiological change associated with the disease, or to prevent or slow or retard (lessen) the expansion or severity of such disease. As discussed herein, effectiveness of the one or more M4 antagonists may include beneficial or desired clinical results that comprise, but are not limited to, abatement, lessening, or alleviation of symptoms that result from or are associated with the disease to be treated; decreased occurrence of symptoms; improved quality of life; longer disease-free status (i.e., decreasing the likelihood or the propensity that a subject will present symptoms on the basis of which a diagnosis of a disease is made); diminishment of extent of disease; stabilized (i.e., not worsening) state of disease; delay or slowing of disease progression; amelioration or palliation of the disease state; and remission (whether partial or total), whether detectable or undetectable; and/or overall survival.

"Treatment" can also mean prolonging survival when compared to expected survival if a subject were not receiving treatment. Subjects in need of treatment include those who already have the disease or disorder as well as subjects prone to have or at risk of developing the disease or disorder, and those in which the disease, condition, or disorder is to be prevented (i.e., decreasing the likelihood of occurrence or recurrence of the disease or disorder).

A subject (i.e., patient, individual) in need of treatment with an M4 antagonist as described herein may be a human or may be a non-human primate or other animal (i.e., veterinary use) who has developed symptoms of a hyperkinetic disease or disorder or who is at risk for developing a hyperkinetic disease or disorder. Non-human animals that may be treated include mammals, for example, non-human primates (e.g., monkey, chimpanzee, gorilla, and the like), rodents (e.g., rats, mice, gerbils, hamsters, ferrets, rabbits), lagomorphs, swine (e.g., pig, miniature pig), equine, canine, feline, bovine, elephants, bears and other domestic, farm, and zoo animals.

Pharmaceutical Compositions

The present disclosure further provides for pharmaceutical compositions comprising any one of the M4 antagonist compounds described herein (a compound of Formula I, including specific compounds described herein) and a pharmaceutically acceptable excipient for use in the methods for treating hyperkinetic disorders. A pharmaceutically acceptable excipient is a physiologically and pharmaceutically suitable non-toxic and inactive material or ingredient that does not interfere with the activity of the active ingredient; an excipient also may be called a carrier. The formulation methods and excipients described herein are exemplary and are in no way limiting. Pharmaceutically acceptable excipients are well known in the pharmaceutical art and described, for example, in Rowe et al., Handbook of Pharmaceutical Excipients: A Comprehensive Guide to Uses, Properties, and Safety, 5$^{th}$ Ed., 2006, and in *Remington: The Science and Practice of Pharmacy* (Gennaro, 21$^{st}$ Ed. Mack Pub. Co., Easton, Pa. (2005)). Exemplary pharmaceutically acceptable excipients include sterile saline and phosphate buffered saline at physiological pH. Preservatives, stabilizers, dyes, buffers, and the like may be provided in the pharmaceutical composition. In addition, antioxidants and suspending agents may also be used.

For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to an M4 antagonist, diluents, dispersing and surface active agents, binders, and lubricants. One skilled in this art may further formulate the M4 antagonist in an appropriate manner, and in accordance with accepted practices, such as those disclosed in Remington, supra.

Methods of administration include systemic administration of an M4 antagonist described herein, preferably in the form of a pharmaceutical composition as discussed above. As used herein, systemic administration includes oral and parenteral methods of administration. For oral administration, suitable pharmaceutical compositions include powders, granules, pills, tablets, and capsules as well as liquids, syrups, suspensions, and emulsions. These compositions may also include flavorants, preservatives, suspending, thickening and emulsifying agents, and other pharmaceutically acceptable additives. For parental administration, the compounds of the present invention can be prepared in aqueous injection solutions which may contain, in addition to the M4 antagonist, buffers, antioxidants, bacteriostats, and other additives commonly employed in such solutions.

As described herein optimal doses are generally determined using experimental models and/or clinical trials. The optimal dose of the M4 antagonist may depend upon the body mass, weight, blood volume, or other individual characteristics of the subject. For example, a person skilled in the medical art can consider the subject's condition, that is, stage of the disease, severity of symptoms caused by the disease, general health status, as well as age, gender, and weight, and other factors apparent to a person skilled in the medical art. In general, the amount of a compound described herein, that is present in a dose ranges from about 0.1 mg to about 2 mg per kg weight of the subject. In certain embodiments, a daily dose is about 10-150 mg. The use of the minimum dose that is sufficient to provide effective therapy is usually preferred. Subjects may generally be monitored for therapeutic effectiveness by clinical evaluation and using assays suitable for the condition being treated or prevented, which methods will be familiar to those having ordinary skill in the art and are described herein. The level of a compound that is administered to a subject may be monitored by determining the level of the compound in a biological fluid, for example, in the blood, blood fraction (e.g., plasma, serum), and/or in the urine, and/or other biological sample from the subject. Any method practiced in the art to detect the compound may be used to measure the level of compound during the course of a therapeutic regimen.

Pharmaceutical composition comprising an M4 antagonist may formulated for timed release (also called extended release, sustained release, controlled release, or slow release). Such compositions may generally be prepared using well known technology and administered by, for example, oral, rectal or subcutaneous implantation, or by implantation at the desired target site. Sustained-release formulations may contain the compound dispersed in a carrier matrix and/or contained within a reservoir surrounded by a rate controlling membrane. Excipients for use within such formulations are biocompatible, and may also be biodegradable; preferably the formulation provides a relatively constant level of active component release. The amount of active compound contained within a sustained release formulation depends upon the site of implantation, the rate and expected duration of release, and the nature of the condition to be treated or prevented.

The pharmaceutical compositions described herein that comprise at least one of the M4 antagonist compounds described herein may be administered to a subject in need by any one of several routes that effectively deliver an effective amount of the compound. Such administrative routes include, for example, oral, parenteral (e.g., subcutaneous, intravenous, intramuscular, intrasternal, intracavernous), enteral, rectal, intranasal, buccal, sublingual, intramuscular, and transdermal.

Kits with unit doses of one or more of the compounds described herein, usually in oral or injectable doses, are provided. Such kits may include a container containing the unit dose, an informational package insert describing the use and attendant benefits of the drugs in treating pathological condition of interest, and optionally an appliance or device for delivery of the composition.

EXAMPLES

Example 1

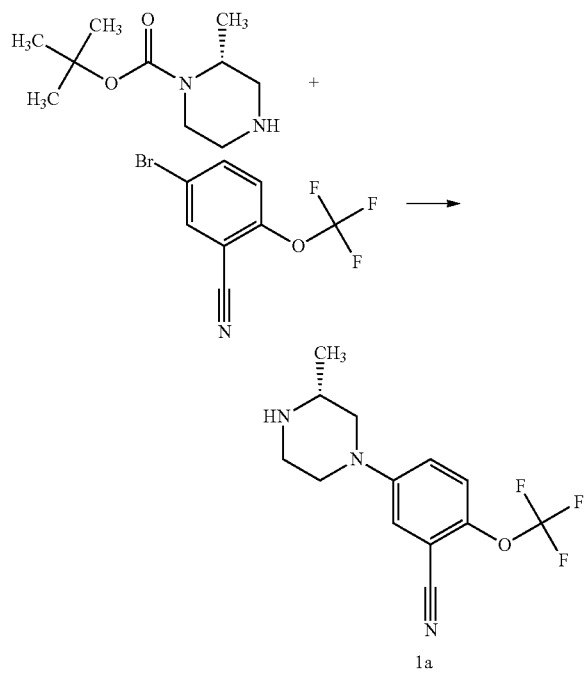

Step 1A: 5-[(3R)-3-methylpiperazin-1-yl]-2-(trifluoromethoxy)benzonitrile

To a solution of tert-butyl (2R)-2-methylpiperazine-1-carboxylate (5.0 g, 25 mmol, 1.0 eq) and 5-bromo-2-(trifluoromethoxy)benzonitrile (3.8 mL, 25 mmol, 1 eq) in toluene (100 mL) was added sodium tert-butoxide (7.2 g, 75 mmol, 3.0 eq), racemic 2,2'-bis(diphenylphosphino)-1,1'-binaphthyl (1.6 g, 2.5 mmol, 0.10 eq), and lastly tris(dibenzylideneacetone)dipalladium(0) (2.3 g, 2.5 mmol, 0.10 eq), and the reaction mixture heated to 100° C. overnight. The resulting dark reaction mixture was cooled, passed thru a pad of celite, and concentrated in vacuo. Silica gel column (80 g) was dry loaded and run using an increasing gradient of EtOAc (0-50%) in hexanes over 25 min. The chromatographed material was dissolved in dioxane (40 mL) and treated with a solution of 4M HCl in dioxane (10 mL). The resulting thick suspension was concentrated, dissolved in MeOH, and made basic with the addition of MP-carbonate. Following removal of the resin and concentration of the filtrate, the free base of 5-[(3R)-3-methylpiperazin-1-yl]-2-(trifluoromethoxy)benzonitrile 1a (5.2 g, 18 mmol, 72% over two steps) was isolated as an orange oil.

In general, this reaction is completed with stirring overnight, however if necessary, additional acid equivalents and/or gentle heat (50° C.) can be used to push the reaction.

Other compounds made using the above synthetic scheme include:

1-(3,4-difluorophenyl)piperazine 1b;

3-(piperazin-1-yl)benzonitrile 1c;

2-fluoro-5-(piperazin-1-yl)benzonitrile 1d;

3-fluoro-5-(piperazin-1-yl)benzonitrile 1e;

1-[4-(trifluoromethoxy)phenyl]piperazine 1f;

1-[3-(trifluoromethoxy)phenyl]piperazine 1g;

1-(3,4,5-trifluorophenyl)piperazine 1h;

(3R)-3-methyl-1-[4-(trifluoromethyl)phenyl]piperazine 1i;

2-fluoro-5-[(3R)-3-methylpiperazin-1-yl]benzonitrile 1j;

3-fluoro-5-[(3R)-3-methylpiperazin-1-yl]benzonitrile 1k;

(3R)-3-methyl-1-(3,4,5-trifluorophenyl)piperazine 1l;

(3R)-3-methyl-1-[5-(trifluoromethyl)pyridin-2-yl]piperazine 1m;

(3R)-1-[3-fluoro-5-(trifluoromethyl)pyridin-2-yl]-3-methylpiperazine 1n;

(3R)-3-methyl-1-[5-(trifluoromethoxy)pyridin-2-yl]piperazine 1o; and (3R)-3-methyl-1-[6-(trifluoromethoxy)pyridin-3-yl]piperazine 1p.

Example 2

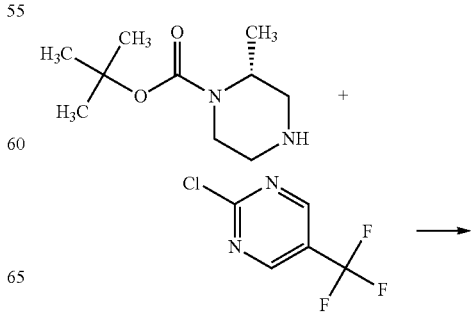

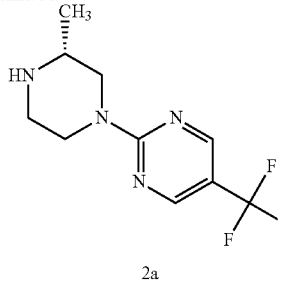

2a

STEP 2A: 2-[(3R)-3-METHYLPIPERAZIN-1-YL]-5-(TRIFLUOROMETHYL)PYRIMIDINE

To a solution of tert-butyl (2R)-2-methylpiperazine-1-carboxylate (2.2 g, 11.0 mmol, 1.0 eq) and 2-chloro-5-(trifluoromethyl)pyrimidine (2.0 g, 11.0 mmol, 1.0 eq) in 1-methyl-2-pyrrolidone (NMP,10 mL) was added N,N-diisopropylethylamine (5.7 mL, 44.0 mmol, 4.0 eq) and the reaction mixture heated to 100° C. for 1 hr. The reaction mixture was cooled, diluted heavily with EtOAc, and washed repeatedly with brine (5×). The organic layer was dried over Na$_2$SO$_4$ and concentrated. Silica gel column (80 g) was loaded using methylene chloride and run using an increasing gradient of EtOAc (5-90%) in hexanes over 20 min. The chromatographed material was dissolved in dioxane (25 mL) and treated with a solution of 4M HCl in dioxane (6 mL). The resulting thick white suspension was concentrated, dissolved in MeOH, and made basic with the addition of MP-carbonate. Following removal of the resin and concentration of the filtrate, the free base of 2-[(3R)-3-methylpiperazin-1-yl]-5-(trifluoromethyl)pyrimidine 2a (1.9 g, 7.6 mmol, 69% over two steps) was isolated as a white solid.

In general, this reaction is completed with stirring overnight, however if necessary, additional acid equivalents and/or gentle heat (50° C.) can be used to push the reaction.

Other compounds made using the above synthetic scheme include:

4-(dimethylamino)-2-[(3R)-3-methylpiperazin-1-yl]pyrimidine-5-carbonitrile 2b;
2-[(1S,4S)-2,5-diazabicyclo[2.2.1]heptan-2-yl]pyrimidine-5-carbonitrile 2c;
2-[(3R)-3-methylpiperazin-1-yl]-5-(trifluoromethyl)pyrimidin-4-amine 2d;
2-[(3R)-3-methylpiperazin-1-yl]pyrimidine-5-carbonitrile 2e;
2-[(3R,5S)-3,5-dimethylpiperazin-1-yl]pyrimidine-5-carbonitrile 2f;
2-{2,5-diazabicyclo[2.2.2]octan-2-yl}pyrimidine-5-carbonitrile 2g;
2-{2,6-diazaspiro[3.3]heptan-2-yl}pyrimidine-5-carbonitrile 2h;
2-{3,6-diazabicyclo[3.1.1]heptan-3-yl}pyrimidine-5-carbonitrile 2i;
2-{3,8-diazabicyclo[3.2.1]octan-3-yl}pyrimidine-5-carbonitrile 2j;
5-chloro-2-[(3R)-3-methylpiperazin-1-yl]pyrimidine 2k;
5-chloro-2-[(3R,5S)-3,5-dimethylpiperazin-1-yl]pyrimidine 2l;
6-[(3R,5S)-3,5-dimethylpiperazin-1-yl]-5-fluoropyridine-3-carbonitrile 2m; and
6-[(3R,5S)-3,5-dimethylpiperazin-1-yl]pyridine-3-carbonitrile 2n.

Example 3

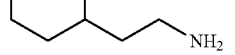

Step 3A: (2R)—N-[2-(1-benzylpiperidin-4-yl)ethyl]-4-[3-cyano-4-(trifluoromethoxy)phenyl]-2-methylpiperazine-1-carboxamide Triphosgene (2.1 g, 7.2 mmol, 0.40 eq) was dissolved in methylene chloride (50 mL) and a solution of 5-[(3R)-3-methylpiperazin-1-yl]-2-(trifluoromethoxy)benzonitrile 1a (5.2 g, 18 mmol, 1.0 eq) and N,N-diisopropylethylamine (6.0 mL, 36 mmol, 2.0 eq) in methylene chloride (50 mL) was added dropwise at room temperature. Once the addition was complete, the reaction mixture was stirred for 10 min before a solution of 2-(1-benzylpiperidin-4-yl])ethan-1-amine (4.8 g, 22 mmol, 1.2 eq) and N,N-diisopropylethylamine (6.0 mL, 36 mmol, 2.0 eq) in methylene chloride (50 mL) was added and stirred at room temperature for an additional 1 hr. Then, the reaction was diluted further with methylene chloride and washed with sat. NH$_4$Cl followed by sat. NaHCO$_3$. The combined organic layers were dried over Na$_2$SO$_4$ and concentrated in vacuo. Silica gel column (80 g) was loaded using methylene chloride and run with an increasing gradient of MeOH (0-20%) in methylene chloride over 20 min to provide (2R)—N-[2-(1-benzylpiperidin-4-yl)ethyl]-4-[3-cyano-4-(trifluoromethoxy)phenyl]-2-methylpiperazine-1-carboxamide 3-1 (5.2 g, 9.8 mmol, 54%) as an orange oil. The table below provides the observed (Obs) ion m/z ratio for 3-1 (first compound listed in Table 1) and other compounds that were made according to the procedure as described in this example.

TABLE 1

| Cpd. No. | Compound Name | Obs Ion (m/z) |
|---|---|---|
| 3-1 | (2R)-N-[2-(1-benzylpiperidin-4-yl)ethyl]-4-[3-cyano-4-(trifluoromethoxy)phenyl]-2-methylpiperazine-1-carboxamide | 530.2 |
| 3-2 | (1S)-1-(1-benzylpiperidin-4-yl)-2-{[(2R)-4-(3-cyano-4-fluorophenyl)-2-methylpiperazine-1-carbonyl]amino}ethyl acetate | 522.25 |
| 3-3 | (2R)-N-[(2S)-2-(1-benzylpiperidin-4-yl)-2-hydroxyethyl]-4-(3-cyano-4-fluorophenyl)-N,2-dimethylpiperazine-1-carboxamide | 494.2 |
| 3-4 | (2R)-N-[2-(1-benzylpiperidin-4-yl)ethyl]-4-(3-cyano-4-fluorophenyl)-N,2-dimethylpiperazine-1-carboxamide | 478.2 |
| 3-5 | (2R)-N-[2-(1-benzyl-4-hydroxypiperidin-4-yl)ethyl]-4-[3-cyano-4-(trifluoromethoxy)phenyl]-2-methylpiperazine-1-carboxamide | 546.2 |
| 3-6 | (2R)-N-[(2S)-2-(1-benzylpiperidin-4-yl)-2-methoxyethyl]-4-(3-cyano-4-fluorophenyl)-2-methylpiperazine-1-carboxamide | 494.2 |
| 3-7 | (2R)-4-[3-cyano-4-(trifluoromethoxy)phenyl]-N-(2-{1-[(4-iodophenyl)methyl]piperidin-4-yl}ethyl)-2-methylpiperazine-1-carboxamide | 656.1 |
| 3-8 | (2R)-N-[2-(1-benzylpiperidin-4-yl)ethyl]-2-methyl-4-[6-(trifluoromethoxy)pyridin-3-yl]piperazine-1-carboxamide | 506.2 |
| 3-9 | (2R)-N-[2-(1-benzylpiperidin-4-yl)ethyl]-2-methyl-4-[5-(trifluoromethyl)pyrimidin-2-yl]piperazine-1-carboxamide | 491.2 |
| 3-10 | (2R)-N-[2-(1-benzylpiperidin-4-yl)ethyl]-4-[3-fluoro-5-(trifluoromethyl)pyridin-2-yl]-2-methylpiperazine-1-carboxamide | 508.2 |
| 3-11 | (2R)-N-[2-(1-benzylpiperidin-4-yl)ethyl]-4-(3-cyano-5-fluorophenyl)-2-methylpiperazine-1-carboxamide | 464.2 |
| 3-12 | (2R)-N-[2-(1-benzylpiperidin-4-yl)ethyl]-2-methyl-4-(3,4,5-trifluorophenyl)piperazine-1-carboxamide | 475.2 |
| 3-13 | (2R)-N-[2-(1-benzylpiperidin-4-yl)ethyl]-2-methyl-4-[5-(trifluoromethoxy)pyridin-2-yl]piperazine-1-carboxamide | 506.2 |
| 3-14 | (2R)-N-[2-(1-benzylpiperidin-4-yl)ethyl]-2-methyl-4-[5-(trifluoromethyl)pyridin-2-yl]piperazine-1-carboxamide | 490.2 |
| 3-15 | (2R)-N-[2-(1-benzylpiperidin-4-yl)ethyl]-4-(4-cyanopyrimidin-2-yl)-2-methylpiperazine-1-carboxamide | 448.2 |
| 3-16 | (2R)-N-[(2R)-2-(1-benzylpiperidin-4-yl)-2-hydroxyethyl]-2-methyl-4-(3,4,5-trifluorophenyl)piperazine-1-carboxamide | 491.2 |
| 3-17 | (2R)-N-{2-[1-benzyl-3-(hydroxymethyl)piperidin-4-yl]ethyl}-2-methyl-4-(3,4,5-trifluorophenyl)piperazine-1-carboxamide | 505.2 |
| 3-18 | (2R)-N-[(2S)-2-(1-benzylpiperidin-4-yl)-2-hydroxyethyl]-4-(3-cyano-4-fluorophenyl)-2-methylpiperazine-1-carboxamide | 480.2 |
| 3-19 | N-{2-[1-benzyl-3-(hydroxymethyl)piperidin-4-yl]ethyl}-4-(3,4,5-trifluorophenyl)piperazine-1-carboxamide | 491.2 |
| 3-20 | (2R)-N-{2-[1-benzyl-4-(hydroxymethyl)piperidin-4-yl]ethyl}-2-methyl-4-(3,4,5-trifluorophenyl)piperazine-1-carboxamide | 505.2 |
| 3-21 | (2R)-N-[(2S)-2-(1-benzylpiperidin-4-yl)-2-hydroxyethyl]-4-[3-cyano-4-(trifluoromethoxy)phenyl]-2-methylpiperazine-1-carboxamide | 546.2 |
| 3-22 | (2R)-N-[(2S)-2-(1-benzylpiperidin-4-yl)-2-hydroxyethyl]-2-methyl-4-(3,4,5-trifluorophenyl)piperazine-1-carboxamide | 491.2 |
| 3-23 | (2S,6R)-N-[2-(1-benzylpiperidin-4-yl)ethyl]-4-(5-cyanopyridin-2-yl)-2,6-dimethylpiperazine-1-carboxamide | 461.1 |

Example 4

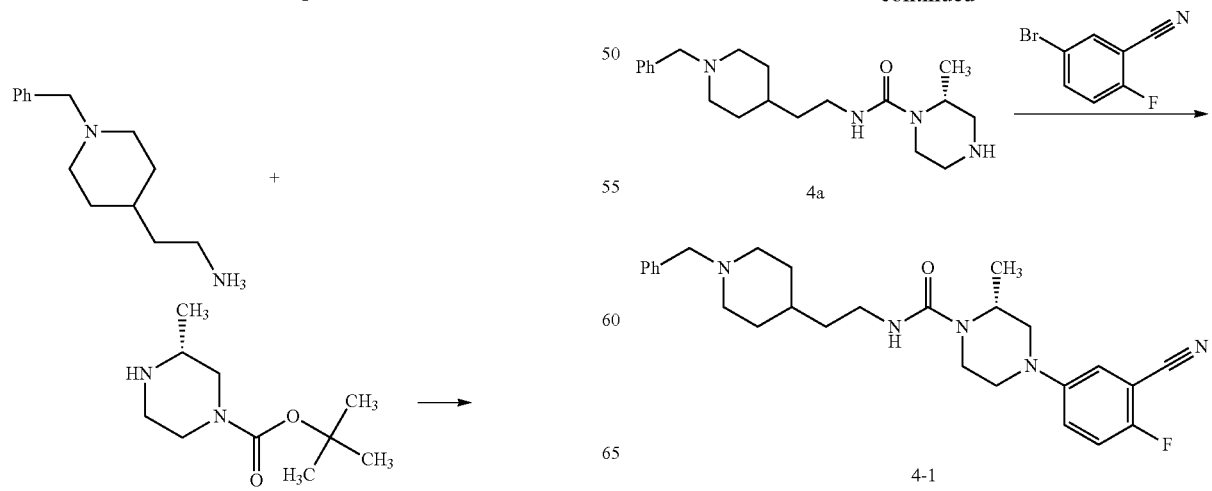

Step 4A: (2R)—N-[2-(1-benzylpiperidin-4-yl)ethyl]-2-methylpiperazine-1-carboxamide Triphosgene (1.2 g, 4.0 mmol, 0.40 eq) was dissolved in methylene chloride (20 mL) and a solution of tert-butyl (3R)-3-methylpiperazine-1-carboxylate (2.0 g, 10 mmol, 1.0 eq) and N,N-diisopropylethylamine (1.6 mL, 10 mmol, 1.0 eq) in methylene chloride (30 mL) was added dropwise at room temperature. Once complete, the reaction mixture was stirred for 10 min before a solution of 2-(1-benzylpiperidin-4-yl)ethan-1-amine (2.6 g, 12 mmol, 1.2 eq) and N,N-diisopropylethylamine (1.6 mL, 10 mmol, 1.0 eq) in methylene chloride (30 mL) was added. Stirring at room temperature, the reaction was complete within 1 hr. The reaction mixture was diluted further with methylene chloride and washed with sat. NH$_4$Cl followed by sat. NaHCO$_3$. The combined organic layers were dried over Na$_2$SO$_4$ and concentrated in vacuo. Silica gel column (40 g) was loaded using methylene chloride and run with an increasing gradient of MeOH (0-25%) in methylene chloride over 20 min. The chromatographed material was dissolved in dioxane (40 mL) and treated with a solution of 4M HCl in dioxane (5 mL). In general, this reaction is completed with stirring overnight, however if necessary, additional acid equivalents and/or gentle heat (50° C.) can be used to push the reaction. The resulting light yellow suspension was concentrated, dissolved in MeOH, and made basic with the addition of MP-carbonate.

Following removal of the resin and concentration of the filtrate, the free base of (2R)—N-[2-(1-benzylpiperidin-4-yl)ethyl]-2-methylpiperazine-1-carboxamide 4a (2.0 g, 5.8 mmol, 58% over two steps) was isolated as a yellow oil. (2S,6R)—N-[2-(1-benzylpiperidin-4-yl)ethyl]-2,6-dimethylpiperazine-1-carboxamide 4b was made according to the same procedure, but with appropriately modified starting materials.

Step 4B: (2R)—N-[2-(1-benzylpiperidin-4-yl)ethyl]-4-(3-cyano-4-fluorophenyl)-2-methylpiperazine-1-carboxamide To a solution of (2R)—N-[2-(1-benzylpiperidin-4-yl)ethyl]-2-methylpiperazine-1-carboxamide 4a (20 mg, 0.06 mmol, 1.0 eq) and 5-bromo-2-fluoro-benzonitrile (12 mg, 0.06 mmol, 1.0 eq) in 1:1 dioxane:toluene (1 mL) was added sodium tert-butoxide (17 mg, 0.18 mmol, 3.0 eq), racemic 2,2'-bis(diphenylphosphino)-1,1'-binaphthyl (3.7 mg, 0.006 mmol, 0.10 eq), and lastly tris(dibenzylideneacetone)-dipalladium(0) (5.5 mg, 0.006 mmol, 0.10 eq), and the reaction mixture stirred vigorously at 100° C. overnight. The resulting dark suspension was cooled, passed through an HPLC filter and concentrated in vacuo. The crude material was treated with 1.5 mL of MeOH, passed through an additional HPLC filter (leaving any precipitate behind), and submitted for directly for preparative chromatography yielding (2R)—N-[2-(1-benzylpiperidin-4-yl)ethyl]-4-(3-cyano-4-fluorophenyl)-2-methylpiperazine-1-carboxamide 4-1. The table below provides the observed (Obs) ion m/z ratio for 4-1 (first compound listed in Table 2) and other compounds that were made according to the procedure as described in this example.

TABLE 2

| Cpd. No. | Compound Name | Obs Ion (m/z) |
|---|---|---|
| 4-1 | (2R)-N-[2-(1-benzylpiperidin-4-yl)ethyl]-4-(3-cyano-4-fluorophenyl)-2-methylpiperazine-1-carboxamide | 464.2 |
| 4-2 | (2R)-N-[2-(1-benzylpiperidin-4-yl)ethyl]-4-(4-methoxypyrimidin-2-yl)-2-methylpiperazine-1-carboxamide | 453.3 |
| 4-4 | (2R)-N-[2-(1-benzylpiperidin-4-yl)ethyl]-4-(4-cyano-3-methylphenyl)-2-methylpiperazine-1-carboxamide | 460.3 |
| 4-5 | (2R)-N-[2-(1-benzylpiperidin-4-yl)ethyl]-2-methyl-4-[4-(trifluoromethyl)phenyl]piperazine-1-carboxamide | 489.2 |
| 4-6 | (2R)-N-[2-(1-benzylpiperidin-4-yl)ethyl]-4-(2,2-difluoro-2H-1,3-benzodioxol-5-yl)-2-methylpiperazine-1-carboxamide | 501.2 |
| 4-8 | (2R)-N-[2-(1-benzylpiperidin-4-yl)ethyl]-4-(3-methoxypyridin-2-yl)-2-methylpiperazine-1-carboxamide | 452.3 |
| 4-9 | (2R)-N-[2-(1-benzylpiperidin-4-yl)ethyl]-2-methyl-4-(6-methylpyridin-3-yl)piperazine-1-carboxamide | 436.3 |
| 4-10 | (2S)-N-[2-(1-benzylpiperidin-4-yl)ethyl]-2-methyl-4-[4-(trifluoromethoxy)phenyl]piperazine-1-carboxamide | 505.2 |
| 4-11 | (2S,6R)-N-[2-(1-benzylpiperidin-4-yl)ethyl]-4-(4-chloro-6-cyanopyrimidin-2-yl)-2,6-dimethylpiperazine-1-carboxamide | 496.2 |
| 4-12 | (2R)-N-[2-(1-benzylpiperidin-4-yl)ethyl]-2-methyl-4-[4-(trifluoromethyl)pyridin-2-yl]piperazine-1-carboxamide | 490.2 |
| 4-13 | (2R)-N-[2-(1-benzylpiperidin-4-yl)ethyl]-4-(3-fluoro-4-methylphenyl)-2-methylpiperazine-1-carboxamide | 453.3 |
| 4-14 | (2S,6R)-N-[2-(1-benzylpiperidin-4-yl)ethyl]-4-(4-cyanopyrimidin-2-yl)-2,6-dimethylpiperazine-1-carboxamide | 462.2 |
| 4-15 | (2R)-N-[2-(1-benzylpiperidin-4-yl)ethyl]-4-(3,4-difluorophenyl)-2-methylpiperazine-1-carboxamide | 457.2 |
| 4-16 | (2R)-N-[2-(1-benzylpiperidin-4-yl)ethyl]-2-methyl-4-[3-(trifluoromethoxy)phenyl]piperazine-1-carboxamide | 505.2 |
| 4-17 | (3R)-N-[2-(1-benzylpiperidin-4-yl)ethyl]-3-methyl-4-(3,4,5-trifluorophenyl)piperazine-1-carboxamide | 475.2 |
| 4-18 | (3R)-N-[2-(1-benzylpiperidin-4-yl)ethyl]-3-methyl-4-[4-(trifluoromethoxy)phenyl]piperazine-1-carboxamide | 505.2 |
| 4-19 | (2R)-N-[2-(1-benzylpiperidin-4-yl)ethyl]-4-(5-fluoro-6-methylpyridin-2-yl)-2-methylpiperazine-1-carboxamide | 454.2 |
| 4-20 | (2S)-N-[2-(1-benzylpiperidin-4-yl)ethyl]-4-(3-cyano-4-fluorophenyl)-2-methylpiperazine-1-carboxamide | 464.2 |
| 4-21 | (2S)-N-[2-(1-benzylpiperidin-4-yl)ethyl]-4-[3-cyano-4-(trifluoromethoxy)phenyl]-2-methylpiperazine-1-carboxamide | 530.2 |

TABLE 2-continued

| Cpd. No. | Compound Name | Obs Ion (m/z) |
|---|---|---|
| 4-22 | (3R)-N-[2-(1-benzylpiperidin-4-yl)ethyl]-4-[3-fluoro-4-(trifluoromethoxy)phenyl]-3-methylpiperazine-1-carboxamide | 523.2 |
| 4-23 | (2R)-N-[2-(1-benzylpiperidin-4-yl)ethyl]-4-(5-cyanopyridin-3-yl)-2-methylpiperazine-1-carboxamide | 447.2 |
| 4-24 | (2S)-N-[2-(1-benzylpiperidin-4-yl)ethyl]-2-methyl-4-(3,4,5-trifluorophenyl)piperazine-1-carboxamide | 475.2 |
| 4-25 | (2R)-N-[2-(1-benzylpiperidin-4-yl)ethyl]-4-(4-cyanophenyl)-2-methylpiperazine-1-carboxamide | 446.2 |
| 4-26 | (2R)-N-[2-(1-benzylpiperidin-4-yl)ethyl]-4-(5-cyano-4-methoxypyrimidin-2-yl)-2-methylpiperazine-1-carboxamide | 478.2 |
| 4-27 | (2R)-N-[2-(1-benzylpiperidin-4-yl)ethyl]-4-(5-fluoro-4-methoxypyrimidin-2-yl)-2-methylpiperazine-1-carboxamide | 471.2 |
| 4-28 | (2R)-N-[2-(1-benzylpiperidin-4-yl)ethyl]-4-[5-cyano-4-(dimethylamino)pyrimidin-2-yl]-2-methylpiperazine-1-carboxamide | 491.4 |
| 4-28 | (2R)-N-[2-(1-benzylpiperidin-4-yl)ethyl]-4-(3-cyano-4-methoxyphenyl)-2-methylpiperazine-1-carboxamide | 476.3 |
| 4-30 | (2R)-N-[2-(1-benzylpiperidin-4-yl)ethyl]-4-(4-fluorophenyl)-2-methylpiperazine-1-carboxamide | 439.2 |
| 4-31 | (2R)-N-[2-(1-benzylpiperidin-4-yl)ethyl]-4-(5-cyanopyridin-2-yl)-2-methylpiperazine-1-carboxamide | 447.2 |
| 4-33 | (2R)-N-[2-(1-benzylpiperidin-4-yl)ethyl]-4-(2,4-difluorophenyl)-2-methylpiperazine-1-carboxamide | 457.2 |
| 4-34 | (2R)-N-[2-(1-benzylpiperidin-4-yl)ethyl]-2-methyl-4-[6-(trifluoromethyl)pyridin-3-yl]piperazine-1-carboxamide | 490.3 |
| 4-35 | (2R)-N-[2-(1-benzylpiperidin-4-yl)ethyl]-4-(6-fluoropyridin-3-yl)-2-methylpiperazine-1-carboxamide | 440.2 |
| 4-36 | (2R)-N-[2-(1-benzylpiperidin-4-yl)ethyl]-2-methyl-4-(2,4,5-trifluorophenyl)piperazine-1-carboxamide | 475.2 |
| 4-37 | (2R)-N-[2-(1-benzylpiperidin-4-yl)ethyl]-4-(2,3-difluorophenyl)-2-methylpiperazine-1-carboxamide | 457.2 |
| 4-38 | (2R)-N-[2-(1-benzylpiperidin-4-yl)ethyl]-4-(4,6-dicyanopyrimidin-2-yl)-2-methylpiperazine-1-carboxamide | 473.2 |
| 4-39 | (2R)-N-[2-(1-benzylpiperidin-4-yl)ethyl]-4-(3-cyano-5-methoxyphenyl)-2-methylpiperazine-1-carboxamide | 476.3 |
| 4-40 | (2R)-N-[2-(1-benzylpiperidin-4-yl)ethyl]-2-methyl-4-(quinolin-3-yl)piperazine-1-carboxamide | 472.3 |
| 4-41 | (2R)-N-[2-(1-benzylpiperidin-4-yl)ethyl]-4-(5-fluoropyrimidin-2-yl)-2-methylpiperazine-1-carboxamide | 441.3 |
| 4-43 | (2R)-N-[2-(1-benzylpiperidin-4-yl)ethyl]-4-(4-cyano-2-fluorophenyl)-2-methylpiperazine-1-carboxamide | 464.3 |
| 4-44 | (2R)-N-[2-(1-benzylpiperidin-4-yl)ethyl]-4-(5-cyanothiophen-2-yl)-2-methylpiperazine-1-carboxamide | 452.2 |
| 4-45 | (2R)-N-[2-(1-benzylpiperidin-4-yl)ethyl]-4-(2,5-difluorophenyl)-2-methylpiperazine-1-carboxamide | 457.2 |
| 4-46 | (2R)-N-[2-(1-benzylpiperidin-4-yl)ethyl]-4-(5-fluoropyridin-2-yl)-2-methylpiperazine-1-carboxamide | 440.2 |
| 4-47 | (2R)-N-[2-(1-benzylpiperidin-4-yl)ethyl]-2-methyl-4-phenylpiperazine-1-carboxamide | 421.3 |
| 4-48 | (2R)-N-[2-(1-benzylpiperidin-4-yl)ethyl]-4-(3,5-difluoropyridin-2-yl)-2-methylpiperazine-1-carboxamide | 458.2 |
| 4-49 | (2R)-N-[2-(1-benzylpiperidin-4-yl)ethyl]-4-(2-fluorophenyl)-2-methylpiperazine-1-carboxamide | 439.2 |
| 4-50 | 2-[(3R)-4-{[2-(1-benzylpiperidin-4-yl)ethyl]carbamoyl}-3-methylpiperazin-1-yl]-6-methyl-N-(propan-2-yl)pyrimidine-4-carboxamide | 522.2 |
| 4-51 | (2R)-N-[2-(1-benzylpiperidin-4-yl)ethyl]-4-(6-methoxypyridin-2-yl)-2-methylpiperazine-1-carboxamide | 452.3 |
| 4-52 | (2R)-N-[2-(1-benzylpiperidin-4-yl)ethyl]-4-(3-chloro-4,5-difluorophenyl)-2-methylpiperazine-1-carboxamide | 491.2 |
| 4-53 | (2S)-N-[2-(1-benzylpiperidin-4-yl)ethyl]-4-[3-fluoro-4-(trifluoromethoxy)phenyl]-2-methylpiperazine-1-carboxamide | 523.2 |
| 4-54 | (2S,6R)-4-(4-amino-5-cyanopyrimidin-2-yl)-N-[2-(1-benzylpiperidin-4-yl)ethyl]-2,6-dimethylpiperazine-1-carboxamide | 477.3 |
| 4-55 | (2R)-N-[2-(1-benzylpiperidin-4-yl)ethyl]-4-(4-cyano-5-fluoropyrimidin-2-yl)-2-methylpiperazine-1-carboxamide | 466.2 |
| 4-56 | N-[2-(1-benzylpiperidin-4-yl)ethyl]-4-(4-methoxyphenyl)-3-methylpiperazine-1-carboxamide | 451.3 |
| 4-60 | (2R)-N-[2-(1-benzylpiperidin-4-yl)ethyl]-4-[3,5-difluoro-4-(trifluoromethoxy)phenyl]-2-methylpiperazine-1-carboxamide | 541.2 |
| 4-61 | (2R)-N-[2-(1-benzylpiperidin-4-yl)ethyl]-4-(5-fluoropyridin-3-yl)-2-methylpiperazine-1-carboxamide | 440.2 |
| 4-62 | (2R)-N-[2-(1-benzylpiperidin-4-yl)ethyl]-2-methyl-4-(pyridin-2-yl)piperazine-1-carboxamide | 422.2 |
| 4-63 | (2R)-N-[2-(1-benzylpiperidin-4-yl)ethyl]-2-methyl-4-(5-methylpyridin-3-yl)piperazine-1-carboxamide | 436.3 |
| 4-64 | (2R)-N-[2-(1-benzylpiperidin-4-yl)ethyl]-2-methyl-4-(pyrimidin-2-yl)piperazine-1-carboxamide | 423.2 |

TABLE 2-continued

| Cpd. No. | Compound Name | Obs Ion (m/z) |
|---|---|---|
| 4-68 | (2R)-N-[2-(1-benzylpiperidin-4-yl)ethyl]-4-(3-cyanophenyl)-2-methylpiperazine-1-carboxamide | 446.2 |
| 4-69 | (2R,6S)-N-[2-(1-benzylpiperidin-4-yl)ethyl]-4-(5-cyano-4-methoxypyrimidin-2-yl)-2,6-dimethylpiperazine-1-carboxamide | 492.2 |
| 4-70 | (2R)-N-[2-(1-benzylpiperidin-4-yl)ethyl]-4-(3-fluoro-4-methoxyphenyl)-2-methylpiperazine-1-carboxamide | 469.3 |
| 4-71 | (3S)-N-[2-(1-benzylpiperidin-4-yl)ethyl]-3-methyl-4-(3,4,5-trifluorophenyl)piperazine-1-carboxamide | 475.2 |
| 4-72 | (2R)-N-[2-(1-benzylpiperidin-4-yl)ethyl]-4-(3,5-difluorophenyl)-2-methylpiperazine-1-carboxamide | 457.25 |
| 4-73 | (2R)-N-[2-(1-benzylpiperidin-4-yl)ethyl]-4-[2-fluoro-4-(trifluoromethyl)phenyl]-2-methylpiperazine-1-carboxamide | 507.2 |
| 4-74 | N-[2-(1-benzylpiperidin-4-yl)ethyl]-4-(3,4,5-trifluorophenyl)piperazine-1-carboxamide | 461.3 |
| 4-75 | (2R)-N-[2-(1-benzylpiperidin-4-yl)ethyl]-4-(4,6-dicyanopyrimidin-2-yl)-2-methylpiperazine-1-carboxamide | 473.2 |
| 4-76 | N-[2-(1-benzylpiperidin-4-yl)ethyl]-4-[4-(trifluoromethyl)phenyl]piperazine-1-carboxamide | 475.2 |
| 4-77 | N-[2-(1-benzylpiperidin-4-yl)ethyl]-4-[5-(trifluoromethyl)pyridin-2-yl]piperazine-1-carboxamide | 476.1 |
| 4-78 | (2S,6R)-N-[2-(1-benzylpiperidin-4-yl)ethyl]-4-(5-cyano-3-fluoropyridin-2-yl)-2,6-dimethylpiperazine-1-carboxamide | 479.2 |
| 4-79 | (2R)-N-[2-(1-benzylpiperidin-4-yl)ethyl]-2-methyl-4-[2-(trifluoromethyl)pyrimidin-5-yl]piperazine-1-carboxamide | 491.17 |
| 4-80 | (2R)-N-[2-(1-benzylpiperidin-4-yl)ethyl]-4-(2-cyanopyrimidin-5-yl)-2-methylpiperazine-1-carboxamide | 448.15 |

Example 5

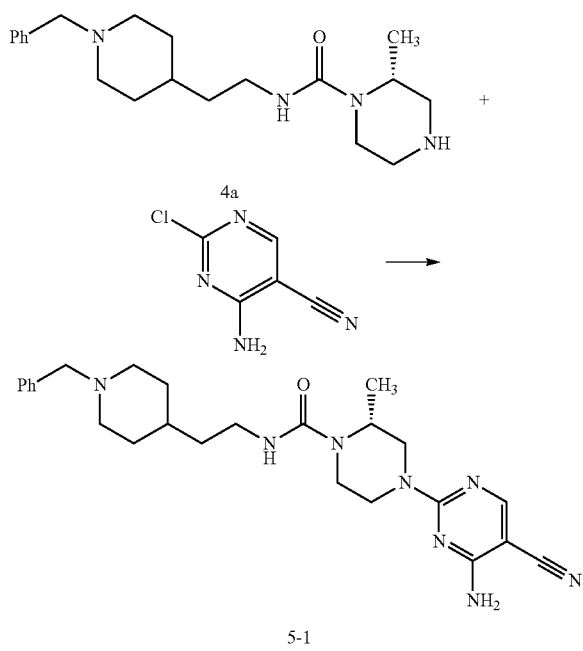

Step 5A: (2R)-4-(4-amino-5-cyanopyrimidin-2-yl)-N-[2-(1-benzylpiperidin-4-yl)ethyl]-2-methylpiperazine-1-carboxamide To a solution of (2R)—N-[2-(1-benzylpiperidin-4-yl)ethyl]-2-methylpiperazine-1-carboxamide 4a (0.20 g, 0.58 mmol, 1.0 eq) and 4-amino-2-chloropyrimidine-5-carbonitrile (0.90 g, 0.58 mmol, 1.0 eq) in NMP (2 mL) was added N,N-diisopropylethylamine (0.38 mL, 2.3 mmol, 4.0 eq) and the reaction mixture heated to 100° C. for 1 hr. In some cases, lower temperatures or longer reaction times were used. The reaction mixture was cooled, diluted heavily with EtOAc, and washed repeatedly with brine (3×). The organic layer was dried over $Na_2SO_4$ and concentrated. Silica gel column (24 g) was loaded using methylene chloride and run using an increasing gradient of MeOH (0-20%) in methylene chloride over 20 min to provide (2R)-4-(4-amino-5-cyanopyrimidin-2-yl)-N-[2-(1-benzylpiperidin-4-yl)ethyl]-2-methylpiperazine-1-carboxamide 5-1 (0.14 g, 0.31 mmol, 53%) as an off-white foam. The table below provides the observed (Obs) ion m/z ratio for 5-1 (first compound listed in Table 3) and other compounds that were made according to the procedure as described in this example.

TABLE 3

| Cpd. No. | Compound Name | Obs Ion (m/z) |
|---|---|---|
| 5-1 | (2R)-4-(4-amino-5-cyanopyrimidin-2-yl)-N-[2-(1-benzylpiperidin-4-yl)ethyl]-2-methylpiperazine-1-carboxamide | 463.2 |
| 5-2 | 2-[(3R)-4-{[2-(1-benzylpiperidin-4-yl)ethyl]carbamoyl}-3-methylpiperazin-1-yl]pyrimidine-5-carboxylic acid | 467.2 |

TABLE 3-continued

| Cpd. No. | Compound Name | Obs Ion (m/z) |
| --- | --- | --- |
| 5-3 | (2R)-N-[2-(1-benzylpiperidin-4-yl)ethyl]-4-(4,5-dichloropyrimidin-2-yl)-2-methylpiperazine-1-carboxamide | 491.1 |
| 5-4 | (2S,6R)-N-[2-(1-benzylpiperidin-4-yl)ethyl]-4-{5-cyano-4-[(2,2,2-trifluoroethyl)amino]pyrimidin-2-yl}-2,6-dimethylpiperazine-1-carboxamide | 559.2 |
| 5-5 | (2R)-N-[2-(1-benzylpiperidin-4-yl)ethyl]-4-(4-chloro-6-cyanopyrimidin-2-yl)-2-methylpiperazine-1-carboxamide | 482.2 |
| 5-6 | (2R)-N-[2-(1-benzylpiperidin-4-yl)ethyl]-2-methyl-4-(trifluoropyrimidin-2-yl)piperazine-1-carboxamide | 477.2 |
| 5-7 | (2R)-N-[2-(1-benzylpiperidin-4-yl)ethyl]-4-{5-cyano-4-[(2,2,2-trifluoroethyl)amino]pyrimidin-2-yl}-2-methylpiperazine-1-carboxamide | 545.2 |
| 5-8 | (2R)-N-[2-(1-benzylpiperidin-4-yl)ethyl]-2-methyl-4-[4-(trifluoromethyl)pyrimidin-2-yl]piperazine-1-carboxamide | 491.2 |
| 5-9 | (2R)-N-[2-(1-benzylpiperidin-4-yl)ethyl]-4-(4-chloro-5-fluoropyrimidin-2-yl)-2-methylpiperazine-1-carboxamide | 475.2 |
| 5-10 | (2R)-N-[2-(1-benzylpiperidin-4-yl)ethyl]-4-(5-bromo-4-chloropyrimidin-2-yl)-2-methylpiperazine-1-carboxamide | 537.1 |
| 5-11 | methyl 2-[(3R)-4-{[2-(1-benzylpiperidin-4-yl)ethyl]carbamoyl}-3-methylpiperazin-1-yl]-6-chloropyrimidine-4-carboxylate | 515.1 |
| 5-12 | methyl 2-[(3R)-4-{[2-(1-benzylpiperidin-4-yl)ethyl]carbamoyl}-3-methylpiperazin-1-yl]-6-methylpyrimidine-4-carboxylate | 495.2 |
| 5-13 | (2R)-N-[2-(1-benzylpiperidin-4-yl)ethyl]-4-(5-cyanopyrimidin-2-yl)-2-methylpiperazine-1-carboxamide | 448.3 |
| 5-14 | (2S,6R)-4-(4-amino-5-cyanopyrimidin-2-yl)-N-[2-(1-benzylpiperidin-4-yl)ethyl]-2,6-dimethylpiperazine-1-carboxamide | 477.3 |
| 5-15 | (2R)-N-[2-(1-benzylpiperidin-4-yl)ethyl]-4-[5-cyano-4-(dimethylamino)pyrimidin-2-yl]-2-methylpiperazine-1-carboxamide | 491.4 |
| 5-16 | (2R)-N-[2-(1-benzylpiperidin-4-yl)ethyl]-4-(5-cyano-4-methoxypyrimidin-2-yl)-2-methylpiperazine-1-carboxamide | 478.2 |
| 5-17 | (2R,6S)-N-[2-(1-benzylpiperidin-4-yl)ethyl]-4-(5-cyano-4-methoxypyrimidin-2-yl)-2,6-dimethylpiperazine-1-carboxamide | 492.2 |
| 5-18 | (2S,6R)-N-[2-(1-benzylpiperidin-4-yl)ethyl]-4-(5-chloropyrimidin-2-yl)-2,6-dimethylpiperazine-1-carboxamide | 471.2 |
| 5-19 | (2S,6R)-N-[2-(1-benzylpiperidin-4-yl)ethyl]-4-(5-fluoropyrimidin-2-yl)-2,6-dimethylpiperazine-1-carboxamide | 455.25 |
| 5-20 | (2S,6R)-N-[2-(1-benzylpiperidin-4-yl)ethyl]-4-(5-cyanopyrimidin-2-yl)-2,6-dimethylpiperazine-1-carboxamide | 462.3 |
| 5-21 | (2R,6S)-N-[2-(1-benzylpiperidin-4-yl)ethyl]-4-[5-cyano-4-(methylamino)pyrimidin-2-yl]-2,6-dimethylpiperazine-1-carboxamide | 491.3 |
| 5-22 | (2R)-N-[2-(1-benzylpiperidin-4-yl)ethyl]-4-(5-chloropyrimidin-2-yl)-2-methylpiperazine-1-carboxamide | 457.2 |
| 5-23 | (2R)-N-[2-(1-benzylpiperidin-4-yl)ethyl]-4-[5-cyano-4-(methylamino)pyrimidin-2-yl]-2-methylpiperazine-1-carboxamide | 477.2 |
| 5-24 | N-[2-(1-benzylpiperidin-4-yl)ethyl]-4-[5-(trifluoromethyl)pyrimidin-2-yl]piperazine-1-carboxamide | 477.15 |
| 5-25 | (3S)-N-[2-(1-benzylpiperidin-4-yl)ethyl]-4-(5-cyanopyrimidin-2-yl)-3-(hydroxymethyl)piperazine-1-carboxamide | 464.2 |
| 5-26 | (2R)-N-[2-(1-benzylpiperidin-4-yl)ethyl]-4-(5-cyanopyrimidin-2-yl)-2-(hydroxymethyl)piperazine-1-carboxamide | 464.2 |
| 5-27 | (2R,6S)-N-[2-(1-benzylpiperidin-4-yl)ethyl]-2,6-dimethyl-4-[5-(trifluoromethyl)pyrimidin-2-yl]piperazine-1-carboxamide | 505.1 |
| 5-28 | (2R,6S)-4-[4-amino-5-(trifluoromethyl)pyrimidin-2-yl]-N-[2-(1-benzylpiperidin-4-yl)ethyl]-2,6-dimethylpiperazine-1-carboxamide | 520.1 |
| 5-29 | (2R)-4-[4-amino-5-(trifluoromethyl)pyrimidin-2-yl]-N-[2-(1-benzylpiperidin-4-yl)ethyl]-2-methylpiperazine-1-carboxamide | 506.1 |
| 5-30 | 4-[4-amino-5-(trifluoromethyl)pyrimidin-2-yl]-N-[2-(1-benzylpiperidin-4-yl)ethyl]piperazine-1-carboxamide | 492.1 |
| 5-31 | (2R)-N-[2-(1-benzylpiperidin-4-yl)ethyl]-4-(5-bromopyrimidin-2-yl)-2-methylpiperazine-1-carboxamide | 501.2 |
| 5-32 | (2R)-4-(4-amino-5-chloropyrimidin-2-yl)-N-[2-(1-benzylpiperidin-4-yl)ethyl]-2-methylpiperazine-1-carboxamide | 472.0 |
| 5-33 | 4-(4-amino-5-chloropyrimidin-2-yl)-N-[2-(1-benzylpiperidin-4-yl)ethyl]piperazine-1-carboxamide | 458.0 |
| 5-34 | 4-(4-amino-5-fluoropyrimidin-2-yl)-N-[2-(1-benzylpiperidin-4-yl)ethyl]piperazine-1-carboxamide | 442.0 |

Example 6

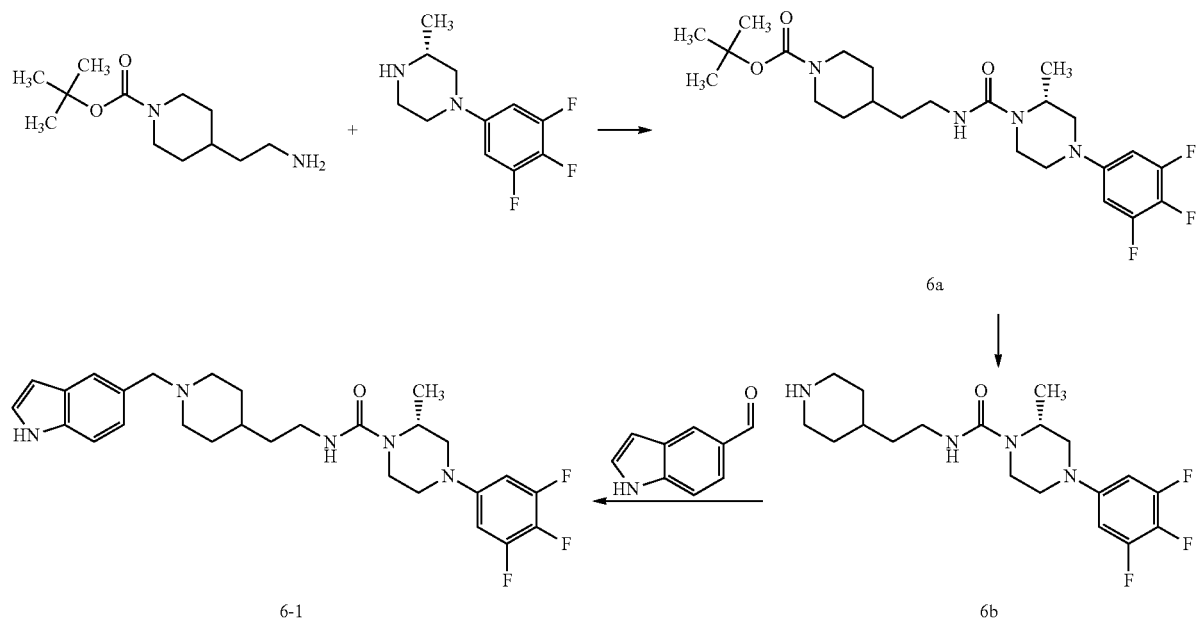

Step 6A: (2R)-2-methyl-N-[2-(piperidin-4-yl)ethyl]-4-(3,4,5-trifluorophenyl)piperazine-1-carboxamide Triphosgene (1.3 g, 4.4 mmol, 0.40 eq) was dissolved in methylene chloride (30 mL) and a solution of (3R)-3-methyl-1-(3,4,5-trifluorophenyl)piperazine 1I (2.5 g, 11 mmol, 1.0 eq) and N,N-diisopropylethylamine (3.6 mL, 22 mmol, 2.0 eq) in methylene chloride (30 mL) was added dropwise at room temperature. Once the addition was complete, the reaction mixture was stirred for 10 min before a solution of tert-butyl 4-(2-aminoethyl)piperidine-1-carboxylate (2.9 g, 13 mmol, 1.2 eq) and N,N-diisopropylethylamine (3.6 mL, 22 mmol, 2.0 eq) in methylene chloride (30 mL) was added. Stirring at room temperature, the reaction was complete within 1 hr. The reaction mixture was diluted further with methylene chloride and washed with sat. NH₄Cl followed by sat. NaHCO₃. The combined organic layers were dried over Na₂SO₄, concentrated in vacuo, and loaded onto a silica gel column (40 g). Elution with an increasing gradient of EtOAc (0-100%) in hexanes over 25 min yielded tert-butyl 4-(2-{[(2R)-2-methyl-4-(3,4,5-trifluorophenyl)piperazine-1-carbonyl]amino}ethyl)piperidine-1-carboxylate 6a. This chromatographed material was dissolved in dioxane (60 mL) and treated with a solution of 4M HCl in dioxane (10 mL). After stirring overnight, the resulting light yellow suspension was concentrated, dissolved in MeOH, and made basic with the addition of MP-carbonate.

Following removal of the resin and concentration of the filtrate, the free base of (2R)-2-methyl-N-[2-(piperidin-4-yl)ethyl]-4-(3,4,5-trifluorophenyl)piperazine-1-carboxamide 6b (2.2 g, 5.8 mmol, 53% over two steps) was isolated as a brown foam. (2S,6R)-4-(5-cyanopyrimidin-2-yl)-2,6-dimethyl-N-[2-(piperidin-4-yl)ethyl]piperazine-1-carboxamide 6c was made according to the same procedure, but with appropriately modified starting materials.

Step 6B: (2R)—N-{2-[1-(1H-indol-5-ylmethyl)piperidin-4-yl]ethyl}-2-methyl-4-(3,4,5-trifluorophenyl)piperazine-1-carboxamide To NMP solutions of (2R)-2-methyl-N-[2-(piperidin-4-yl)ethyl]-4-(3,4,5-trifluorophenyl)piperazine-1-carboxamide 6b (0.05 mL, 0.50 M, 1 eq) and 1H-indole-5-carbaldehyde (0.05 mL, 0.50 M, 1 eq) was added an ethanolic solution of borane-pyridine complex (0.10 mL, 0.50 M, 2 eq) followed by acetic acid (5 µL) and the mixture stirred at RT overnight. The reaction mixture was diluted to a total volume of 1 mL using MeOH and submitted directly for preparative chromatography yielding (2R)—N-{2-[1-(1H-indol-5-ylmethyl)piperidin-4-yl]ethyl}-2-methyl-4-(3,4,5-trifluorophenyl)piperazine-1-carboxamide 6-1. The table below provides the observed (Obs) ion m/z ratio for 6-1 (first compound listed in Table 4) and other compounds that were made according to the procedure as described in this example.

TABLE 4

| Cpd. No. | Compound Name | Obs Ion (m/z) |
|---|---|---|
| 6-1 | (2R)-N-{2-[1-(1H-indol-5-ylmethyl)piperidin-4-yl]ethyl}-2-methyl-4-(3,4,5-trifluorophenyl)piperazine-1-carboxamide | 514.2 |
| 6-2 | (2R)-N-(2-{1-[(4-cyanophenyl)methyl]piperidin-4-yl}ethyl)-2-methyl-4-(3,4,5-trifluorophenyl)piperazine-1-carboxamide | 500.2 |
| 6-3 | (2R)-N-{2-[1-(2,3-dihydro-1-benzofuran-7-ylmethyl)piperidin-4-yl]ethyl}-2-methyl-4-(3,4,5-trifluorophenyl)piperazine-1-carboxamide | 517.2 |

TABLE 4-continued

| Cpd. No. | Compound Name | Obs Ion (m/z) |
|---|---|---|
| 6-4 | (2R)-N-(2-{1-[(4-fluorophenyl)methyl]piperidin-4-yl}ethyl)-2-methyl-4-(3,4,5-trifluorophenyl)piperazine-1-carboxamide | 493.2 |
| 6-5 | (2R)-N-(2-{1-[(2-fluorophenyl)methyl]piperidin-4-yl}ethyl)-2-methyl-4-(3,4,5-trifluorophenyl)piperazine-1-carboxamide | 493.2 |
| 6-6 | (2R)-N-{2-[1-(cyclohexylmethyl)piperidin-4-yl]ethyl}-2-methyl-4-(3,4,5-trifluorophenyl)piperazine-1-carboxamide | 481.3 |
| 6-7 | (2R)-2-methyl-N-{2-[1-(pyridin-2-ylmethyl)piperidin-4-yl]ethyl}-4-(3,4,5-trifluorophenyl)piperazine-1-carboxamide | 476.2 |
| 6-8 | (2R)-2-methyl-N-{2-[1-(1,2,3-thiadiazol-4-ylmethyl)piperidin-4-yl]ethyl}-4-(3,4,5-trifluorophenyl)piperazine-1-carboxamide | 483.2 |
| 6-9 | (2R)-N-{2-[1-(2,3-dihydro-1,4-benzodioxin-6-ylmethyl)piperidin-4-yl]ethyl}-2-methyl-4-(3,4,5-trifluorophenyl)piperazine-1-carboxamide | 533.2 |
| 6-10 | (2R)-N-(2-{1-[(3-fluorophenyl)methyl]piperidin-4-yl}ethyl)-2-methyl-4-(3,4,5-trifluorophenyl)piperazine-1-carboxamide | 493.2 |
| 6-11 | 1-(5-cyanopyridin-2-yl)-N-{2-[1-(1H-indol-5-ylmethyl)piperidin-4-yl]ethyl}piperidine-4-carboxamide | 471.3 |
| 6-12 | (2R)-2-methyl-N-(2-{1-[(2-methyl-1,3-thiazol-4-yl)methyl]piperidin-4-yl}ethyl)-4-(3,4,5-trifluorophenyl)piperazine-1-carboxamide | 496.2 |
| 6-13 | (2R)-N-[2-(1-{[2-(difluoromethoxy)phenyl]methyl}piperidin-4-yl)ethyl]-2-methyl-4-(3,4,5-trifluorophenyl)piperazine-1-carboxamide | 541.2 |
| 6-14 | (2R)-2-methyl-N-{2-[1-(1-phenylethyl)piperidin-4-yl]ethyl}-4-(3,4,5-trifluorophenyl)piperazine-1-carboxamide | 489.2 |
| 6-15 | 4-(benzyloxy)-N-(2-{1-[(4-fluorophenyl)methyl]piperidin-4-yl}ethyl)benzamide | 447.6 |
| 6-16 | (2R)-N-(2-{1-[(4-carbamoylphenyl)methyl]piperidin-4-yl}ethyl)-2-methyl-4-(3,4,5-trifluorophenyl)piperazine-1-carboxamide | 518.17 |
| 6-17 | (2R)-N-(2-{1-[(2,3-difluorophenyl)methyl]piperidin-4-yl}ethyl)-2-methyl-4-(3,4,5-trifluorophenyl)piperazine-1-carboxamide | 511.2 |
| 6-18 | (2R)-N-(2-{1-[(3-cyanophenyl)methyl]piperidin-4-yl}ethyl)-2-methyl-4-(3,4,5-trifluorophenyl)piperazine-1-carboxamide | 500.2 |
| 6-19 | (2R)-2-methyl-N-(2-{1-[(5-methyl-1,3,4-oxadiazol-2-yl)(phenyl)methyl]piperidin-4-yl}ethyl)-4-(3,4,5-trifluorophenyl)piperazine-1-carboxamide | 557.2 |
| 6-20 | (2R)-2-methyl-N-[2-(1-{[3-(trifluoromethoxy)phenyl]methyl}piperidin-4-yl)ethyl]-4-(3,4,5-trifluorophenyl)piperazine-1-carboxamide | 559.2 |
| 6-21 | (2R)-2-methyl-N-[2-(1-{[2-(trifluoromethoxy)phenyl]methyl}piperidin-4-yl)ethyl]-4-(3,4,5-trifluorophenyl)piperazine-1-carboxamide | 559.2 |
| 6-22 | (2R)-2-methyl-4-(3,4,5-trifluorophenyl)-N-(2-{1-[(2,3,4-trifluorophenyl)methyl]piperidin-4-yl}ethyl)piperazine-1-carboxamide | 529.1 |
| 6-23 | (2R)-N-(2-{1-[(3,5-difluorophenyl)methyl]piperidin-4-yl}ethyl)-2-methyl-4-(3,4,5-trifluorophenyl)piperazine-1-carboxamide | 511.2 |
| 6-24 | (2R)-2-methyl-N-[2-(1-{[4-(trifluoromethoxy)phenyl]methyl}piperidin-4-yl)ethyl]-4-(3,4,5-trifluorophenyl)piperazine-1-carboxamide | 559.2 |
| 6-25 | (2R)-N-(2-{1-[(2,5-difluorophenyl)methyl]piperidin-4-yl}ethyl)-2-methyl-4-(3,4,5-trifluorophenyl)piperazine-1-carboxamide | 511.2 |
| 6-26 | (2R)-2-methyl-N-{2-[1-(thiophen-2-ylmethyl)piperidin-4-yl]ethyl}-4-(3,4,5-trifluorophenyl)piperazine-1-carboxamide | 481.2 |
| 6-27 | (2R)-N-(2-{1-[(4-hydroxyphenyl)methyl]piperidin-4-yl}ethyl)-2-methyl-4-(3,4,5-trifluorophenyl)piperazine-1-carboxamide | 491.2 |
| 6-28 | (2R)-N-(2-{1-[(2,6-difluorophenyl)methyl]piperidin-4-yl}ethyl)-2-methyl-4-(3,4,5-trifluorophenyl)piperazine-1-carboxamide | 511.2 |
| 6-29 | (2R)-N-(2-{1-[(2-cyanophenyl)methyl]piperidin-4-yl}ethyl)-2-methyl-4-(3,4,5-trifluorophenyl)piperazine-1-carboxamide | 500.2 |
| 6-30 | (2R)-N-(2-{1-[(4-cyano-2-fluorophenyl)methyl]piperidin-4-yl}ethyl)-2-methyl-4-(3,4,5-trifluorophenyl)piperazine-1-carboxamide | 518.1 |
| 6-31 | (2R)-2-methyl-N-{2-[1-(pyridin-4-ylmethyl)piperidin-4-yl]ethyl}-4-[5-(trifluoromethyl)pyrimidin-2-yl]piperazine-1-carboxamide | 492.2 |
| 6-32 | (2R)-2-methyl-N-{2-[1-(pyridin-3-ylmethyl)piperidin-4-yl]ethyl}-4-[5-(trifluoromethyl)pyrimidin-2-yl]piperazine-1-carboxamide | 492.2 |
| 6-33 | (2R)-2-methyl-N-{2-[1-(pyridin-2-ylmethyl)piperidin-4-yl]ethyl}-4-[5-(trifluoromethyl)pyrimidin-2-yl]piperazine-1-carboxamide | 492.2 |
| 6-34 | (2R)-N-(2-{1-[(2-cyanophenyl)methyl]piperidin-4-yl}ethyl)-2-methyl-4-[5-(trifluoromethyl)pyrimidin-2-yl]piperazine-1-carboxamide | 516.1 |
| 6-35 | (2R)-2-methyl-N-(2-{1-[(2-methylphenyl)methyl]piperidin-4-yl}ethyl)-4-[5-(trifluoromethyl)pyrimidin-2-yl]piperazine-1-carboxamide | 505.2 |

TABLE 4-continued

| Cpd. No. | Compound Name | Obs Ion (m/z) |
|---|---|---|
| 6-36 | (2R)-N-(2-{1-[(3-fluorophenyl)methyl]piperidin-4-yl}ethyl)-2-methyl-4-[5-(trifluoromethyl)pyrimidin-2-yl]piperazine-1-carboxamide | 509.1 |
| 6-37 | (2R)-N-(2-{1-[(4-fluorophenyl)methyl]piperidin-4-yl}ethyl)-2-methyl-4-[5-(trifluoromethyl)pyrimidin-2-yl]piperazine-1-carboxamide | 509.1 |
| 6-38 | (2R)-N-(2-{1-[(2-fluorophenyl)methyl]piperidin-4-yl}ethyl)-2-methyl-4-[5-(trifluoromethyl)pyrimidin-2-yl]piperazine-1-carboxamide | 509.2 |
| 6-39 | (2R)-2-methyl-N-{2-[1-(pyrimidin-5-ylmethyl)piperidin-4-yl]ethyl}-4-[5-(trifluoromethyl)pyrimidin-2-yl]piperazine-1-carboxamide | 492.3 |
| 6-40 | (2R)-N-(2-{1-[(3-cyanophenyl)methyl]piperidin-4-yl}ethyl)-2-methyl-4-[5-(trifluoromethyl)pyrimidin-2-yl]piperazine-1-carboxamide | 516.1 |
| 6-41 | (2R)-N-(2-{1-[(4-cyanophenyl)methyl]piperidin-4-yl}ethyl)-2-methyl-4-[5-(trifluoromethyl)pyrimidin-2-yl]piperazine-1-carboxamide | 516.1 |
| 6-42 | (2R,6S)-4-(5-cyanopyrimidin-2-yl)-N-(2-{1-[(4-hydroxyphenyl)methyl]piperidin-4-yl}ethyl)-2,6-dimethylpiperazine-1-carboxamide | 478.1 |
| 6-43 | (2R,6S)-4-(5-cyanopyrimidin-2-yl)-N-[2-(1-{[4-(dimethylamino)phenyl]methyl}piperidin-4-yl)ethyl]-2,6-dimethylpiperazine-1-carboxamide | 505.1 |
| 6-44 | (2R,6S)-4-(5-cyanopyrimidin-2-yl)-2,6-dimethyl-N-{2-[1-(2-phenylethyl)piperidin-4-yl]ethyl}piperazine-1-carboxamide | 476.0 |
| 6-45 | (2R,6S)-N-(2-{1-[(4-cyanophenyl)methyl]piperidin-4-yl}ethyl)-4-(5-cyanopyrimidin-2-yl)-2,6-dimethylpiperazine-1-carboxamide | 487.0 |
| 6-46 | (2R,6S)-4-(5-cyanopyrimidin-2-yl)-N-(2-{1-[(3-fluorophenyl)methyl]piperidin-4-yl}ethyl)-2,6-dimethylpiperazine-1-carboxamide | 480.1 |
| 6-47 | (2R,6S)-4-(5-cyanopyrimidin-2-yl)-N-(2-{1-[(1H-indol-5-ylmethyl)-piperidin-4-yl]ethyl}-2,6-dimethylpiperazine-1-carboxamide | 501.0 |
| 6-48 | (2R,6S)-4-(5-cyanopyrimidin-2-yl)-N-(2-{1-[(4-fluorophenyl)methyl]-piperidin-4-yl}ethyl)-2,6-dimethylpiperazine-1-carboxamide | 480.0 |
| 6-49 | (2R,6S)-N-(2-{1-[(4-hydroxy-3-methylphenyl)methyl]piperidin-4-yl}ethyl)-2,6-dimethyl-4-[2-(trifluoromethyl)pyrimidin-5-yl]piperazine-1-carboxamide | 535.1 |
| 6-50 | (2R,6S)-N-{2-[1-(1H-indol-5-ylmethyl)piperidin-4-yl]ethyl}-2,6-dimethyl-4-[2-(trifluoromethyl)pyrimidin-5-yl]piperazine-1-carboxamide | 544.1 |
| 6-51 | (2R,6S)-N-(2-{1-[(3-fluorophenyl)methyl]piperidin-4-yl}ethyl)-2,6-dimethyl-4-[2-(trifluoromethyl)pyrimidin-5-yl]piperazine-1-carboxamide | 523.1 |
| 6-52 | (2R,6S)-N-(2-{1-[(2-fluorophenyl)methyl]piperidin-4-yl}ethyl)-2,6-dimethyl-4-[2-(trifluoromethyl)pyrimidin-5-yl]piperazine-1-carboxamide | 523.0 |
| 6-53 | (2R,6S)-N-[2-(1-{[4-(dimethylamino)phenyl]methyl}piperidin-4-yl)ethyl]-2,6-dimethyl-4-[2-(trifluoromethyl)pyrimidin-5-yl]piperazine-1-carboxamide | 548.1 |
| 6-54 | (2R,6S)-N-(2-{1-[(4-hydroxyphenyl)methyl]piperidin-4-yl}ethyl)-2,6-dimethyl-4-[2-(trifluoromethyl)pyrimidin-5-yl]piperazine-1-carboxamide | 521.1 |
| 6-55 | (2R,6S)-N-(2-{1-[(4-fluorophenyl)methyl]piperidin-4-yl}ethyl)-2,6-dimethyl-4-[2-(trifluoromethyl)pyrimidin-5-yl]piperazine-1-carboxamide | 523.1 |
| 6-56 | (2R,6S)-2,6-dimethyl-N-{2-[1-(2-phenylethyl)piperidin-4-yl]ethyl}-4-[2-(trifluoromethyl)pyrimidin-5-yl]piperazine-1-carboxamide | 519.1 |
| 6-57 | (2R,6S)-4-(5-cyanopyrimidin-2-yl)-N-(2-{1-[(4-hydroxy-3-methylphenyl)methyl]piperidin-4-yl}ethyl)-2,6-dimethylpiperazine-1-carboxamide | 492.0 |
| 6-58 | (2R,6S)-4-(5-cyanopyrimidin-2-yl)-2,6-dimethyl-N-{2-[1-(pyrimidin-2-ylmethyl)piperidin-4-yl]ethyl}piperazine-1-carboxamide | 464.1 |
| 6-59 | (2R,6S)-4-(5-cyanopyrimidin-2-yl)-N-(2-{1-[(3-methoxyphenyl)methyl]piperidin-4-yl}ethyl)-2,6-dimethylpiperazine-1-carboxamide | 492.1 |
| 6-60 | (2R,6S)-N-{2-[1-(1-benzofuran-5-ylmethyl)piperidin-4-yl]ethyl}-4-(5-cyanopyrimidin-2-yl)-2,6-dimethylpiperazine-1-carboxamide | 502.0 |
| 6-61 | (2R,6S)-4-(5-cyanopyrimidin-2-yl)-2,6-dimethyl-N-{2-[1-(pyridin-3-ylmethyl)piperidin-4-yl]ethyl}piperazine-1-carboxamide | 463.1 |

TABLE 4-continued

| Cpd. No. | Compound Name | Obs Ion (m/z) |
|---|---|---|
| 6-62 | (2R,6S)-4-(5-cyanopyrimidin-2-yl)-2,6-dimethyl-N-{2-[1-(pyridin-4-ylmethyl)piperidin-4-yl]ethyl}piperazine-1-carboxamide | 463.1 |
| 6-63 | (4-{[4-(2-{[(2R,6S)-4-(5-cyanopyrimidin-2-yl)-2,6-dimethyl-piperazine-1-carbonyl]amino}ethyl)piperidin-1-yl]methyl}phenyl)boronic acid | 506.1 |
| 6-64 | (2R,6S)-4-(5-cyanopyrimidin-2-yl)-N-(2-{1-[(2-fluoropyridin-3-yl)methyl]piperidin-4-yl}ethyl)-2,6-dimethylpiperazine-1-carboxamide | 481.1 |
| 6-65 | (2R,6S)-4-(5-cyanopyrimidin-2-yl)-N-(2-{1-[(4-methoxyphenyl)-methyl]piperidin-4-yl}ethyl)-2,6-dimethylpiperazine-1-carboxamide | 492.1 |
| 6-66 | (2R,6S)-4-(5-cyanopyrimidin-2-yl)-2,6-dimethyl-N-(2-{1-[(1-methyl-1H-1,2,3-benzotriazol-5-yl)methyl]piperidin-4-yl}ethyl)piperazine-1-carboxamide | 517.0 |
| 6-67 | (2R,6S)-4-(5-cyanopyrimidin-2-yl)-N-(2-{1-[(2-methoxyphenyl)-methyl]piperidin-4-yl}ethyl)-2,6-dimethylpiperazine-1-carboxamide | 492.0 |

Example 7

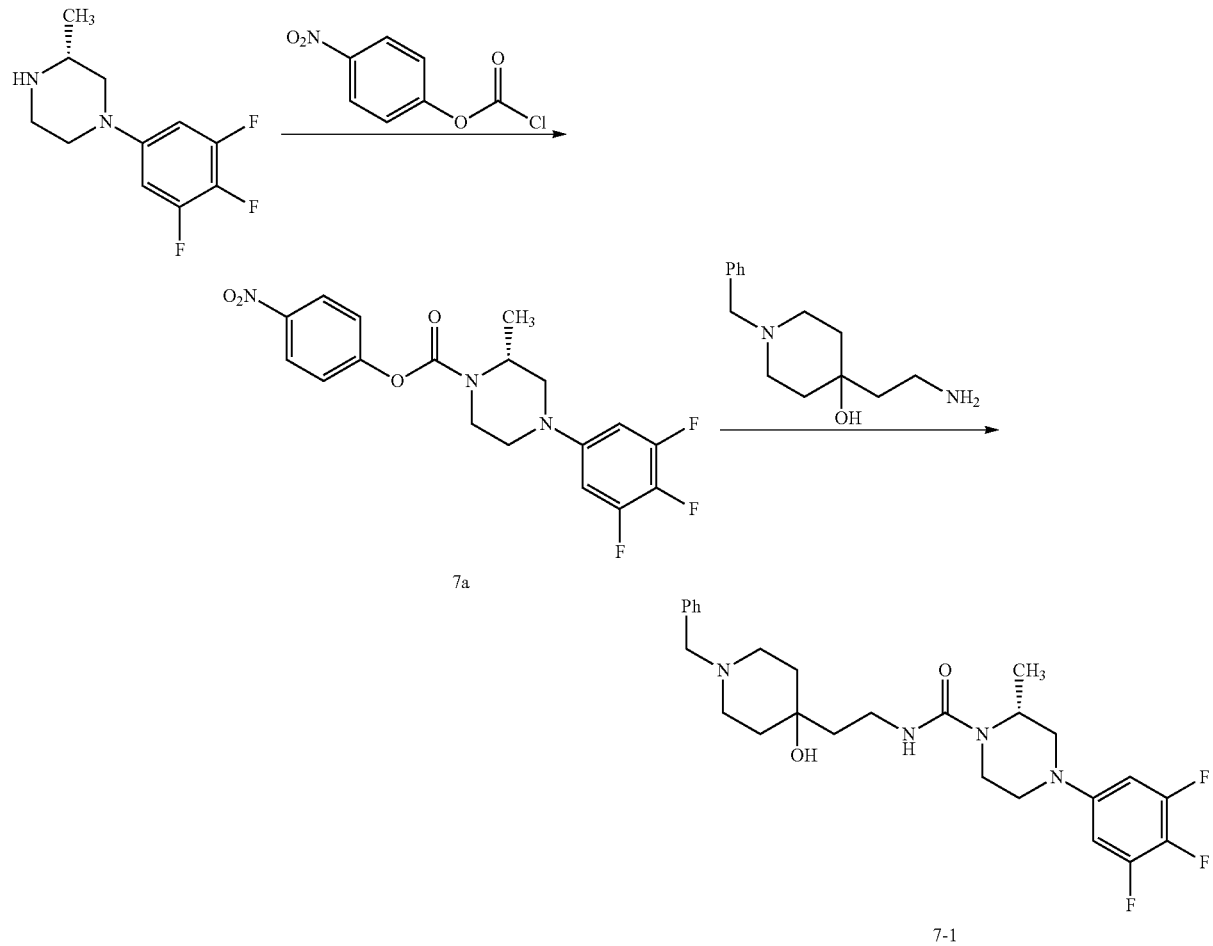

Step 7A: (2R)—N-[2-(1-benzyl-4-hydroxypiperidin-4-yl)ethyl]-2-methyl-4-(3,4,5-trifluorophenyl)piperazine-1-carboxamide A solution of (3R)-3-methyl-1-(3,4,5-trifluorophenyl)piperazine 1I (0.30 g, 1.3 mmol, 1.0 eq) and triethylamine (0.34 mL, 2.6 mmol, 2.0 eq) in methylene chloride (20 mL) was prepared and cooled to 0° C. Then, 4-nitrophenyl chloroformate (0.29 g, 1.4 mmol, 1.1 eq) was added dropwise and the mixture stirred for 10 min at 0° C. before removing the ice bath and stirring for an additional 15 min. The reaction mixture was diluted with methylene chloride, washed with sat. NH$_4$Cl, dried over Na$_2$SO$_4$ and concentrated in vacuo. Purification on a silica gel column (12 g) using an increasing gradient of MeOH (0-10%) in methylene chloride provided (2R)—N-[2-(1-benzyl-4-hydroxypiperidin-4-yl)ethyl]-2-methyl-4-(3,4,5-trifluorophenyl)piperazine-1-carboxamide 7a (0.40 g, 1.0 mmol, 78%) as a yellow oil.

Step 7B: (3R)-3-methyl-1-(3,4,5-trifluorophenyl)piperazine 4-(2-aminoethyl)-1-benzylpiperidin-4-ol To NMP solutions of (2R)—N-[2-(1-benzyl-4-hydroxypiperidin-4-yl)ethyl]-2-methyl-4-(3,4,5-trifluorophenyl)piperazine-1-carboxamide 7a (0.05 mL, 0.50 M, 1.0 eq) and 4-(2-aminoethyl)-1-benzylpiperidin-4-ol 14b (0.05 mL, 0.50 M, 1.0 eq) was added a NMP solution of triethylamine (0.05 mL, 2.0 M, 4.0 eq) and the mixture stirred at RT overnight. The reaction was diluted to a total volume of 1 mL using MeOH and submitted directly for preparative chromatography yielding (3R)-3-methyl-1-(3,4,5-trifluorophenyl)piperazine 4-(2-aminoethyl)-1-benzylpiperidin-4-ol 7-1. The table below provides the observed (Obs) ion m/z ratio for 7-1 (first compound listed in Table 5) and other compounds that were made according to the procedure as described in this example.

TABLE 5

| Cpd. No. | Compound Name | Obs Ion (m/z) |
| --- | --- | --- |
| 7-1 | (2R)-N-[2-(1-benzyl-4-hydroxypiperidin-4-yl)ethyl]-2-methyl-4-(3,4,5-trifluorophenyl)piperazine-1-carboxamide | 491.2 |
| 7-2 | (2R)-N-{2-[1-benzyl-4-(hydroxymethyl)piperidin-4-yl]ethyl}-4-(3-cyano-4-fluorophenyl)-2-methylpiperazine-1-carboxamide | 494.2 |
| 7-3 | (2R)-N-[2-(4-benzylpiperazin-1-yl)ethyl]-4-[3-cyano-4-(trifluoromethoxy)phenyl]-2-methylpiperazine-1-carboxamide | 531.2 |
| 7-4 | (2R)-N-[(2R)-2-(1-benzylpiperidin-4-yl)-2-hydroxyethyl]-4-(3-cyano-5-fluorophenyl)-2-methylpiperazine-1-carboxamide | 480.3 |
| 7-5 | (2R)-N-{2-[(3S)-1-benzylpyrrolidin-3-yl]ethyl}-2-methyl-4-(3,4,5-trifluorophenyl)piperazine-1-carboxamide | 461.2 |
| 7-6 | (2R)-N-[2-(4-benzylpiperazin-1-yl)ethyl]-2-methyl-4-(3,4,5-trifluorophenyl)piperazine-1-carboxamide | 476.2 |
| 7-7 | (2R)-N-[2-(4-benzyl-4-hydroxypiperidin-1-yl)ethyl]-2-methyl-4-(3,4,5-trifluorophenyl)piperazine-1-carboxamide | 491.2 |
| 7-8 | (2R)-N-{2-[(3S)-1-benzylpyrrolidin-3-yl]ethyl}-4-(3-cyano-5-fluorophenyl)-2-methylpiperazine-1-carboxamide | 450.2 |
| 7-9 | (2R)-N-[2-(1-benzylpiperidin-4-yl)ethyl]-4-[3-(difluoromethyl)-4-fluorophenyl]-2-methylpiperazine-1-carboxamide | 489.2 |
| 7-10 | (2R)-N-[(2R)-2-(1-benzylpiperidin-4-yl)-2-hydroxyethyl]-4-[3-cyano-4-(trifluoromethoxy)phenyl]-2-methylpiperazine-1-carboxamide | 546.2 |
| 7-11 | (2R)-N-[2-(1-benzyl-4-hydroxypiperidin-4-yl)ethyl]-4-(3-cyano-4-fluorophenyl)-2-methylpiperazine-1-carboxamide | 480.2 |
| 7-12 | (2R)-N-[(2R)-2-(1-benzylpiperidin-4-yl)-2-hydroxyethyl]-4-(3-cyano-4-fluorophenyl)-2-methylpiperazine-1-carboxamide | 480.2 |
| 7-13 | (2R)-N-(2-{[(3R,5R)-1-benzyl-5-(hydroxymethyl)pyrrolidin-3-yl](methyl)amino}ethyl)-2-methyl-4-(3,4,5-trifluorophenyl)piperazine-1-carboxamide | 520.2 |

Example 8

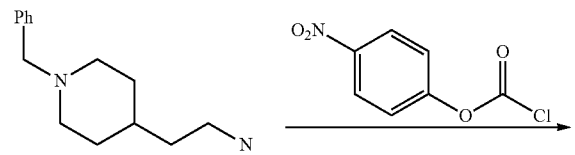

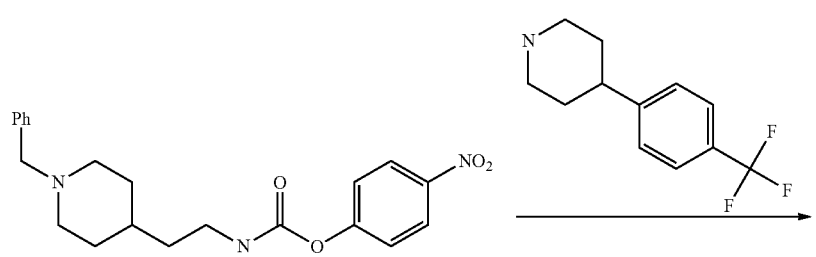

8a

-continued

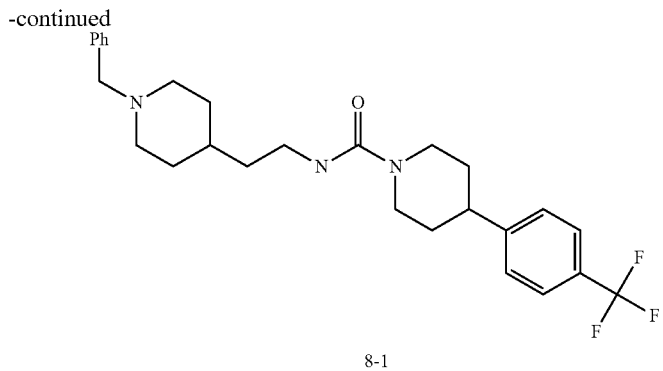

8-1

Step 8A: 4-Nitrophenyl N-[2-(1-benzylpiperidin-4-yl)ethyl]carbamate

A solution of 2-(1-benzylpiperidin-4-yl)ethan-1-amine (0.50 g, 2.3 mmol, 1.0 eq) in methylene chloride (10 mL) was prepared and added dropwise to a cooled methylene chloride solution (10 mL, 0° C.) of 4-nitrophenyl chloroformate (0.51 g, 2.5 mmol, 1.1 eq) and triethylamine (0.64 mL, 4.6 mmol, 2.0 eq). The reaction mixture was diluted further with methylene chloride, washed with sat. NH$_4$Cl, dried over MgSO$_4$ and concentrated in vacuo. Silica gel column was loaded using methylene chloride and run with an increasing gradient of MeOH (0-10%) in methylene chloride to provide 4-nitrophenyl N-[2-(1-benzylpiperidin-4-yl)ethyl]carbamate 8a (0.51 g, 1.0 mmol, 57%) as a yellow oil. Phenyl N-[2-(1-benzylpiperidin-4-yl)ethyl]carbamate 8b was made according to the same procedure, but with appropriately modified starting materials.

Step 8B: N-[2-(1-Benzylpiperidin-4-yl)ethyl]-4-[4-(trifluoromethyl)phenyl]piperidine-1-carboxamide To a NMP solution of 4-nitrophenyl N-[2-(1-benzylpiperidin-4-yl)ethyl]carbamate 8a (0.05 mL, 0.50 M, 1 eq) and 4-(4-trifluoromethylphenyl)piperidine (0.05 mL, 0.50 M, 1 eq) was added a NMP solution of triethylamine (0.05 mL, 2.0 M, 4 eq) and the mixture stirred at RT overnight. The reaction was diluted to a total volume of 1 mL using MeOH and submitted directly for preparative chromatography which yielded N-[2-(1-benzylpiperidin-4-yl)ethyl]-4-[4-(trifluoromethyl)phenyl]piperidine-1-carboxamide 8-1. The table below provides the observed (Obs) ion m/z ratio for 8-1 (first compound listed in Table 6) and other compounds that were made according to the procedure as described in this example.

TABLE 6

| Cpd. No. | Compound Name | Obs Ion (m/z) |
|---|---|---|
| 8-1 | N-[2-(1-benzylpiperidin-4-yl)ethyl]-4-[4-(trifluoromethyl)phenyl]piperidine-1-carboxamide | 474.3 |
| 8-2 | N-[2-(1-benzylpiperidin-4-yl)ethyl]-4-[3-(trifluoromethoxy)phenyl]piperazine-1-carboxamide | 491.3 |
| 8-3 | N-[2-(1-benzylpiperidin-4-yl)ethyl]-4-[3-(trifluoromethyl)phenyl]piperidine-1-carboxamide | 474.3 |
| 8-4 | N-[2-(1-benzylpiperidin-4-yl)ethyl]-4-(4-chlorophenyl)piperidine-1-carboxamide | 440.3 |
| 8-5 | N-[2-(1-benzylpiperidin-4-yl)ethyl]-4-(3-methoxyphenyl)piperidine-1-carboxamide | 436.1 |
| 8-6 | N-[2-(1-benzylpiperidin-4-yl)ethyl]-4-(2-methoxyphenyl)piperidine-1-carboxamide | 436.1 |
| 8-7 | N-[2-(1-benzylpiperidin-4-yl)ethyl]-4-(4-chloro-2-cyanophenyl)piperazine-1-carboxamide | 466.2 |
| 8-8 | N-[2-(1-benzylpiperidin-4-yl)ethyl]-4-[4-(trifluoromethoxy)phenyl]piperazine-1-carboxamide | 491.3 |
| 8-9 | 1-[2-(1-benzylpiperidin-4-yl)ethyl]-3-[1-(5-bromopyridin-2-yl)pyrrolidin-3-yl]-3-methylurea | 500.2 |
| 8-10 | 4-(1-benzothiophen-3-yl)-N-[2-(1-benzylpiperidin-4-yl)ethyl]piperidine-1-carboxamide | 462.4 |
| 8-11 | N-[2-(1-benzylpiperidin-4-yl)ethyl]-4-(3-chlorophenyl)piperazine-1-carboxamide | 441.4 |
| 8-12 | N-[2-(1-benzylpiperidin-4-yl)ethyl]-4-[2-cyano-4-(trifluoromethyl)phenyl]piperazine-1-carboxamide | 500.2 |
| 8-13 | N-[2-(1-benzylpiperidin-4-yl)ethyl]-4-(4-chlorophenyl)piperazine-1-carboxamide | 441.3 |
| 8-14 | 4-(1,3-benzothiazol-2-yl)-N-[2-(1-benzylpiperidin-4-yl)ethyl]piperidine-1-carboxamide | 463.4 |
| 8-15 | N-[2-(1-benzylpiperidin-4-yl)ethyl]-4-[3-chloro-5-(trifluoromethyl)pyridin-2-yl]piperazine-1-carboxamide | 510.1 |
| 8-16 | 1-[2-(1-benzylpiperidin-4-yl)ethyl]-3-{1-[3-chloro-5-(trifluoromethyl)pyridin-2-yl]pyrrolidin-3-yl}-3-methylurea | 524.2 |

TABLE 6-continued

| Cpd. No. | Compound Name | Obs Ion (m/z) |
|---|---|---|
| 8-17 | N-[2-(1-benzylpiperidin-4-yl)ethyl]-4-[3-(trifluoromethyl)phenyl]piperazine-1-carboxamide | 475.3 |
| 8-18 | N-[2-(1-benzylpiperidin-4-yl)ethyl]-4-(3-cyano-5-fluorophenyl)piperazine-1-carboxamide | 450.23 |
| 8-19 | N-[2-(1-benzylpiperidin-4-yl)ethyl]-4-hydroxy-4-[3-(trifluoromethyl)phenyl]piperidine-1-carboxamide | 490.4 |
| 8-20 | N-[2-(1-benzylpiperidin-4-yl)ethyl]-4-(4-fluorophenyl)piperidine-1-carboxamide | 424.2 |
| 8-21 | 1-[2-(1-benzylpiperidin-4-yl)ethyl]-3-methyl-3-{1-[4-(trifluoromethyl)phenyl]pyrrolidin-3-yl}urea | 489.3 |
| 8-22 | N-[2-(1-benzylpiperidin-4-yl)ethyl]-4-(3-cyano-4-fluorophenyl)piperazine-1-carboxamide | 450.3 |
| 8-23 | N-[2-(1-benzylpiperidin-4-yl)ethyl]-4-(4-chlorophenyl)-4-hydroxypiperidine-1-carboxamide | 456.2 |
| 8-24 | N-[2-(1-benzylpiperidin-4-yl)ethyl]-4-(4-methoxyphenyl)piperidine-1-carboxamide | 436.1 |
| 8-25 | N-[2-(1-benzylpiperidin-4-yl)ethyl]-4-(3-cyanophenyl)piperazine-1-carboxamide | 432.3 |
| 8-26 | N-[2-(1-benzylpiperidin-4-yl)ethyl]-4-(3-fluorophenyl)piperidine-1-carboxamide | 424.1 |
| 8-27 | N-[2-(1-benzylpiperidin-4-yl)ethyl]-4-(4-cyanophenyl)piperazine-1-carboxamide | 432.7 |
| 8-28 | N-[2-(1-benzylpiperidin-4-yl)ethyl]-4-(3-hydroxyphenyl)piperazine-1-carboxamide | 423.4 |
| 8-29 | N-[2-(1-benzylpiperidin-4-yl)ethyl]-4-(pyrimidin-2-yl)piperazine-1-carboxamide | 409.3 |
| 8-30 | N-[2-(1-benzylpiperidin-4-yl)ethyl]-4-(1H-indol-3-yl)piperidine-1-carboxamide | 445.1 |
| 8-31 | N-[2-(1-benzylpiperidin-4-yl)ethyl]-4-[3-(propan-2-yl)-1,2,4-oxadiazol-5-yl]piperidine-1-carboxamide | 440.2 |
| 8-32 | N-[2-(1-benzylpiperidin-4-yl)ethyl]-4-(2-fluorophenyl)piperidine-1-carboxamide | 424.1 |
| 8-33 | N-[2-(1-benzylpiperidin-4-yl)ethyl]-4-cyano-4-phenylpiperidine-1-carboxamide | 431.1 |
| 8-34 | N-[2-(1-benzylpiperidin-4-yl)ethyl]-4-(2-fluorophenyl)piperazine-1-carboxamide | 425.3 |
| 8-35 | N-[2-(1-benzylpiperidin-4-yl)ethyl]-4-(4-fluorophenyl)piperazine-1-carboxamide | 425.45 |
| 8-36 | 4-(4-acetylphenyl)-N-[2-(1-benzylpiperidin-4-yl)ethyl]piperazine-1-carboxamide | 449.2 |
| 8-37 | N-[2-(1-benzylpiperidin-4-yl)ethyl]-4-(4-ethylpiperazin-1-yl)piperidine-1-carboxamide | 442.4 |
| 8-38 | N-[2-(1-benzylpiperidin-4-yl)ethyl]-4-phenylpiperidine-1-carboxamide | 406.3 |
| 8-39 | 1-[2-(1-benzylpiperidin-4-yl)ethyl]-3-[1-(4-fluorophenyl)piperidin-4-yl]urea | 439.4 |
| 8-40 | 3-[2-(1-benzylpiperidin-4-yl)ethyl]-1-[1-(3-cyanophenyl)piperidin-4-yl]urea | 446.3 |
| 8-41 | 3-[2-(1-benzylpiperidin-4-yl)ethyl]-1-(4-phenoxyphenyl)urea | 430.2 |
| 8-42 | N-[2-(1-benzylpiperidin-4-yl)ethyl]-4-hydroxy-4-(2-methoxyphenyl)piperidine-1-carboxamide | 452.2 |

TABLE 6-continued

| Cpd. No. | Compound Name | Obs Ion (m/z) |
|---|---|---|
| 8-43 | N-[2-(1-benzylpiperidin-4-yl)ethyl]-4-[2-(hydroxymethyl)-4-methylphenyl]piperazine-1-carboxamide | 451.2 |
| 8-44 | N-[2-(1-benzylpiperidin-4-yl)ethyl]-4-(2-oxo-1,2,3,4-tetrahydroquinazolin-3-yl)piperidine-1-carboxamide | 476.2 |
| 8-45 | N-[2-(1-benzylpiperidin-4-yl)ethyl]-4-(5-cyanopyridin-2-yl)piperazine-1-carboxamide | 433.5 |
| 8-46 | 4-(1H-1,2,3-benzotriazol-1-yl)-N-[2-(1-benzylpiperidin-4-yl)ethyl]piperidine-1-carboxamide | 447.2 |
| 8-47 | N-[2-(1-benzylpiperidin-4-yl)ethyl]-4-(3-chloropyridin-2-yl)piperazine-1-carboxamide | 442.3 |
| 8-48 | N-[2-(1-benzylpiperidin-4-yl)ethyl]-3-(5-cyanopyrimidin-2-yl)-3,8-diazabicyclo[3.2.1]octane-8-carboxamide | 460.0 |

Example 9

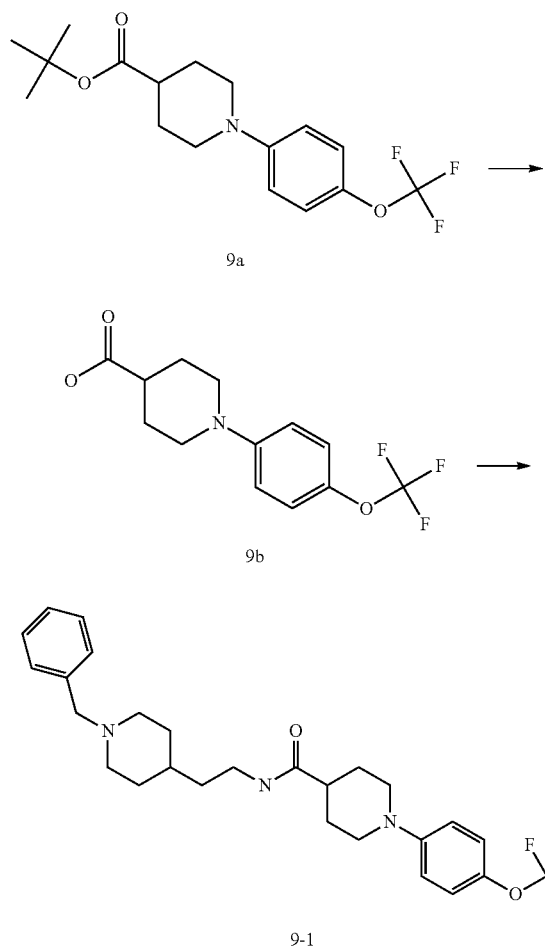

9a

9b 9-1

Step 9A: 1-[4-(Trifluoromethoxy)phenyl]piperidine-4-carboxylic acid

To a solution of tert-butyl piperidine-4-carboxylate (1.6 g, 8.7 mmol, 1.0 eq) and 1-iodo-4-(trifluoromethoxy)benzene (2.5 g, 8.7 mmol, 1.0 eq) in toluene (100 mL) was added sodium tert-butoxide (2.5 g, 25 mmol, 3.0 eq), racemic 2,2'-bis(diphenylphosphino)-1,1'-binaphthyl (0.54 g, 0.87 mmol, 0.10 eq), and lastly tris(dibenzylideneacetone)-dipalladium(0) (0.80 g, 0.87 mmol, 0.10 eq), and the reaction mixture heated to 100° C. overnight. The resulting dark reaction mixture was cooled, passed thru a pad of celite, and concentrated in vacuo. Silica gel column (40 g) was dry loaded and run using an increasing gradient of EtOAc (0-50%) in hexanes over 25 min yielding tert-butyl 1-[4-(trifluoromethoxy)phenyl]piperidine-4-carboxylate 9a. The chromatographed material 9a was dissolved in 20% TFA in methylene chloride (50 mL) and heated to 60° C. overnight. Following concentration, solid material was obtained by precipitation from hexanes and ether. The resulting white solid was collected by vacuum filtration to provide 1-[4-(trifluoromethoxy)phenyl]piperidine-4-carboxylic acid 9b (1.5 g, 5.2 mmol, 60% over two steps).

Step 9B: N-[2-(1-benzylpiperidin-4-yl)ethyl]-1-[4-(trifluoromethoxy)phenyl]piperidine-4-carboxamide To a solution of acid 9b (0.30 g, 1.0 mmol, 1.0 eq) and 2-(1-benzylpiperidin-4-yl)ethan-1-amine (0.26 g, 1.2 mmol, 1.2 eq) in methylene chloride (5 mL) was added triethylamine (0.41 mL, 3.0 mmol, 3.0 eq) followed by HATU (0.46 g, 1.2 mmol, 1.2 eq) and the mixture was stirred at room temperature overnight. The reaction mixture was diluted with sat. NH$_4$Cl and extracted with methylene chloride. The combined organic layers were dried over MgSO$_4$ and concentrated. A silica gel column was loaded using methylene chloride and run using an increasing gradient of MeOH (0-20%) in methylene chloride over 20 min to provide N-[2-(1-benzylpiperidin-4-yl)ethyl]-1-[4-(trifluoromethoxy)phenyl]piperidine-4-carboxamide 9-1 (0.39 g, 0.80 mmol, 80%). The table below provides the observed (Obs) ion m/z ratio for 9-1 (first compound listed in Table 7) and other compounds that were made according to the procedure as described in this example.

TABLE 7

| Cpd. No. | Compound Name | Obs Ion (m/z) |
|---|---|---|
| 9-1 | N-[2-(1-benzylpiperidin-4-yl)ethyl]-1-[4-(trifluoromethoxy)phenyl]piperidine-4-carboxamide | 490.3 |
| 9-2 | N-(1-benzylpiperidin-4-yl)-N-cyclopropyl-4-phenylbenzamide | 411.3 |
| 9-3 | N-[2-(1-benzylpiperidin-4-yl)ethyl]-N-(2-hydroxyethyl)-1-[4-(trifluoromethoxy)phenyl]piperidine-4-carboxamide | 534.3 |
| 9-4 | N-[2-(1-benzylpiperidin-4-yl)ethyl]-2-(4-chlorophenyl)-4-methyl-1,3-thiazole-5-carboxamide | 454.1 |
| 9-5 | (2R)-N-[(2S)-2-(1-benzylpiperidin-4-yl)-2-hydroxyethyl]-4-(3-cyano-5-fluorophenyl)-2-methylpiperazine-1-carboxamide | 480.2 |
| 9-6 | N-[2-(1-benzylpiperidin-4-yl)ethyl]-2-fluoro-4-[4-(trifluoromethoxy)phenyl]benzamide | 501.2 |
| 9-7 | N-[2-(1-benzylpiperidin-4-yl)ethyl]-4-[4-(trifluoromethoxy)phenyl]benzamide | 483.15 |
| 9-8 | N-[2-(1-benzylpiperidin-4-yl)-2-hydroxyethyl]-1-[4-(trifluoromethoxy)phenyl]piperidine-4-carboxamide | 506.2 |
| 9-9 | N-[2-(1-benzyl-4-hydroxypiperidin-4-yl)ethyl]-1-[3-fluoro-4-(trifluoromethoxy)phenyl]piperidine-4-carboxamide | 524.2 |
| 9-10 | (2R)-N-{2-[(3S)-1-benzylpyrrolidin-3-yl]ethyl}-4-[3-cyano-4-(trifluoromethoxy)phenyl]-2-methylpiperazine-1-carboxamide | 516.2 |
| 9-11 | N-{2-[1-benzyl-4-(hydroxymethyl)piperidin-4-yl]ethyl}-1-[3-(trifluoromethoxy)phenyl]piperidine-4-carboxamide | 520.2 |
| 9-12 | N-[2-(1-benzylpiperidin-4-yl)ethyl]-4-(4-chlorophenyl)-2-fluorobenzamide | 451.2 |
| 9-13 | N-{2-[1-benzyl-4-(hydroxymethyl)piperidin-4-yl]ethyl}-1-[4-(trifluoromethoxy)phenyl]piperidine-4-carboxamide | 520.3 |
| 9-14 | methyl 4-(4-{[2-(1-benzylpiperidin-4-yl)ethyl]carbamoyl}phenyl)benzoate | 457.25 |
| 9-15 | N-[(2R)-2-(1-benzylpiperidin-4-yl)-2-hydroxyethyl]-1-(3-cyano-4-fluorophenyl)piperidine-4-carboxamide | 465.2 |
| 9-16 | N-[2-(1-benzylpiperidin-4-yl)ethyl]-4-[4-(trifluoromethyl)phenyl]benzamide | 467.3 |
| 9-17 | N-(2-{[(3S)-1-benzylpyrrolidin-3-yl](methyl)amino}ethyl)-1-[4-(trifluoromethoxy)phenyl]piperidine-4-carboxamide | 505.3 |
| 9-18 | 4-chloro-3-(3-cyanoquinolin-2-yl)-N-[(3R)-1-cyclohexylpyrrolidin-3-yl]-N-methylbenzamide | 473.2 |
| 9-19 | N-[2-(4-benzyl-4-hydroxypiperidin-1-yl)ethyl]-2-[4-(trifluoromethoxy)phenyl]imidazo[1,2-a]pyridine-7-carboxamide | 539.2 |
| 9-20 | N-{2-[(3R)-1-benzylpyrrolidin-3-yl]ethyl}-4-chloro-3-(4-chloro-6-methylpyridin-3-yl)benzamide | 468.1 |
| 9-21 | 1-(1-benzylpiperidin-4-yl)-4-{1-[3-chloro-5-(trifluoromethyl)pyridin-2-yl]piperidine-4-carbonyl}piperazine | 550.2 |
| 9-22 | N-(2-{[(3R)-1-benzylpyrrolidin-3-yl](methyl)amino}ethyl)-1-[3-(trifluoromethoxy)phenyl]piperidine-4-carboxamide | 505.3 |
| 9-23 | N-[1-(1-benzylpiperidin-4-yl)pyrrolidin-3-yl]-N-methyl-1-[4-(trifluoromethoxy)phenyl]piperidine-4-carboxamide | 545.3 |
| 9-24 | N-{2-[1-benzyl-4-(hydroxymethyl)piperidin-4-yl]ethyl}-1-(3-cyano-4-fluorophenyl)piperidine-4-carboxamide | 479.2 |
| 9-25 | N-[2-(1-benzylpiperidin-4-yl)ethyl]-2-[4-(trifluoromethoxy)phenyl]imidazo[1,2-a]pyridine-7-carboxamide | 523.2 |
| 9-26 | N-(2-{[(3R)-1-benzylpyrrolidin-3-yl](methyl)amino}ethyl)-1-[4-(trifluoromethoxy)phenyl]piperidine-4-carboxamide | 505.3 |
| 9-27 | N-[2-(1-benzyl-3-hydroxypiperidin-4-yl)ethyl]-1-[4-(trifluoromethoxy)phenyl]piperidine-4-carboxamide | 506.2 |
| 9-28 | N-(2-{[(3R)-1-benzylpyrrolidin-3-yl]amino}ethyl)-1-[3-fluoro-4-(trifluoromethoxy)phenyl]piperidine-4-carboxamide | 509.2 |
| 9-29 | N-[2-(1-benzylpiperidin-4-yl)ethyl]-1-(4-cyanophenyl)piperidine-4-carboxamide | 431.5 |
| 9-30 | N-[2-(1-benzylpiperidin-4-yl)ethyl]-4-(4-cyanophenyl)benzamide | 424.3 |
| 9-31 | N-(2-{[(3S)-1-benzylpyrrolidin-3-yl](methyl)amino}ethyl)-1-[3-(trifluoromethoxy)phenyl]piperidine-4-carboxamide | 505.3 |
| 9-32 | N-[2-(1-benzylpiperidin-4-yl)ethyl]-4-methyl-2-[4-(trifluoromethyl)phenyl]-1,3-thiazole-5-carboxamide | 488.2 |
| 9-33 | N-[(3R)-1-benzylpyrrolidin-3-yl]-N-methyl-1-{1-[4-(trifluoromethoxy)phenyl]piperidine-4-carbonyl}piperidin-4-amine | 545.3 |
| 9-34 | N-[2-(1-benzylpiperidin-4-yl)ethyl]-N-methyl-1-[4-(trifluoromethoxy)phenyl]piperidine-4-carboxamide | 504.3 |
| 9-35 | N-(2-{[1-benzyl-4-(hydroxymethyl)pyrrolidin-3-yl](methyl)amino}ethyl)-1-[3-fluoro-4-(trifluoromethoxy)phenyl]piperidine-4-carboxamide | 553.3 |
| 9-36 | 3-(1-benzylpiperidin-4-yl)-N-{1-[4-(trifluoromethoxy)phenyl]piperidin-4-yl}propanamide | 490.2 |
| 9-37 | N-[2-(1-benzylpiperidin-4-yl)ethyl]-1-(5-bromopyrimidin-2-yl)piperidine-4-carboxamide | 488.1 |
| 9-38 | N-(2-{[(3R)-1-benzylpyrrolidin-3-yl](methyl)amino}ethyl)-4-phenylbenzamide | 414.2 |

TABLE 7-continued

| Cpd. No. | Compound Name | Obs Ion (m/z) |
|---|---|---|
| 9-39 | N-(2-{[(3R)-1-benzylpyrrolidin-3-yl](methyl)amino}ethyl)-4-[4-(trifluoromethoxy)phenyl]benzamide | 498.3 |
| 9-40 | N-[2-(1-benzylpiperidin-4-yl)ethyl]-2-fluoro-4-(4-methylphenyl)benzamide | 431.25 |
| 9-41 | N-[2-(1-benzylpiperidin-4-yl)ethyl]-4-(4-fluorophenyl)benzamide | 417.3 |
| 9-42 | 1-benzyl-1-methyl-4-[2-(N-methyl-1-{1-[4-(trifluoromethoxy)phenyl]piperidin-4-yl}formamido)ethyl]piperidin-1-ium | 518.3 |
| 9-43 | 2-[4-(benzyloxy)phenyl]-N-[2-(1-benzylpiperidin-4-yl)ethyl]acetamide | 443.3 |
| 9-44 | N-[2-(1-benzyl-4-hydroxypiperidin-4-yl)ethyl]-1-(3-cyano-4-fluorophenyl)piperidine-4-carboxamide | 465.2 |
| 9-45 | N-[2-(1-benzylpiperidin-4-yl)ethyl]-4-(2,6-dioxo-1,3-dipropyl-2,3,6,9-tetrahydro-1H-purin-8-yl)benzamide | 557.3 |
| 9-46 | N-[2-(1-benzyl-4-hydroxypiperidin-4-yl)ethyl]-1-[3-(trifluoromethoxy)phenyl]piperidine-4-carboxamide | 506.2 |
| 9-47 | N-[2-(1-benzylpiperidin-4-yl)ethyl]-1-(5-cyanopyridin-2-yl)piperidine-4-carboxamide | 432.3 |
| 9-48 | N-(1-benzylpiperidin-4-yl)-N-cyclopropyl-2-[4-(trifluoromethoxy)phenyl]imidazo[1,2-a]pyridine-7-carboxamide | 535.2 |
| 9-49 | N-{2-[(3S)-1-benzylpyrrolidin-3-yl]ethyl}-1-[4-(trifluoromethoxy)phenyl]piperidine-4-carboxamide | 476.3 |
| 9-50 | 3-(1-benzylpiperidin-4-yl)-N-{1-[3-(trifluoromethoxy)phenyl]piperidin-4-yl}propanamide | 490.2 |
| 9-51 | N-[2-(1-benzylpiperidin-4-yl)ethyl]-2-(4-methoxyphenyl)-7-methylpyrazolo[1,5-a]pyrimidine-6-carboxamide | 484.25 |
| 9-52 | N-[2-(1-benzylpiperidin-4-yl)ethyl]-1-(4-methylpyridin-2-yl)piperidine-4-carboxamide | 421.3 |
| 9-53 | N-(1-benzylpiperidin-4-yl)-N-cyclopropyl-4-(thiophen-2-yl)benzamide | 417.2 |
| 9-54 | N-(2-{[(3R)-1-benzylpyrrolidin-3-yl]amino}ethyl)-1-[3-(trifluoromethoxy)phenyl]piperidine-4-carboxamide | 491.2 |
| 9-55 | N-[2-(1-benzylpiperidin-4-yl)ethyl]-4-(thiophen-2-yl)benzamide | 405.2 |
| 9-56 | N-[2-(1-benzylpiperidin-4-yl)ethyl]-4-[(trifluoromethyl)sulfanyl]benzamide | 423.1 |
| 9-57 | N-[2-(1-benzylpiperidin-4-yl)ethyl]-2-(6-fluoropyridin-3-yl)-4-methyl-1,3-thiazole-5-carboxamide | 438.1 |
| 9-58 | N-[2-(1-benzylpiperidin-4-yl)ethyl]-1-[3-chloro-5(trifluoromethyl)pyridin-2-yl]-N-cyclopropylpiperidine-4-carboxamide | 549.2 |
| 9-59 | N-[2-(1-benzylpiperidin-4-yl)ethyl]-5-(4-methoxyphenyl)-7-(trifluoromethyl)pyrazolo[1,5-a]pyrimidine-2-carboxamide | 538.2 |
| 9-60 | N-[2-(1-benzylpiperidin-4-yl)ethyl]-4-chloro-3-(3-cyanoquinolin-2-yl)benzamide | 509.2 |
| 9-61 | N-[2-(1-benzylpiperidin-4-yl)ethyl]-2-(2,4-dichlorophenyl)-5-methyl-1H-imidazole-4-carboxamide | 471 |
| 9-62 | N-{2-[1-benzyl-3-(hydroxymethyl)piperidin-4-yl]ethyl}-1-[4-(trifluoromethoxy)phenyl]piperidine-4-carboxamide | 520.2 |
| 9-63 | N-[2-(1-benzylpiperidin-4-yl)ethyl]-1-[3-chloro-5(trifluoromethyl)pyridin-2-yl]piperidine-4-carboxamide | 509.2 |
| 9-64 | N-{2-[1-benzyl-4-(hydroxymethyl)piperidin-4-yl]ethyl}-1-[3-fluoro-4-(trifluoromethoxy)phenyl]piperidine-4-carboxamide | 538.2 |
| 9-65 | N-[(1-benzylpiperidin-4-yl)methyl]-1-[3-chloro-5-(trifluoromethyl)pyridin-2-yl]piperidine-4-carboxamide | 495.1 |
| 9-66 | N-{2-[(3R)-1-benzylpyrrolidin-3-yl]ethyl}-1-[4-(trifluoromethoxy)phenyl]piperidine-4-carboxamide | 476.2 |
| 9-67 | N-[2-(1-benzylpiperidin-4-yl)ethyl]-4-chloro-3-(4-chloro-6-methylpyridin-3-yl)benzamide | 482.2 |
| 9-68 | N-[2-(4-benzylpiperidin-1-yl)ethyl]-2-[4-(trifluoromethoxy)phenyl]imidazo[1,2-a]pyridine-7-carboxamide | 523.1 |
| 9-69 | N-[2-(1-benzylpiperidin-4-yl)ethyl]-4-(4-hydroxyphenyl)benzamide | 415.05 |
| 9-70 | N-[2-(1-benzylpiperidin-4-yl)ethyl]-4-[4-(trifluoromethoxy)phenyl]benzamide | 483.15 |
| 9-71 | N-[2-(1-benzylpiperidin-4-yl)-2-hydroxyethyl]-1-[4-(trifluoromethoxy)phenyl]piperidine-4-carboxamide | 506.2 |
| 9-72 | N-[2-(1-benzyl-4-hydroxypiperidin-4-yl)ethyl]-1-[3-fluoro-4-(trifluoromethoxy)phenyl]piperidine-4-carboxamide | 524.2 |
| 9-73 | N-[2-(1-benzylpiperidin-4-yl)ethyl]-1-(3-cyano-4-fluorophenyl)piperidine-4-carboxamide | 449.3 |
| 9-74 | N-[2-(1-benzylpiperidin-4-yl)ethyl]-1-(5-cyanopyridin-2-yl)-2-methyl-1H-imidazole-4-carboxamide | 429.1 |
| 9-75 | N-[2-(1-benzylpiperidin-4-yl)ethyl]-1-(5-cyanopyridin-2-yl)-1H-imidazole-4-carboxamide | 415.1 |

Example 10

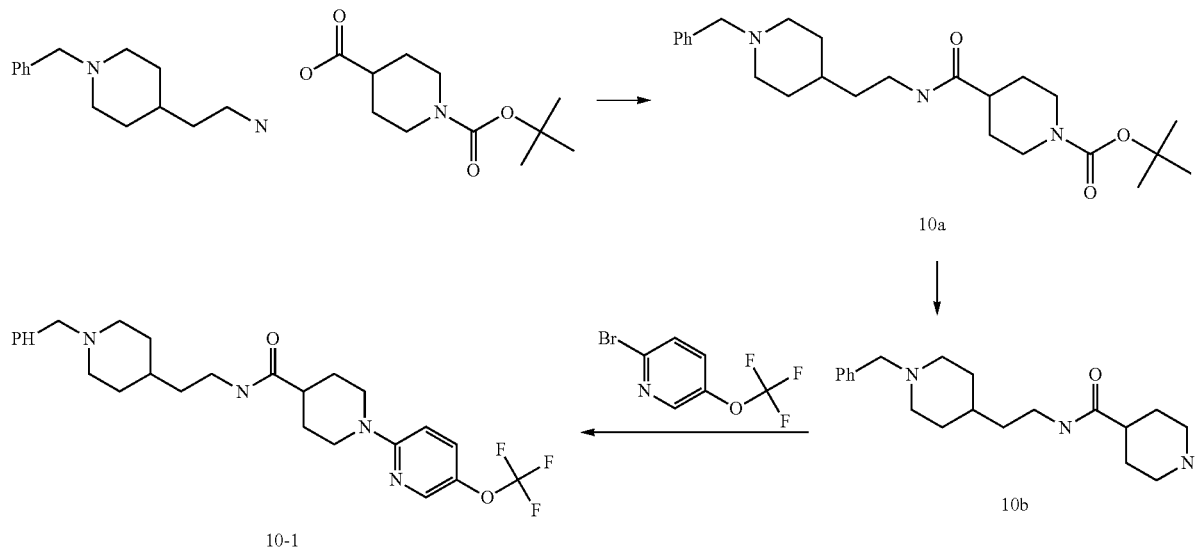

Step 10A: N-[2-(1-benzylpiperidin-4-yl)ethyl]piperidine-4-carboxamide

To a solution of 1-[(tert-butoxy)carbonyl]piperidine-4-carboxylic acid (2.0 g, 8.7 mmol, 1.0 eq) and 2-(1-benzylpiperidin-4-yl)ethan-1-amine (2.2 g, 9.6 mmol, 1.1 eq) in methylene chloride (20 mL) was added triethylamine (4.3 mL, 26.1 mmol, 3.0 eq) followed by HATU (4.0 g, 10.4 mmol, 1.2 eq) and the reaction stirred at room temperature overnight. The reaction mixture was diluted with saturated NH$_4$Cl and extracted with methylene chloride. The combined organic layers were dried over MgSO$_4$ and concentrated. A silica gel column was loaded using methylene chloride and run using an increasing gradient of MeOH (0-10%) in methylene chloride over 20 min yielding tert-butyl 4-{[2-(1-benzylpiperidin-4-yl)ethyl]carbamoyl}piperidine-1-carboxylate 10a. A portion of the chromatographed 10a (1.0 g, 2.3 mmol) was dissolved in 20% TFA in methylene chloride (5 mL) and heated to 50° C. overnight. The reaction mixture was concentrated, dissolved in MeOH, and made basic with the addition of MP-carbonate. Following removal of the resin and concentration of the filtrate, the free base of N-[2-(1-benzylpiperidin-4-yl)ethyl] piperidine-4-carboxamide 10b (0.62 g, 1.9 mmol, 83%) was isolated as a yellow oil.

(3R,4R)—N-[2-(1-benzylpiperidin-4-yl)ethyl]-3-methylpiperidine-4-carboxamide 10c was synthesized following the same overall procedure.

Step 10B: N-[2-(1-benzylpiperidin-4-yl)ethyl]-1-[5-(trifluoromethoxy)pyridin-2-yl]piperidine-4-carboxamide To a solution of 10b (20 mg, 0.06 mmol, 1.0 eq) and 2-bromo-5-(trifluoromethoxy)pyridine (14 mg, 0.06 mmol, 1.0 eq) in toluene (1 mL) was added sodium tert-butoxide (17 mg, 0.18 mmol, 3.0 eq), racemic 2,2'-bis(diphenylphosphino)-1,1'-binaphthyl (3.7 mg, 0.006 mmol, 0.10 eq), and lastly tris(dibenzylideneacetone)-dipalladium(0) (5.5 mg, 0.006 mmol, 0.10 eq), and the reaction mixture stirred vigorously at 100° C. overnight. The resulting dark suspension was cooled, passed through an HPLC filter and concentrated. Then, the crude material was treated with 1.5 mL of MeOH, passed through an additional HPLC filter (leaving any precipitate behind), and submitted for directly for preparative chromatography yielding N-[2-(1-benzylpiperidin-4-yl)ethyl]-1-[5-(trifluoromethoxy)pyridin-2-yl]piperidine-4-carboxamide 10-1. The table below provides the observed (Obs) ion m/z ratio for 10-1 (first compound listed in Table 8) and other compounds that were made according to the procedure as described in this example.

TABLE 8

| Cpd. No. | Compound Name | Obs Ion (m/z) |
|---|---|---|
| 10-1 | N-[2-(1-benzylpiperidin-4-yl)ethyl]-1-[5 (trifluoromethoxy)pyridin-2-yl]piperidine-4-carboxamide | 491.2 |
| 10-2 | N-[2-(1-benzylpiperidin-4-yl)ethyl]-1-(3-cyano-4-methoxyphenyl)piperidine-4-carboxamide | 461.3 |
| 10-3 | N-[2-(1-benzylpiperidin-4-yl)ethyl]-1-phenylpiperidine-4-carboxamide | 406.3 |
| 10-4 | N-[2-(1-benzylpiperidin-4-yl)ethyl]-4-methyl-1-[2-(trifluoromethoxy)phenyl]piperidine-4-carboxamide | 504.2 |
| 10-5 | N-[2-(1-benzylpiperidin-4-yl)ethyl]-1-(2,2-difluoro-2H-1,3-benzodioxol-5-yl)piperidine-4-carboxamide | 486.3 |
| 10-6 | N-[2-(1-benzylpiperidin-4-yl)ethyl]-3-methyl-1-[4-(trifluoromethoxy)phenyl]piperidine-4-carboxamide | 504.25 |

TABLE 8-continued

| Cpd. No. | Compound Name | Obs Ion (m/z) |
|---|---|---|
| 10-7 | N-[2-(1-benzylpiperidin-4-yl)ethyl]-1-(3,4,5-trifluorophenyl)piperidine-4-carboxamide | 460.3 |
| 10-8 | N-[2-(1-benzylpiperidin-4-yl)ethyl]-1-[3-fluoro-4-(trifluoromethoxy)phenyl]piperidine-4-carboxamide | 508.5 |
| 10-9 | N-[2-(1-benzylpiperidin-4-yl)ethyl]-1-[4-(trifluoromethyl)phenyl]piperidine-4-carboxamide | 474.3 |
| 10-10 | N-[2-(1-benzylpiperidin-4-yl)ethyl]-1-[3-methoxy-4-(trifluoromethoxy)phenyl]piperidine-4-carboxamide | 520.3 |
| 10-11 | N-[2-(1-benzylpiperidin-4-yl)ethyl]-1-[4-fluoro-3-(trifluoromethoxy)phenyl]piperidine-4-carboxamide | 508.3 |
| 10-12 | (2R)-N-[2-(1-benzylpiperidin-4-yl)ethyl]-4-[2-fluoro-4-(trifluoromethoxy)phenyl]-2-methylpiperazine-1-carboxamide | 523.2 |
| 10-13 | N-[2-(1-benzylpiperidin-4-yl)ethyl]-1-[4-cyano-3-(trifluoromethoxy)phenyl]piperidine-4-carboxamide | 515.2 |
| 10-14 | N-[2-(1-benzylpiperidin-4-yl)ethyl]-1-(3-cyano-5-fluorophenyl)piperidine-4-carboxamide | 449.3 |
| 10-15 | N-[2-(1-benzylpiperidin-4-yl)ethyl]-1-(5-cyanopyridin-3-yl)piperidine-4-carboxamide | 432.3 |
| 10-16 | N-[2-(1-benzylpiperidin-4-yl)ethyl]-3-methyl-1-[2-(trifluoromethoxy)phenyl]piperidine-4-carboxamide | 504.2 |
| 10-17 | N-[2-(1-benzylpiperidin-4-yl)ethyl]-4-fluoro-1-[2-(trifluoromethoxy)phenyl]piperidine-4-carboxamide | 508.2 |
| 10-18 | N-[2-(1-benzylpiperidin-4-yl)ethyl]-3-methyl-1-[3-(trifluoromethoxy)phenyl]piperidine-4-carboxamide | 504.2 |
| 10-19 | N-[2-(1-benzylpiperidin-4-yl)ethyl]-1-[3-(trifluoromethoxy)phenyl]piperidine-4-carboxamide | 490.4 |
| 10-20 | N-[2-(1-benzyl-4-hydroxypiperidin-4-yl)ethyl]-1-[3-cyano-4-(trifluoromethoxy)phenyl]piperidine-4-carboxamide | 531.2 |
| 10-21 | N-[2-(1-benzylpiperidin-4-yl)ethyl]-1-(3,4-difluorophenyl)piperidine-4-carboxamide | 442.2 |
| 10-22 | N-[2-(1-benzylpiperidin-4-yl)ethyl]-1-(3,5-difluorophenyl)piperidine-4-carboxamide | 442.3 |
| 10-23 | N-[2-(1-benzylpiperidin-4-yl)ethyl]-1-[3-cyano-5-(trifluoromethoxy)phenyl]piperidine-4-carboxamide | 515.2 |
| 10-24 | N-[2-(1-benzylpiperidin-4-yl)ethyl]-1-[5-(trifluoromethyl)pyridin-2-yl]piperidine-4-carboxamide | 475.3 |
| 10-25 | N-[2-(1-benzylpiperidin-4-yl)ethyl]-4-methyl-1-[3-(trifluoromethoxy)phenyl]piperidine-4-carboxamide | 504.2 |
| 10-26 | 2-(1-benzylpiperidin-4-yl)-N-({1-[3-(trifluoromethoxy)phenyl]piperidin-4-yl}methyl)acetamide | 490.2 |
| 10-27 | N-[2-(1-benzylpiperidin-4-yl)ethyl]-1-(6-chloropyridin-3-yl)piperidine-4-carboxamide | 441.2 |
| 10-28 | N-[2-(1-benzylpiperidin-4-yl)ethyl]-1-(5-methoxypyridin-2-yl)piperidine-4-carboxamide | 437.2 |
| 10-29 | N-[2-(1-benzylpiperidin-4-yl)ethyl]-1-[3-methoxy-5-(trifluoromethoxy)phenyl]piperidine-4-carboxamide | 520.3 |
| 10-30 | N-[2-(1-benzylpiperidin-4-yl)ethyl]-1-[4-(trifluoromethyl)pyrimidin-2-yl]piperidine-4-carboxamide | 476.3 |
| 10-31 | N-[2-(1-benzylpiperidin-4-yl)ethyl]-4-methyl-1-[4-(trifluoromethoxy)phenyl]piperidine-4-carboxamide | 504.2 |
| 10-32 | N-[2-(1-benzylpiperidin-4-yl)ethyl]-1-[4-(trifluoromethyl)pyridin-2-yl]piperidine-4-carboxamide | 475.2 |
| 10-33 | N-[2-(1-benzylpiperidin-4-yl)ethyl]-1-[4-methoxy-3-(trifluoromethoxy)phenyl]piperidine-4-carboxamide | 520.2 |
| 10-34 | N-[2-(1-benzylpiperidin-4-yl)ethyl]-1-[6-(trifluoromethoxy)pyridin-3-yl]piperidine-4-carboxamide | 491.2 |
| 10-35 | N-[2-(1-benzylpiperidin-4-yl)ethyl]-1-(4-fluorophenyl)piperidine-4-carboxamide | 424.3 |
| 10-36 | N-[2-(1-benzylpiperidin-4-yl)ethyl]-1-[3-cyano-4-(trifluoromethoxy)phenyl]-4-hydroxypiperidine-4-carboxamide | 531.2 |
| 10-37 | N-[2-(1-benzylpiperidin-4-yl)ethyl]-1-[2-fluoro-4-(trifluoromethoxy)phenyl]piperidine-4-carboxamide | 508.2 |
| 10-38 | N-[2-(1-benzylpiperidin-4-yl)ethyl]-4-methoxy-1-[4-(trifluoromethoxy)phenyl]piperidine-4-carboxamide | 520.2 |
| 10-39 | N-[2-(1-benzylpiperidin-4-yl)ethyl]-1-(3-fluoro-4-methoxyphenyl)piperidine-4-carboxamide | 454.4 |
| 10-40 | N-[2-(1-benzylpiperidin-4-yl)ethyl]-4-hydroxy-1-(3,4,5-trifluorophenyl)piperidine-4-carboxamide | 476.3 |
| 10-41 | N-[2-(1-benzylpiperidin-4-yl)ethyl]-1-[3-fluoro-4-(trifluoromethoxy)phenyl]-4-hydroxypiperidine-4-carboxamide | 524.2 |
| 10-42 | N-[2-(1-benzylpiperidin-4-yl)ethyl]-3-methyl-1-[4-(trifluoromethoxy)phenyl]piperidine-4-carboxamide | 504.25 |
| 10-43 | N-[2-(1-benzylpiperidin-4-yl)ethyl]-1-(3,4,5-trifluorophenyl)piperidine-4-carboxamide | 460.3 |
| 10-44 | N-[2-(1-benzylpiperidin-4-yl)ethyl]-1-[3-fluoro-4-(trifluoromethoxy)phenyl]piperidine-4-carboxamide | 508.5 |

TABLE 8-continued

| Cpd. No. | Compound Name | Obs Ion (m/z) |
|---|---|---|
| 10-45 | N-[2-(1-benzylpiperidin-4-yl)ethyl]-1-(2,2-difluoro-2H-1,3-benzodioxol-4-yl)piperidine-4-carboxamide | 486.3 |
| 10-46 | N-[2-(1-benzylpiperidin-4-yl)ethyl]-1-[3-cyano-5-(trifluoromethoxy)phenyl]-4-hydroxypiperidine-4-carboxamide | 531.2 |
| 10-47 | N-[2-(1-benzylpiperidin-4-yl)ethyl]-4-methoxy-1-[4-(trifluoromethyl)pyridin-2-yl]piperidine-4-carboxamide | 505.2 |
| 10-48 | N-[2-(1-benzylpiperidin-4-yl)ethyl]-4-methoxy-1-[5-(trifluoromethyl)pyridin-2-yl]piperidine-4-carboxamide | 505.2 |
| 10-49 | (3R)-N-[2-(1-benzylpiperidin-4-yl)ethyl]-1-[3-(trifluoromethoxy)phenyl]pyrrolidine-3-carboxamide | 476.15 |
| 10-50 | N-[2-(1-benzylpiperidin-4-yl)ethyl]-1-(4-cyano-2-fluorophenyl)piperidine-4-carboxamide | 449.3 |
| 10-51 | N-[2-(1-benzylpiperidin-4-yl)ethyl]-1-(3-cyano-4-fluorophenyl)-4-hydroxypiperidine-4-carboxamide | 465.25 |
| 10-52 | (3S)-N-[2-(1-benzylpiperidin-4-yl)ethyl]-1-[3-(trifluoromethoxy)phenyl]pyrrolidine-3-carboxamide | 476.2 |
| 10-53 | N-[2-(1-benzylpiperidin-4-yl)ethyl]-1-(3-methoxyphenyl)piperidine-4-carboxamide | 436.3 |
| 10-54 | N-[2-(1-benzylpiperidin-4-yl)ethyl]-1-(3-cyano-5-methoxyphenyl)piperidine-4-carboxamide | 461.6 |
| 10-55 | N-[2-(1-benzylpiperidin-4-yl)ethyl]-4-fluoro-1-[4-(trifluoromethoxy)phenyl]piperidine-4-carboxamide | 508.2 |
| 10-56 | N-[2-(1-benzylpiperidin-4-yl)ethyl]-1-[3-methyl-4-(trifluoromethyl)phenyl]piperidine-4-carboxamide | 504.3 |
| 10-57 | N-[2-(1-benzylpiperidin-4-yl)ethyl]-1-[3-cyano-4-(trifluoromethyl)phenyl]piperidine-4-carboxamide | 515.2 |
| 10-58 | N-[(2S)-2-(1-benzylpiperidin-4-yl)-2-hydroxyethyl]-1-(3-cyano-4-fluorophenyl)piperidine-4-carboxamide | 465.2 |
| 10-59 | N-[2-(1-benzylpiperidin-4-yl)ethyl]-1-(2-fluorophenyl)piperidine-4-carboxamide | 424.3 |
| 10-60 | N-[2-(1-benzylpiperidin-4-yl)ethyl]-1-(4-methoxyphenyl)piperidine-4-carboxamide | 436.35 |
| 10-61 | N-[2-(1-benzylpiperidin-4-yl)ethyl]-4-hydroxy-1-[5-(trifluoromethoxy)pyridin-2-yl]piperidine-4-carboxamide | 507.2 |
| 10-62 | N-[2-(1-benzylpiperidin-4-yl)ethyl]-4-hydroxy-1-[3-(trifluoromethoxy)phenyl]piperidine-4-carboxamide | 506.2 |
| 10-63 | N-[2-(1-benzylpiperidin-4-yl)ethyl]-4-methoxy-1-[5-(trifluoromethoxy)pyridin-2-yl]piperidine-4-carboxamide | 521.2 |
| 10-64 | N-[2-(1-benzylpiperidin-4-yl)ethyl]-1-(2,5-difluorophenyl)-4-hydroxypiperidine-4-carboxamide | 458.2 |
| 10-65 | N-[2-(1-benzylpiperidin-4-yl)ethyl]-1-(3-methanesulfonylphenyl)piperidine-4-carboxamide | 484.3 |
| 10-66 | N-[2-(1-benzylpiperidin-4-yl)ethyl]-1-(4-cyanopyridin-2-yl)piperidine-4-carboxamide | 432.3 |
| 10-67 | N-[2-(1-benzylpiperidin-4-yl)ethyl]-1-(2-cyanophenyl)piperidine-4-carboxamide | 431.25 |
| 10-68 | N-[2-(1-benzylpiperidin-4-yl)ethyl]-1-[6-(trifluoromethyl)pyridin-3-yl]piperidine-4-carboxamide | 475.3 |
| 10-69 | N-[2-(1-benzylpiperidin-4-yl)ethyl]-1-(2-cyano-4-fluorophenyl)piperidine-4-carboxamide | 449.4 |
| 10-70 | N-[2-(1-benzylpiperidin-4-yl)ethyl]-1-[2-(trifluoromethoxy)phenyl]piperidine-4-carboxamide | 490.2 |
| 10-71 | (3S)-N-[2-(1-benzylpiperidin-4-yl)ethyl]-1-[4-(trifluoromethoxy)phenyl]pyrrolidine-3-carboxamide | 476.2 |
| 10-72 | (3R)-N-[2-(1-benzylpiperidin-4-yl)ethyl]-1-[4-(trifluoromethoxy)phenyl]pyrrolidine-3-carboxamide | 476.25 |
| 10-73 | N-[2-(1-benzylpiperidin-4-yl)ethyl]-1-(5-fluoropyridin-2-yl)piperidine-4-carboxamide | 425.3 |
| 10-74 | N-[2-(1-benzylpiperidin-4-yl)ethyl]-1-(4,6-dimethylpyrimidin-2-yl)piperidine-4-carboxamide | 436.4 |
| 10-75 | N-[2-(1-benzylpiperidin-4-yl)ethyl]-4-methoxy-1-[2-(trifluoromethoxy)phenyl]piperidine-4-carboxamide | 520.2 |
| 10-76 | N-[2-(1-benzylpiperidin-4-yl)ethyl]-1-[4-(difluoromethoxy)phenyl]piperidine-4-carboxamide | 472.3 |
| 10-77 | N-[2-(1-benzylpiperidin-4-yl)ethyl]-1-(3-cyanophenyl)piperidine-4-carboxamide | 431.3 |
| 10-78 | N-[2-(1-benzylpiperidin-4-yl)ethyl]-1-(4-cyano-3-fluorophenyl)piperidine-4-carboxamide | 449.4 |
| 10-79 | (3R)-N-[2-(1-benzylpiperidin-4-yl)ethyl]-1-(5-cyanopyridin-2-yl)-3-methylpiperidine-4-carboxamide | 446.2 |
| 10-80 | (3R)-N-[2-(1-benzylpiperidin-4-yl)ethyl]-3-methyl-1-[5-(trifluoromethyl)pyridin-2-yl]piperidine-4-carboxamide | 489.2 |
| 10-81 | (3R)-N-[2-(1-benzylpiperidin-4-yl)ethyl]-1-[3-fluoro-5-(trifluoromethyl)pyridin-2-yl]-3-methylpiperidine-4-carboxamide | 507.15 |

Example 11

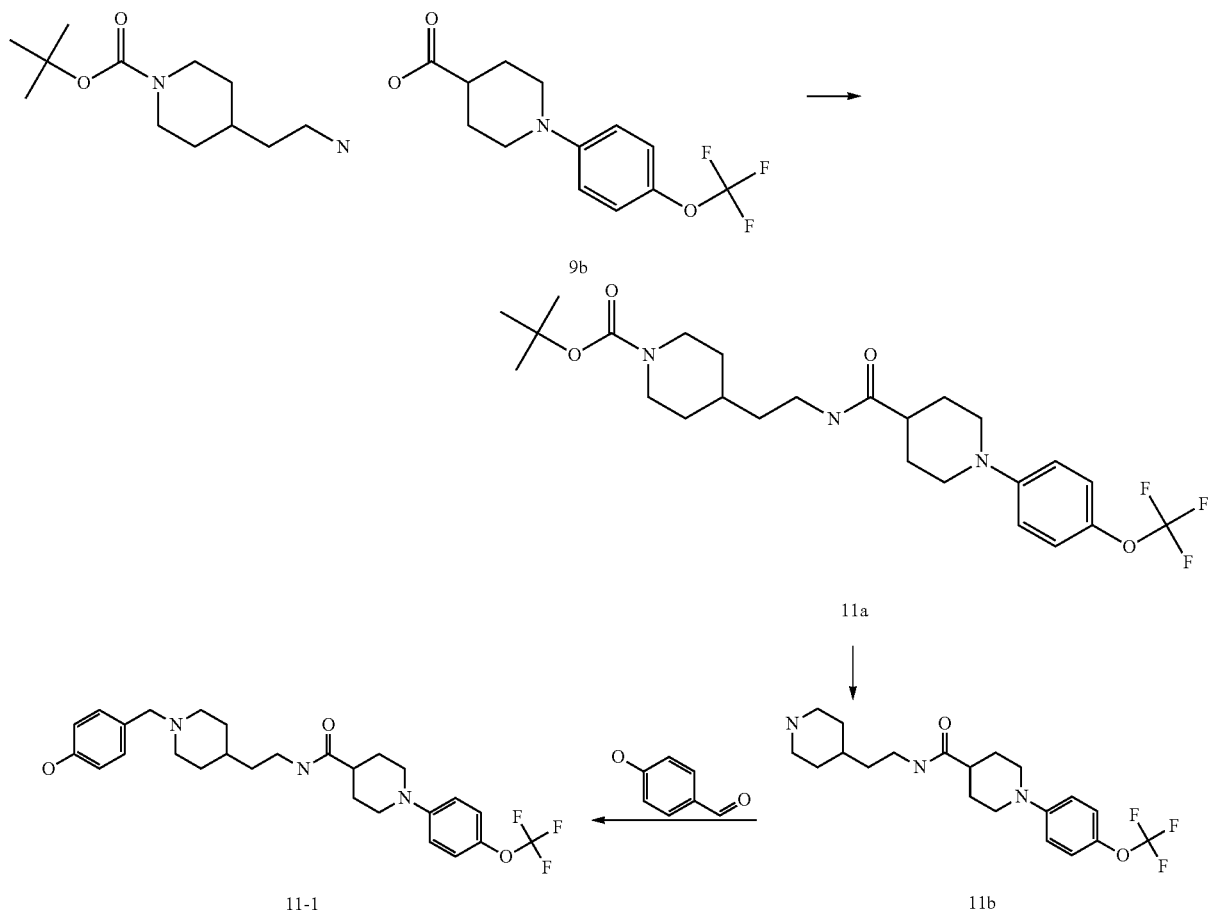

Step 11A: N-[2-(piperidin-4-yl)ethyl]-1-[4-(trifluoromethoxy)phenyl]piperidine-4-carboxamide To a solution of 1-[4-(trifluoromethoxy)phenyl]piperidine-4-carboxylic acid 9b (0.30 g, 1.0 mmol, 1.0 eq) and tert-butyl 4-(2-aminoethyl)piperidine-1-carboxylate (0.27 g, 1.2 mmol, 1.2 eq) in methylene chloride (5 mL) was added triethylamine (0.41 mL, 3.0 mmol, 3.0 eq) followed by HATU (0.46 g, 1.2 mmol, 1.2 eq) and the reaction was stirred at room temperature overnight. The reaction mixture was diluted with sat. NH₄Cl and extracted with methylene chloride. The combined organic layers were dried over MgSO₄ and concentrated. A silica gel column was loaded using methylene chloride and run using an increasing gradient of MeOH (0-5%) in methylene chloride over 20 min yielding tert-butyl 4-[2-({1-[4-(trifluoromethoxy)phenyl]piperidin-4-yl}formamido)ethyl]-piperidine-1-carboxylate 11a. The chromatographed 11a was dissolved in 20% TFA in methylene chloride (5 mL) and heated to 50° C. overnight. The reaction mixture was concentrated, dissolved in MeOH, and made basic with the addition of MP-carbonate. Following removal of the resin and concentration of the filtrate, the free base of N-[2-(piperidin-4-yl)ethyl]-1-[4-(trifluoromethoxy)phenyl]piperidine-4-carboxamide 11b was isolated as a foam.

Step 11B: N-(2-{1-[(4-hydroxyphenyl)methyl]piperidin-4-yl}ethyl)-1-[4-(trifluoromethoxy)phenyl]piperidine-4-carboxamide To NMP solutions of 11b (0.05 mL, 0.50 M, 1 eq) and 4-hydroxybenzaldehyde (0.05 mL, 0.50 M, 1 eq) was added an ethanolic solution of borane-pyridine complex (0.10 mL, 0.50 M, 2 eq) followed by acetic acid (5 μL) and the mixture stirred at RT overnight. The reaction was diluted to a total volume of 1 mL using MeOH and submitted directly for preparative chromatography yielding N-(2-{1-[(4-hydroxyphenyl)methyl]piperidin-4-yl}ethyl)-1-[4-(trifluoromethoxy)phenyl]piperidine-4-carboxamide 11-1. The table below provides the observed (Obs) ion m/z ratio for 11-1 (first compound listed in Table 9) and other compounds that were made according to the procedure as described in this example.

TABLE 9

| Cpd. No. | Compound Name | Obs Ion (m/z) |
| --- | --- | --- |
| 11-1 | N-(2-{1-[(4-hydroxyphenyl)methyl]piperidin-4-yl}ethyl)-1-[4-(trifluoromethoxy)phenyl]piperidine-4-carboxamide | 506.2 |
| 11-2 | N-(2-{1-[(2-fluoropyridin-3-yl)methyl]piperidin-4-yl}ethyl)-4-phenoxybenzamide | 434.3 |

TABLE 9-continued

| Cpd. No. | Compound Name | Obs Ion (m/z) |
|---|---|---|
| 11-3 | 4-(benzyloxy)-N-(2-{1-[(2-hydroxyphenyl)methyl]piperidin-4-yl}ethyl)benzamide | 445.2 |
| 11-4 | N-(2-{1-[(2-methyl-1,3-thiazol-4-yl)methyl]piperidin-4-yl}ethyl)-1-[4-(trifluoromethoxy)phenyl]piperidine-4-carboxamide | 511.2 |
| 11-5 | N-(2-{1-[(2-hydroxyphenyl)methyl]piperidin-4-yl}ethyl)-4-phenoxybenzamide | 431.2 |
| 11-6 | methyl 2-phenyl-2-{4-[2-({1-[4-(trifluoromethoxy)phenyl]piperidin-4-yl}formamido)ethyl]piperidin-1-yl}acetate | 548.2 |
| 11-7 | 4-(benzyloxy)-N-{2-[1-(2,3-dihydro-1,4-benzodioxin-5-ylmethyl)piperidin-4-yl]ethyl}benzamide | 487.2 |
| 11-8 | 1-(5-cyanopyridin-2-yl)-N-{2-[1-(cyclohexylmethyl)piperidin-4-yl]ethyl}piperidine-4-carboxamide | 438.2 |
| 11-9 | 4-(benzyloxy)-N-(2-{1-[(2-hydroxy-3-methoxyphenyl)methyl]piperidin-4-yl}ethyl)benzamide | 475.2 |
| 11-10 | N-(2-{1-[(4-hydroxyphenyl)methyl]piperidin-4-yl}ethyl)-4-phenoxybenzamide | 498.2 |
| 11-11 | N-{2-[1-(1,2,3-thiadiazol-4-ylmethyl)piperidin-4-yl]ethyl}-1-[4-(trifluoromethoxy)phenyl]piperidine-4-carboxamide | 520.3 |
| 11-12 | N-{2-[1-(2-hydroxy-1-phenylethyl)piperidin-4-yl]ethyl}-1-[4-(trifluoromethoxy)phenyl]piperidine-4-carboxamide | 448.3 |
| 11-13 | N-(2-{1-[(3-hydroxyphenyl)methyl]piperidin-4-yl}ethyl)-4-phenoxybenzamide | 431 |
| 11-14 | 4-(benzyloxy)-N-{2-[1-(1-phenylethyl)piperidin-4-yl]ethyl}benzamide | 443.3 |
| 11-15 | N-(2-{1-[(1-methyl-1H-pyrrol-2-yl)methyl]piperidin-4-yl}ethyl)-1-[4-(trifluoromethoxy)phenyl]piperidine-4-carboxamide | 493.3 |
| 11-16 | 1-(5-cyanopyridin-2-yl)-N-{2-[1-(2,3-dihydro-1,4-benzodioxin-5-ylmethyl)piperidin-4-yl]ethyl}piperidine-4-carboxamide | 490.2 |
| 11-17 | 1-(5-cyanopyridin-2-yl)-N-(2-{1-[(4-hydroxyphenyl)methyl]piperidin-4-yl}ethyl)piperidine-4-carboxamide | 448.3 |
| 11-18 | N-{2-[1-(2,3-dihydro-1,4-benzodioxin-5-ylmethyl)piperidin-4-yl]ethyl}-4-phenoxybenzamide | 473.3 |
| 11-19 | N-{2-[1-(3-methylbutyl)piperidin-4-yl]ethyl}-1-[4-(trifluoromethoxy)phenyl]piperidine-4-carboxamide | 430.1 |
| 11-20 | 4-(benzyloxy)-N-{2-[1-(pyridin-3-ylmethyl)piperidin-4-yl]ethyl}benzamide | 433.4 |
| 11-21 | N-{2-[1-(cyclohexylmethyl)piperidin-4-yl]ethyl}-1-[4-(trifluoromethoxy)phenyl]piperidine-4-carboxamide | 496.3 |
| 11-22 | N-{2-[1-(1H-indol-5-ylmethyl)piperidin-4-yl]ethyl}-1-[4-(trifluoromethoxy)phenyl]piperidine-4-carboxamide | 529.2 |
| 11-23 | N-{2-[1-(cyclohexylmethyl)piperidin-4-yl]-2-hydroxyethyl}-1-[4-(trifluoromethoxy)phenyl]piperidine-4-carboxamide | 512.3 |
| 11-24 | 4-(benzyloxy)-N-(2-{1-[(3-fluorophenyl)methyl]piperidin-4-yl}ethyl)benzamide | 446.9 |
| 11-25 | 1-(5-cyanopyridin-2-yl)-N-(2-{1-[(2-hydroxyphenyl)methyl]piperidin-4-yl}ethyl)piperidine-4-carboxamide | 448.3 |
| 11-26 | 1-(5-cyanopyridin-2-yl)-N-(2-{1-[(2-hydroxyphenyl)methyl]piperidin-4-yl}ethyl)piperidine-4-carboxamide | 447.5 |
| 11-27 | N-{2-[1-(2,2-dimethylpropyl)piperidin-4-yl]ethyl}-1-[4-(trifluoromethoxy)phenyl]piperidine-4-carboxamide | 435.3 |
| 11-28 | 4-phenoxy-N-{2-[1-(3-phenylpropyl)piperidin-4-yl]ethyl}benzamide | 431.2 |
| 11-29 | N-{2-[1-(2,3-dihydro-1-benzofuran-7-ylmethyl)piperidin-4-yl]ethyl}-1-[4-(trifluoromethoxy)phenyl]piperidine-4-carboxamide | 532.2 |
| 11-30 | N-(2-{1-[(6-methoxypyridin-2-yl)methyl]piperidin-4-yl}ethyl)-1-[4-(trifluoromethoxy)phenyl]piperidine-4-carboxamide | 521.1 |

Example 12

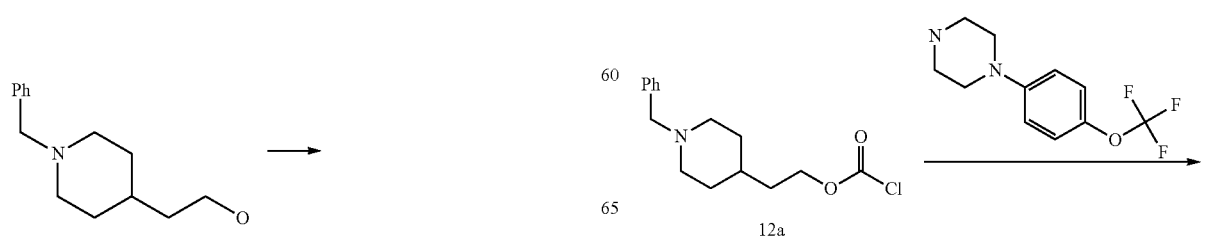

12a

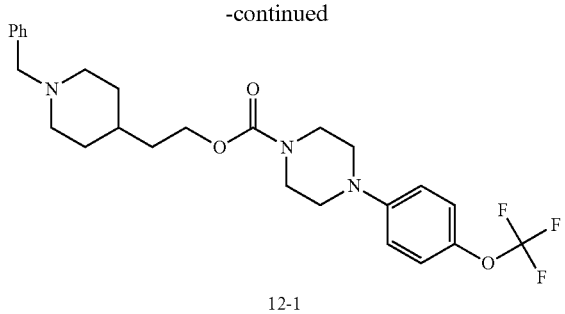

12-1

Step 12A: 2-(1-Benzylpiperidin-4-yl)ethyl chloroformate

A solution of 2-(1-benzylpiperidin-4-yl)ethan-1-ol (0.50 g, 2.3 mmol, 1.0 eq) and triphosgene (0.81 g, 2.7 mmol, 1.2 eq) in anhydrous THF (7 mL) was prepared and cooled to 0° C. Then, pyridine (0.27 g, 3.4 mmol, 1.5 eq) was added dropwise upon which a precipitate formed. After stirring for 20 min, the resulting suspension was filtered and concentrated to provide 2-(1-benzylpiperidin-4-yl)ethyl chloroformate 12a (0.40 g, 1.4 mmol, 62%) as an oil.

Step 12B: 2-(1-benzylpiperidin-4-yl)ethyl 4-[4-(trifluoromethoxy)phenyl]piperazine-1-carboxylate To a solution of 1-[4-(trifluoromethoxy)phenyl]piperazine 1f (0.10 g, 0.41 mmol, 1.0 eq) and 12a (0.13 g, 0.45 mmol, 1.1 eq) in methylene chloride (3 mL) was added triethylamine (0.17 mL, 1.2 mmol, 3.0 eq) and the reaction mixture stirred at RT. After 10 min, the reaction mixture was diluted with methylene chloride, washed with sat. NH$_4$Cl, dried over MgSO$_4$ and concentrated. A silica gel column was loaded using methylene chloride and run using an increasing gradient of MeOH (0-15%) in methylene chloride over 20 min to provide 2-(1-benzylpiperidin-4-yl)ethyl 4-[4-(trifluoromethoxy)phenyl]piperazine-1-carboxylate 12-1 (0.15 g, 0.31 mmol, 75%) as a foam. The table below provides the observed (Obs) ion m/z ratio for 12-1 (first compound listed in Table 10) and other compounds that were made according to the procedure as described in this example.

TABLE 10

| Cpd. No. | Compound Name | Obs Ion (m/z) |
| --- | --- | --- |
| 12-1 | 2-(1-benzylpiperidin-4-yl)ethyl 4-[4-(trifluoromethoxy)phenyl]piperazine-1-carboxylate | 492.2 |
| 12-2 | 2-(1-benzylpiperidin-4-yl)ethyl 4-(3-cyanophenyl)piperazine-1-carboxylate | 433.25 |
| 12-3 | 2-(1-benzylpiperidin-4-yl)ethyl 4-(4-fluorophenyl)piperazine-1-carboxylate | 426.3 |
| 12-4 | 2-(1-benzylpiperidin-4-yl)ethyl 4-[3-(trifluoromethoxy)phenyl]piperazine-1-carboxylate | 492.7 |
| 12-5 | 2-(1-benzylpiperidin-4-yl)ethyl N-[1-(3-cyanophenyl)piperidin-4-yl]carbamate | 447.3 |
| 12-6 | 2-(1-benzylpiperidin-4-yl)ethyl N-[1-(4-fluorophenyl)piperidin-4-yl]carbamate | 440.3 |
| 12-7 | 2-(1-benzylpiperidin-4-yl)ethyl 4-hydroxy-4-phenylpiperidine-1-carboxylate | 423.1 |
| 12-8 | 2-(1-benzylpiperidin-4-yl)ethyl 4-phenylpiperidine-1-carboxylate | 407.2 |
| 12-9 | 2-(1-benzylpiperidin-4-yl)ethyl 4-(3-cyano-5-fluorophenyl)piperazine-1-carboxylate | 451.2 |
| 12-10 | 2-(1-benzylpiperidin-4-yl)ethyl 4-(3-cyano-4-fluorophenyl)piperazine-1-carboxylate | 451.3 |
| 12-11 | 2-(1-benzylpiperidin-4-yl)ethyl N-{1-[4-(trifluoromethoxy)phenyl]piperidin-4-yl}carbamate | 506.2 |
| 12-12 | 2-(1-benzylpiperidin-4-yl)ethyl 4-(3,4,5-trifluorophenyl)piperazine-1-carboxylate | 462.2 |

Example 13

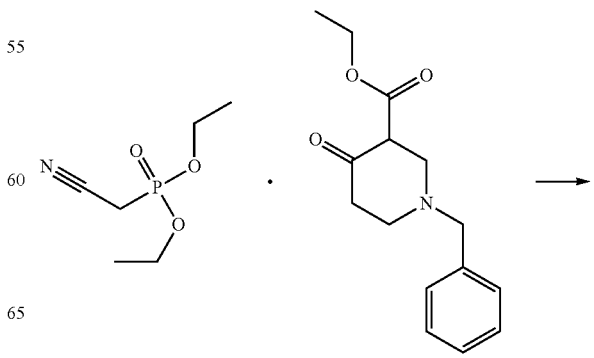

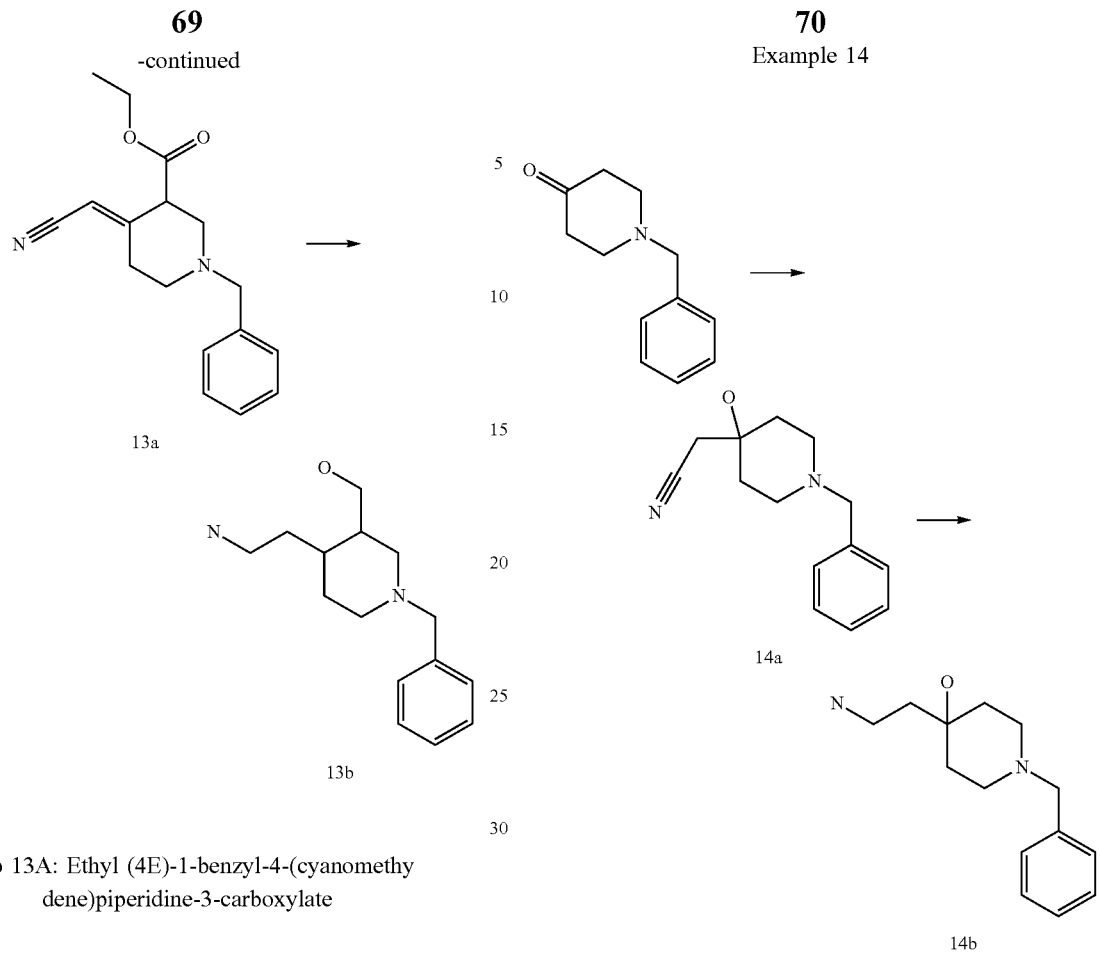

Step 13A: Ethyl (4E)-1-benzyl-4-(cyanomethy dene)piperidine-3-carboxylate

To a solution of diethyl cyanomethylphosphonate (0.5 g, 2.8 mmol, 1.2 eq) in anhydrous THF (5 mL) was added $K_2CO_3$ (0.4 g, 2.8 mmol, 1.2 eq) and the mixture was stirred at room temp for 15 min, then heated to reflux for 20 min. The mixture was cooled and ethyl 1-benzyl-4-oxopiperidine-3-carboxylate (0.6 g, 2.3 mmol, 1.0 eq) was added and refluxed for 12 hours. The mixture was cooled, diluted with EtOAc (10 mL) and washed with sat. $NaHCO_3$. The organic layer was dried over $MgSO_4$, filtered and concentrated. The crude product was purified by via ISCO chromatography with an increasing gradient from 0% to 60% EtOAc in hexanes. Two peaks were combined as they will merge on reduction to a racemic mixture to give ethyl (4E)-1-benzyl-4-(cyanomethylidene)piperidine-3-carboxylate 13a (0.4 g, 1.4 mmol, 50% yield).

Step 13B: [4-(2-aminoethyl)-1-benzylpiperidin-3-yl]methanol (4E)-1-benzyl-4-(cyanomethylidene)piperidine-3-carboxylate (0.4 g, 1.4 mmol, 1.0 eq) was dissolved in anhydrous THF (10 mL) and LAH (0.14 g, 4.23 mmol, 3.0 eq) was added and the mixture stirred for one hour. The reaction was quenched with $H_2O$ (0.5 mL) and diluted with EtOAc and filtered. The organic layer was concentrated to give [4-(2-aminoethyl)-1-benzylpiperidin-3-yl]methanol 13b (0.35 g, 1.4 mmol, 100% yield).

Example 14

Step 14A: 2-(1-benzyl-4-hydroxypiperidin-4-yl)acetonitrile n-BuLi (2 M in pentane, 7.3 mL, 1.1 eq) was added dropwise to solution of MeCN (0.76 mL) in THF (6 mL) at −78° C. and stirred 20 minutes. Next, a solution of 1-benzylpiperidine-4-one (2.5 g, 13.2 mmol, 1.0 eq) in 4 mL THF was added dropwise at −78° C. The reaction mixture was warmed to room temperature slowly overnight. The mixture was diluted with EtOAc and extracted from water. The crude product was purified via ISCO silica chromatography eluting with a gradient of 0% to 50% (80-18-2 $CHCl_3$/MeOH/$NH_3$) in DCM to give 2-(1-benzyl-4-hydroxypiperidin-4-yl)acetonitrile 14a (2.6 g, 11.4 mmol) in a 86% yield.

Step 14B: 4-(2-aminoethyl)-1-benzylpiperidin-4-ol 2-(1-Benzyl-4-hydroxypiperidin-4-yl)acetonitrile 14a (2.6 g, 11.4 mmol, 1.0 eq) was dissolved in anhydrous THF (30 mL) and LAH (1.1 g, 28 mmol, 2.5 eq) was added. The reaction mixture was stirred at room temp for 30 min then slowly quenched with water and excess EtOAc. The reaction was filtered through celite and concentrated to give 4-(2-aminoethyl)-1-benzylpiperidin-4-ol 14b (1.9 g, 7.9 mmol) in a 72% yield.

Example 15

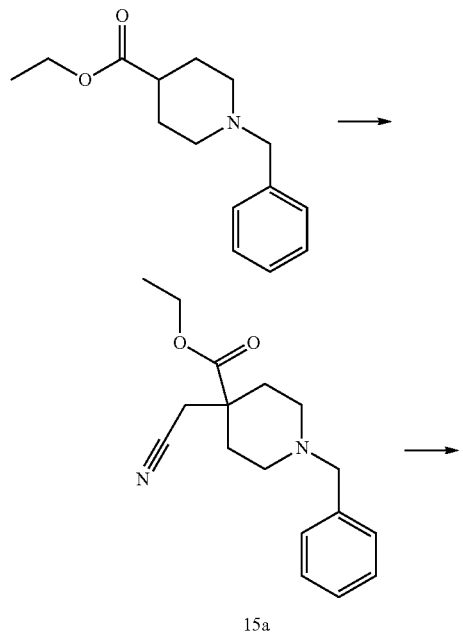

Step 15A: Ethyl 1-benzyl-4-(cyanomethyl)piperidine-4-carboxylate

Ethyl 1-benzylpiperidine-4-carboxylate (2.0 g, 8.1 mmol, 1.0 eq) was dissolved in anhydrous THF (20 mL) and cooled to −78° C. Next, LDA (2.0M in THF, 8.1 mL, 2.0 eq) was added dropwise and stirred for one hour at −78° C. A solution of bromoacetonitrile (1.9 g, 16.2 mmol, 2.0 eq) in THF (10 mL) was added dropwise at −78° C. and stirred at this temperature for 3 hours then warmed to room temperature. The reaction mixture was diluted with EtOAc and washed with sat. NH$_4$Cl and brine. The organic layer was dried over MgSO$_4$, filtered and concentrated. The crude product was purified via ISCO silica chromatography eluting with an increasing gradient of EtOAc (0% to 100%) in hexanes to give ethyl 1-benzyl-4-(cyanomethyl)piperidine-4-carboxylate 15a (1.3 g, 4.5 mmol) in a 56% yield.

Step 15B: [4-(2-Aminoethyl)-1-benzylpiperidin-4-yl]methanol

Ethyl 1-benzyl-4-(cyanomethyl)piperidine-4-carboxylate 15a (0.9 g, 3.1 mmol, 1.0 eq) was dissolved in anhydrous THF (10 mL) and LAH (0.21 g, 6.3 mmol, 2.0 eq) was added. The mixture was stirred at room temp for 30 min then slowly quenched with water and excess EtOAc. The reaction was filtered through celite and concentrated to give [4-(2-aminoethyl)-1-benzylpiperidin-4-yl]methanol 15b (0.77 g, 3.1 mmol) in a quantitative yield.

Example 16

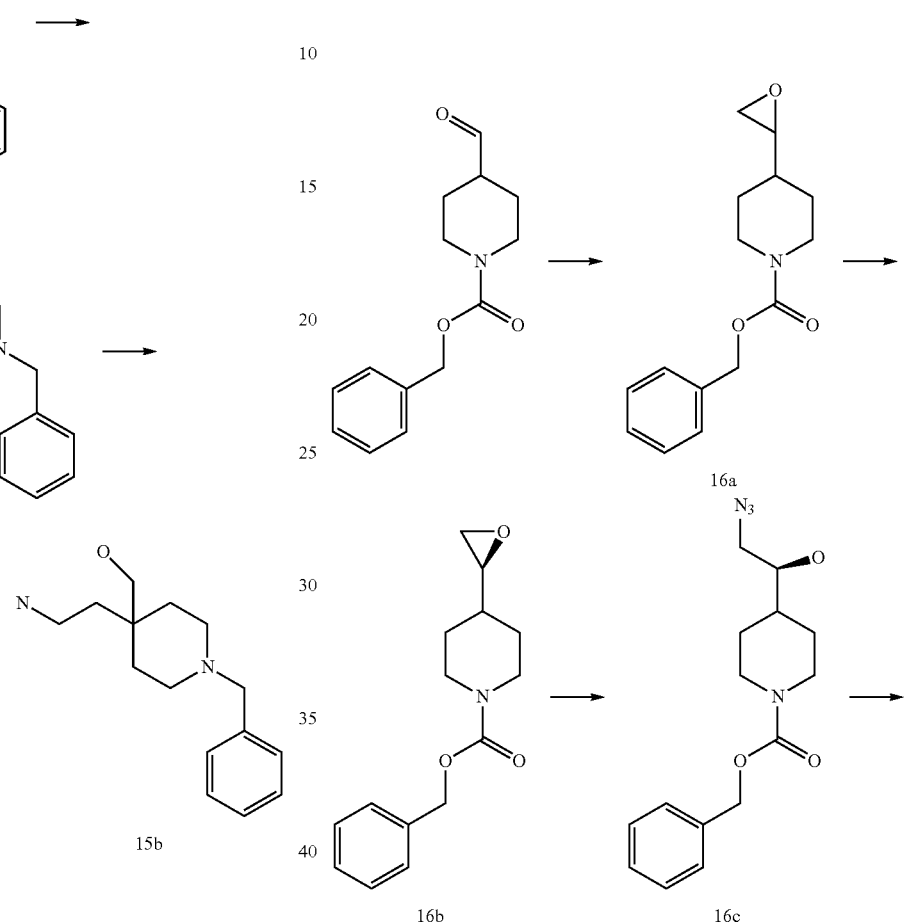

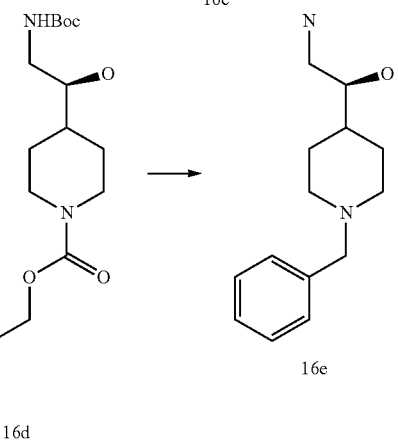

Step 16A: Benzyl 4-(oxiran-2-yl)piperidine-1-carboxylate

Trimethylsulfoxonium iodide (13.5 g, 60.7 mmol, 1.5 eq) was added in two portions to a solution of NaH (1.5 g, 60.7 mmol, 1.5 eq) in anhydrous DMSO (15 mL). This mixture was stirred for one hour at room temp. Then a solution of benzyl 4-formylpiperidine-1-carboxylate (10.0 g, 40.4 mmol, 1.0 eq) in anhydrous DMSO (20 mL) was added and the mixture stirred two hours. The reaction was poured into water and extracted twice with Et$_2$O. The organic layer was dried over MgSO$_4$, filtered, and concentrated. The crude product was purified on ISCO with 0% to 70% EtOAC in hexanes to give benzyl 4-(oxiran-2-yl)piperidine-1-carboxylate 16a as a clear oil (6.8 g, 26.1 mmol) in a 65% yield.

Step 16B: Benzyl 4-[(2S)-oxiran-2-yl]piperidine-1-carboxylate (S,S)-(+)-N,N'-Bis(3,5-di-tert-butylsalicylidene)-1,2-cyclohexanediaminocobalt(II) [88264-84-8] (0.40 g, 0.65 mmol, 0.02 eq) was dissolved in toluene (10 mL) and acetic acid (0.07 mL, 1.3 mmol, 0.04 eq) was added and the mixture stirred for one hour. The mixture was then concentrated and dried on a high vacuum to give a solid. Benzyl 4-(oxiran-2-yl)piperidine-1-carboxylate 16a (6.8 g, 26.1 mmol, 1.0 eq) was dissolved in anhydrous THF (15 mL) and the catalyst dissolved in minimal anhydrous THF was added and cooled to 0° C. and water (0.26 mL, 14.6 mmol, 0.6 eq) was added dropwise. The reaction slowly warmed to room temperature and stirred overnight. LCMS showed slow reaction so additional water (0.05 mL, 2.8 mmol, 0.1 eq) was added and the reaction was stirred overnight. The reaction mixture was concentrated and purified by ISCO column chromatography eluting with a gradient of 0% to 70% EtOAc in hexanes. Benzyl 4-[(2S)-oxiran-2-yl]piperidine-1-carboxylate 16b (3.4 g, 12.9 mmol) was determined to be 99% ee by chiral chromatography compared to the racemic mixture.

Step 16C: Benzyl 4-[(1S)-2-azido-1-hydroxyethyl]piperidine-1-carboxylate

Benzyl 4-[(2S)-oxiran-2-yl]piperidine-1-carboxylate 16b (3.4 g, 12.9 mmol, 1.0 eq) was dissolved in EtOH (9 mL) and water (1 mL) and sodium azide (1.7 g, 25.8 mmol, 2.0 eq) and ammonium chloride (1.4 g, 25.8 mmol, 2.0 eq) were added. The reaction mixture was heated to 55° C. and stirred overnight. EtOH was removed in vacuo and the reaction mixture was diluted with DCM and extracted from sat. NaHCO$_3$.

The organic layer was dried over MgSO$_4$, filtered and concentrated to give benzyl 4-R1S)-2-azido-1-hydroxyethyllpiperidine-1-carboxylate 16c (3.9 g, 12.7 mmol) in 98% yield.

Step 16D: Benzyl 4-[(1S)-2-[(tert-butoxy)carbonyl]amino}-1-hydroxyethyl]-piperidine-1-carboxylate Benzyl 4-[(1S)-2-azido-1-hydroxyethyl]piperidine-1-carboxylate 16c (3.9 g, 12.7 mmol, 1.0 eq) was dissolved in anhydrous MeOH (100 mL) then dichloronickel hexahydrate (3.0 g, 12.7 mmol, 1.0 eq) and NaBH$_4$ (0.96 g, 25.4 mmol, 2.0 eq) were added and the mixture stirred for one hour. MeOH was removed in vacuo and the product was redissolved in DCM, filtered through celite and concentrated. The crude product was then redissolved in DCM (100 mL) and triethylamine (5.3 mL, 38.1 mmol, 3.0 eq) and di-tert-butyl dicarbonate (5.5 g, 25.4 mmol, 3.0 eq) were added and the reaction was stirred overnight. An additional 0.2 equiv of TEA and di-tert-butyl dicarbonate were added along with MeOH (10 mL) for solubility and reaction stirred for one hour. Solvent was removed in vacuo and crude product redissolved in DCM and washed with sat. NH$_4$Cl. The organic layer was dried over MgSO$_4$, filtered and concentrated. The crude product was purified by ISCO column chromatography elution with a 0% to 100% of EtOAc in hexanes to afford benzyl 4-[(1S)-2-{[(tert-butoxy)carbonyl]amino}-1-hydroxyethyl]piperidine-1-carboxylate 16d (3.98 g, 10.5 mmol) in a 83% yield.

Step 16E: (1S)-2-amino-1-(1-benzylpiperidin-4-yl)ethan-1-ol

Benzyl 4-[(1S)-2-[(tert-butoxy)carbonyl]amino-1-hydroxyethyllpiperidine-1-carboxylate 16d (3.98 g, 10.5 mmol, 1.1 eq) was dissolved in MeOH and 10% Pd/C was added. The sealed vessel was purged with H$_2$ and the reaction was stirred one hour. The reaction was filtered through celite and concentrated to afford the crude amine which was used without further purification. The crude amine (2.4 g, 9.8 mmol, 1.0 eq) was dissolved in EtOH (75 mL) and acetic acid (0.55 mL, 10.5 mmol, 1.1 eq) and benzaldehyde (1.6 mL, 15.8 mmol, 1.6 eq) were added followed by sodium cyanoborohydride (1.0 g, 15.8 mmol, 1.6 eq) and the reaction was stirred for 2 hours Additional benzaldehyde (1.0 mL, 8.0 mmol) was added and reaction complete after one hour of stirring. The reaction mixture was quenched with water and MeOH was removed in vacuo. The reaction mixture was redissolved in DCM and extracted with sat. NaHCO$_3$ (2×). The organic layer was dried over MgSO$_4$ and filtered and concentrated. The crude product was purified by ISCO column chromatography eluting with a gradient of MeOH from 0% to 30% in DCM to yield the benzyl protected amine (3.1 g, 9.3 mmol) in a 95% yield. Next, the benzylamine (3.1 g, 9.3 mmol, 1.0 eq) was dissolved in DCM (50 mL) and TFA (10 mL) was added and the reaction mixture was stirred for one hour. The reaction mixture was concentrated and redissolved in MeOH and MP-carbonate resin was added until the solution was basic. The reaction was filtered and concentrated to afford (1S)-2-amino-1-(1-benzylpiperidin-4-yl)ethan-1-ol 16e (2.1 g, 9.0 mmol) in a 97% yield.

(1R)-2-Amino-1-(1-benzylpiperidin-4-yl)ethan-1-ol 16f was synthesized following the same overall procedure but using (R,R)-(+)-N,N'-Bis(3,5-di-tert-butylsalicylidene)-1,2-cyclohexanediaminocobalt(II) in Step 16B Example 17

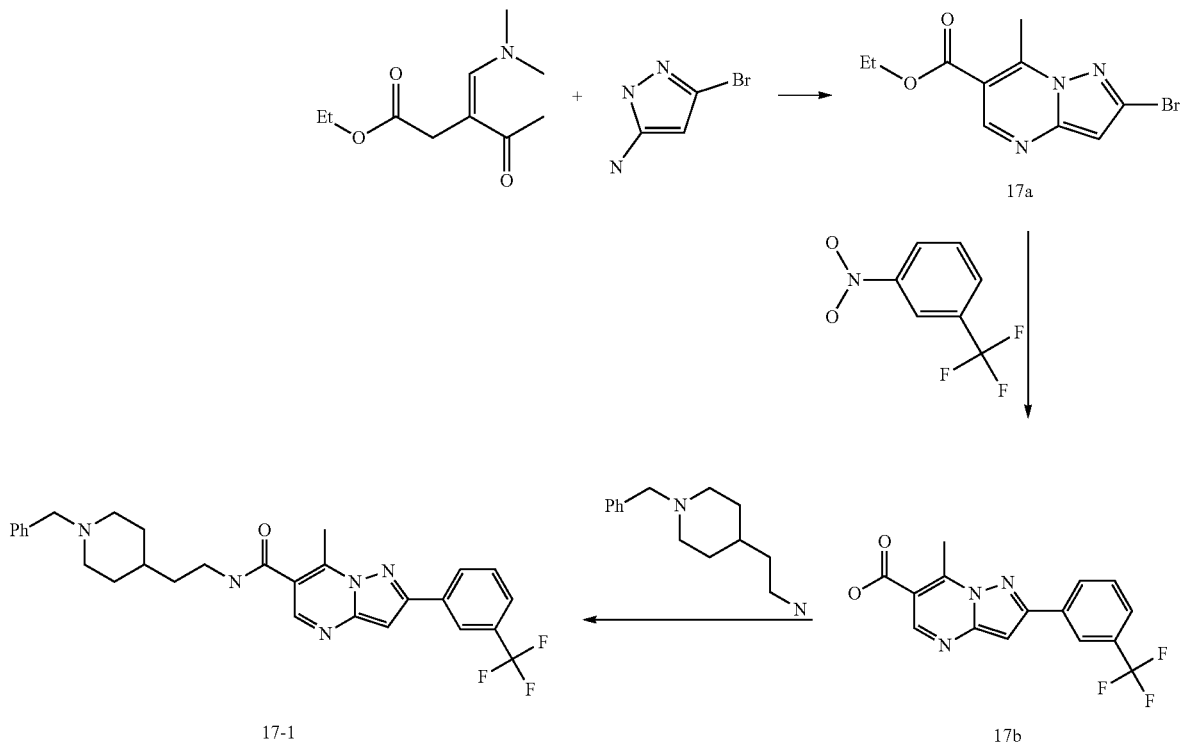

Step 17A: Ethyl 2-bromo-7-methylpyrazolo[1,5-a]pyrimidine-6-carboxylate

A solution of 3-bromo-1H-pyrazol-5-amine (4.2 g, 26 mmol, 1.0 eq) and ethyl (3Z)-3-[(dimethylamino)methylidene]-4-oxopentanoate (4.9 g, 26 mmol, 1.0 eq) in ethanol (300 mL) was prepared and heated to reflux for 2 hrs. The reaction mixture was concentrated. Silica gel column was loaded using methylene chloride and run using an increasing gradient of MeOH (0-5%) in methylene chloride over 20 min to provide ethyl 2-bromo-7-methylpyrazolo[1,5-a]pyrimidine-6-carboxylate 17a (6.0 g, 21 mmol, 81%) as a white solid.

Step 17B: 7-methyl-2-[3-(trifluoromethyl)phenyl]pyrazolo[1,5-a]pyrimidine-6-carboxylic acid To a solution of ethyl 2-bromo-7-methylpyrazolo[1,5-a]pyrimidine-6-carboxylate 17a (2.0 g, 7.0 mmol, 1.0 eq) in anhydrous dioxane (45 mL) was added [3-(trifluoromethyl)phenyl]boronic acid (2.0 g, 10 mmol, 1.5 eq) followed by aq. $K_2CO_3$ (7 mL, 22.5 mmol, 3.2 eq) and the resulting solution purged with nitrogen for 10 min. Then, [1,1'-Bis(diphenylphosphino)ferrocene]dichloropalladium(II) (0.52 g, 0.70 mmol, 0.1 eq) was added and the reaction heated to 90° C. overnight. The resulting dark reaction mixture was cooled, diluted heavily with EtOAc, and washed with brine. The organic layer was washed again with brine, dried over $Na_2SO_4$, and concentrated. Silica gel column (80 g) was loaded using methylene chloride and run using an increasing gradient of EtOAc (5-95%) in hexanes over 20 min. The chromatographed material was then suspended in MeOH (50 mL) and treated with an aq. solution of 1 M LiOH (5 mL). After stirring at RT overnight, the dark orange suspension was concentrated and the resulting solid re-dissolved in water. Then, the suspension was made acidic with careful addition of 6 M HCl. The precipitate was collected and dried to provide 7-methyl-2-[3-(trifluoromethyl)phenyl]pyrazolo[1,5-a]pyrimidine-6-carboxylic acid 17b (1.6 g, 4.9 mmol, 70% over two steps) as a tan solid.

Step 17C: N-[2-(1-benzylpiperidin-4-yl)ethyl]-7-methyl-2-[3-(trifluoromethyl)phenyl]pyrazolo[1,5-a]pyrimidine-6-carboxamide To a solution of 7-methyl-2-[3-(trifluoromethyl)phenyl]pyrazolo-[1,5-a]pyrimidine-6-carboxylic acid 17b (1.6 g, 4.9 mmol, 1.0 eq) and 2-(1-benzylpiperidin-4-yl)ethan-1- amine (1.1 g, 4.9 mmol, 1.0 eq) in NMP (20 mL) was added triethylamine (2.7 mL, 20 mmol, 4.0 eq) followed by HATU (1.9 g, 4.9 mmol, 1.0 eq) and the reaction stirred at room temperature overnight. The resulting dark reaction mixture was diluted heavily with EtOAc and washed repeatedly with brine. During the course of the extraction, a large amount of orange precipitate formed; thus after evaporating all organic solvent, the aqueous layers were left to sit overnight. Then, all precipitate was collected by vacuum filtration and washed with water. Silica gel column (120 g) was dry loaded and run using MeOH (0-20%) in DCM over 25 min to provide N-[2-(1-benzylpiperidin-4-yl)ethyl}-7-methyl-2-[3-(trifluoromethyl)phenyl]pyrazolo [1,5-a]pyrimidine-6-carboxamide 17-1 (1.5 g, 2.9 mmol, 59%) as an off-white solid. The table below provides the observed (Obs) ion m/z ratio for 17-1 (first compound listed in Table 11) and other compounds that were made according to the procedure as described in this example.

TABLE 11

| Cpd. No. | Compound Name | Obs Ion (m/z) |
|---|---|---|
| 17-1 | N-[2-(1-benzylpiperidin-4-yl)ethyl]-7-methyl-2-[3-(trifluoromethyl)phenyl]pyrazolo[1,5-a]pyrimidine-6-carboxamide | 522.2 |
| 17-2 | N-[2-(1-benzylpiperidin-4-yl)ethyl]-7-methyl-2-phenylpyrazolo[1,5-a]pyrimidine-6-carboxamide | 454.2 |
| 17-3 | N-[2-(1-benzyl-4-hydroxypiperidin-4-yl)ethyl]-7-methyl-2-[3-(trifluoromethyl)phenyl]pyrazolo[1,5-a]pyrimidine-6-carboxamide | 538.14 |
| 17-4 | N-[2-(1-benzylpiperidin-4-yl)ethyl]-2-(4-chlorophenyl)-7-methylpyrazolo[1,5-a]pyrimidine-6-carboxamide | 488.2 |
| 17-5 | N-[(2S)-2-(1-benzylpiperidin-4-yl)-2-hydroxyethyl]-7-methyl-2-[3-(trifluoromethyl)phenyl]pyrazolo[1,5-a]pyrimidine-6-carboxamide | 538.1 |
| 17-6 | N-[(2R)-2-(1-benzylpiperidin-4-yl)-2-hydroxyethyl]-7-methyl-2-[3-(trifluoromethyl)phenyl]pyrazolo[1,5-a]pyrimidine-6-carboxamide | 538.1 |
| 17-7 | N-[2-(1-benzylpiperidin-4-yl)ethyl]-7-methyl-2-(thiophen-2-yl)pyrazolo[1,5-a]pyrimidine-6-carboxamide | 460.3 |
| 17-8 | N-[2-(1-benzylpiperidin-4-yl)ethyl]-7-methyl-2-[4-(trifluoromethyl)phenyl]pyrazolo[1,5-a]pyrimidine-6-carboxamide | 522.2 |

Example 18

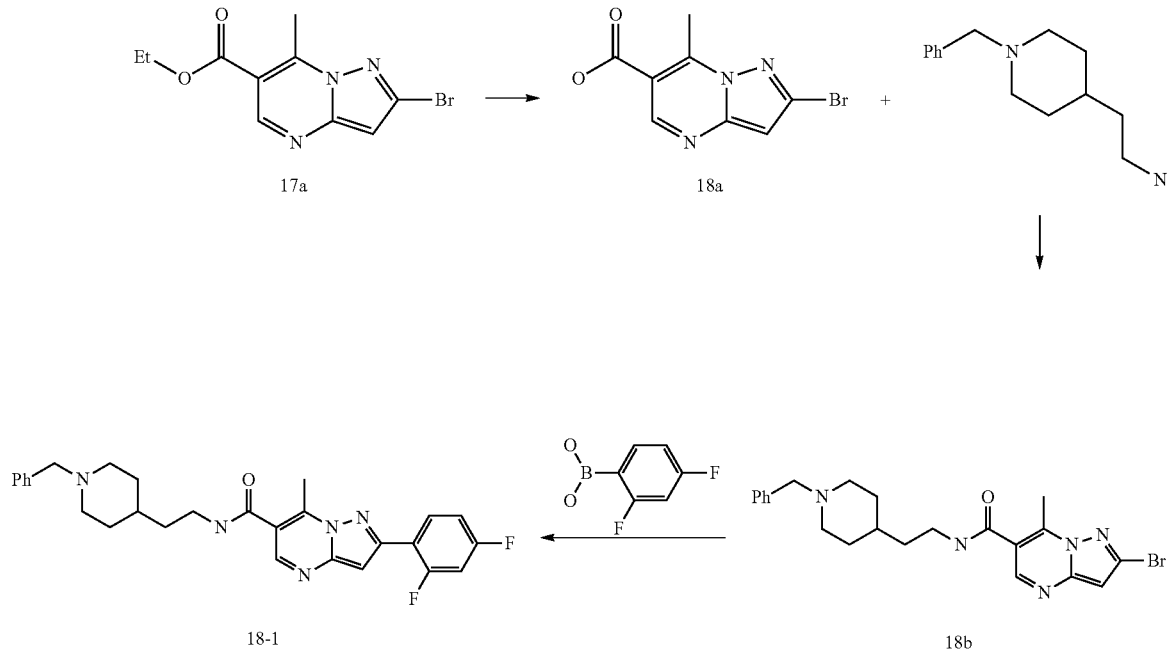

Step 18A: N-[2-(1-benzylpiperidin-4-yl)ethyl]-2-bromo-7-methylpyrazolo[1,5-a]pyrimidine-6-carboxamide To a solution of ethyl 2-bromo-7-methylpyrazolo[1,5-a]pyrimidine-6-carboxylate 17a (1.0 g, 3.6 mmol, 1.0 eq) in THF/water (4:1) was added solid NaOH (0.21 g, 5.3 mmol, 1.5 eq). After stirring at RT overnight, the organic solvent was concentrated and the remaining aqueous phase made acidic with careful addition of 6 M HCl. The resulting precipitate was collected and dried to provide 2-bromo-7-methylpyrazolo[1,5-a]pyrimidine-6-carboxylic acid 18a. A portion of this material (0.70 g, 2.7 mmol, 1.0 eq) together with 2-(1-benzylpiperidin-4-yl)ethan-1-amine (0.90 g, 4.1 mmol, 1.5 eq) in methylene chloride/DMF 2:1 (15 mL) was treated with triethylamine (1.5 mL, 11 mmol, 4.0 eq) and HATU (1.4 g, 3.6 mmol, 1.0 eq) and stirred at RT overnight. The reaction mixture was diluted with methylene chloride, washed with sat. $NH_4Cl$, dried over $MgSO_4$ and concentrated. Silica gel column was loaded using methylene chloride and run using an increasing gradient of MeOH (0-20%) in methylene chloride over 20 min to provide N-[2-(1-benzylpiperidin-4-yl)ethyl]-2-bromo-7-methylpyrazolo[1,5-a]pyrimidine-6-carboxamide 18b (1.1 g, 2.6 mmol, 94%).

Step 18B: N-[2-(1-benzylpiperidin-4-yl)ethyl]-2-(2,4-difluorophenyl)-7-methyl-pyrazolo[1,5-a]pyrimidine-6-carboxamide To an NMP solution of N-[2-(1-benzylpiperidin-4-yl)ethyl]-2-bromo-7-methylpyrazolo[1,5-a]pyrimidine-6-carboxamide 18b (0.20 mL, 0.13 M, 1.0 eq) was added a spatula tip of (2,4-difluorophenyl)boronic acid followed by aq. $K_3PO_4$ (0.05 mL, 1.5 M, 2.9 eq). Then, a generous spatula tip of PS-Pd(PPh$_3$) was added and the reaction mixture heated to 90° C. In general, this reaction and others of its kind are complete within 2 hrs, however additional PS-Pd (PPh$_3$) and/or longer reaction times can be used to push the coupling. The resulting dark suspension was cooled, passed through an HPLC filter, diluted to 1 mL using MeOH, and submitted for directly for preparative chromatography to yield N-[2-(1-benzylpiperidin-4-yl)ethyl]-2-(2,4-difluorophenyl)-7-methyl-pyrazolo[1,5-a]pyrimidine-6-carboxamide 18-1. The table below provides the observed (Obs) ion m/z ratio for 18-1 (first compound listed in Table 12) and other compounds that were made according to the procedure as described in this example.

TABLE 12

| Cpd. No. | Compound Name | Obs Ion (m/z) |
| --- | --- | --- |
| 18-1 | N-[2-(1-benzylpiperidin-4-yl)ethyl]-2-(2,4-difluorophenyl)-7-methylpyrazolo[1,5-a]pyrimidine-6-carboxamide | 490.15 |
| 18-2 | N-[2-(1-benzylpiperidin-4-yl)ethyl]-7-methyl-2-(pyridin-2-yl)pyrazolo[1,5-a]pyrimidine-6-carboxamide | 456.0 |
| 18-3 | N-[2-(1-benzylpiperidin-4-yl)ethyl]-2-(4-cyanophenyl)-7-methylpyrazolo[1,5-a]pyrimidine-6-carboxamide | 479.2 |
| 18-4 | N-[2-(1-benzylpiperidin-4-yl)ethyl]-2-(4-fluorophenyl)-7-methylpyrazolo[1,5-a]pyrimidine-6-carboxamide | 472.2 |
| 18-5 | N-[2-(1-benzylpiperidin-4-yl)ethyl]-2-(3,5-difluorophenyl)-7-methylpyrazolo[1,5-a]pyrimidine-6-carboxamide | 490.2 |
| 18-6 | N-[2-(1-benzylpiperidin-4-yl)ethyl]2-(3-fluorophenyl)-7-methylpyrazolo[1,5-a]pyrimidine-6-carboxamide | 472.2 |
| 18-7 | N-[2-(1-benzylpiperidin-4-yl)ethyl]-2-(2,3-difluorophenyl)-7-methylpyrazolo[1,5-a]pyrimidine-6-carboxamide | 490.2 |
| 18-8 | N-[2-(1-benzylpiperidin-4-yl)ethyl]-2-(3-cyanophenyl)-7-methylpyrazolo[1,5-a]pyrimidine-6-carboxamide | 479.1 |
| 18-9 | N-[2-(1-benzylpiperidin-4-yl)ethyl]-2-(2-methoxyphenyl)-7-methylpyrazolo[1,5-a]pyrimidine-6-carboxamide | 484.2 |
| 18-10 | N-[2-(1-benzylpiperidin-4-yl)ethyl]-2-(2,5-difluorophenyl)-7-methylpyrazolo[1,5-a]pyrimidine-6-carboxamide | 490.15 |
| 18-11 | N-[2-(1-benzylpiperidin-4-yl)ethyl]-7-methyl-2-[2-(trifluoromethyl)phenyl]pyrazolo[1,5-a]pyrimidine-6-carboxamide | 522.1 |
| 18-12 | N-[2-(1-benzylpiperidin-4-yl)ethyl]-2-(4-cyano-3-fluorophenyl)-7-methylpyrazolo[1,5-a]pyrimidine-6-carboxamide | 497.2 |
| 18-13 | N-[2-(1-benzylpiperidin-4-yl)ethyl]-7-methyl-2-[4-(trifluoromethoxy)phenyl]pyrazolo[1,5-a]pyrimidine-6-carboxamide | 538.2 |
| 18-14 | N-[2-(1-benzylpiperidin-4-yl)ethyl]-2-(2-methoxypyridin-3-yl)-7-methylpyrazolo[1,5-a]pyrimidine-6-carboxamide | 485.3 |
| 18-15 | N-[2-(1-benzylpiperidin-4-yl)ethyl]-2-(6-fluoropyridin-3-yl)-7-methylpyrazolo[1,5-a]pyrimidine-6-carboxamide | 473.1 |
| 18-16 | N-[2-(1-benzylpiperidin-4-yl)ethyl]-7-methyl-2-[3-(trifluoromethoxy)phenyl]pyrazolo[1,5-a]pyrimidine-6-carboxamide | 538.1 |
| 18-17 | N-[2-(1-benzylpiperidin-4-yl)ethyl]-7-methyl-2-(3,4,5-trifluorophenyl)pyrazolo[1,5-a]pyrimidine-6-carboxamide | 508.1 |
| 18-18 | N-[2-(1-benzylpiperidin-4-yl)ethyl]-2-(2-fluoropyridin-3-yl)-7-methylpyrazolo[1,5-a]pyrimidine-6-carboxamide | 473.2 |
| 18-19 | N-[2-(1-benzylpiperidin-4-yl)ethyl]-2-(6-methoxy-4-methylpyridin-3-yl)-7-methylpyrazolo[1,5-a]pyrimidine-6-carboxamide | 499.2 |
| 18-20 | N-[2-(1-benzylpiperidin-4-yl)ethyl]-2-(2-fluoropyridin-4-yl)-7-methylpyrazolo[1,5-a]pyrimidine-6-carboxamide | 473.2 |

Example 19

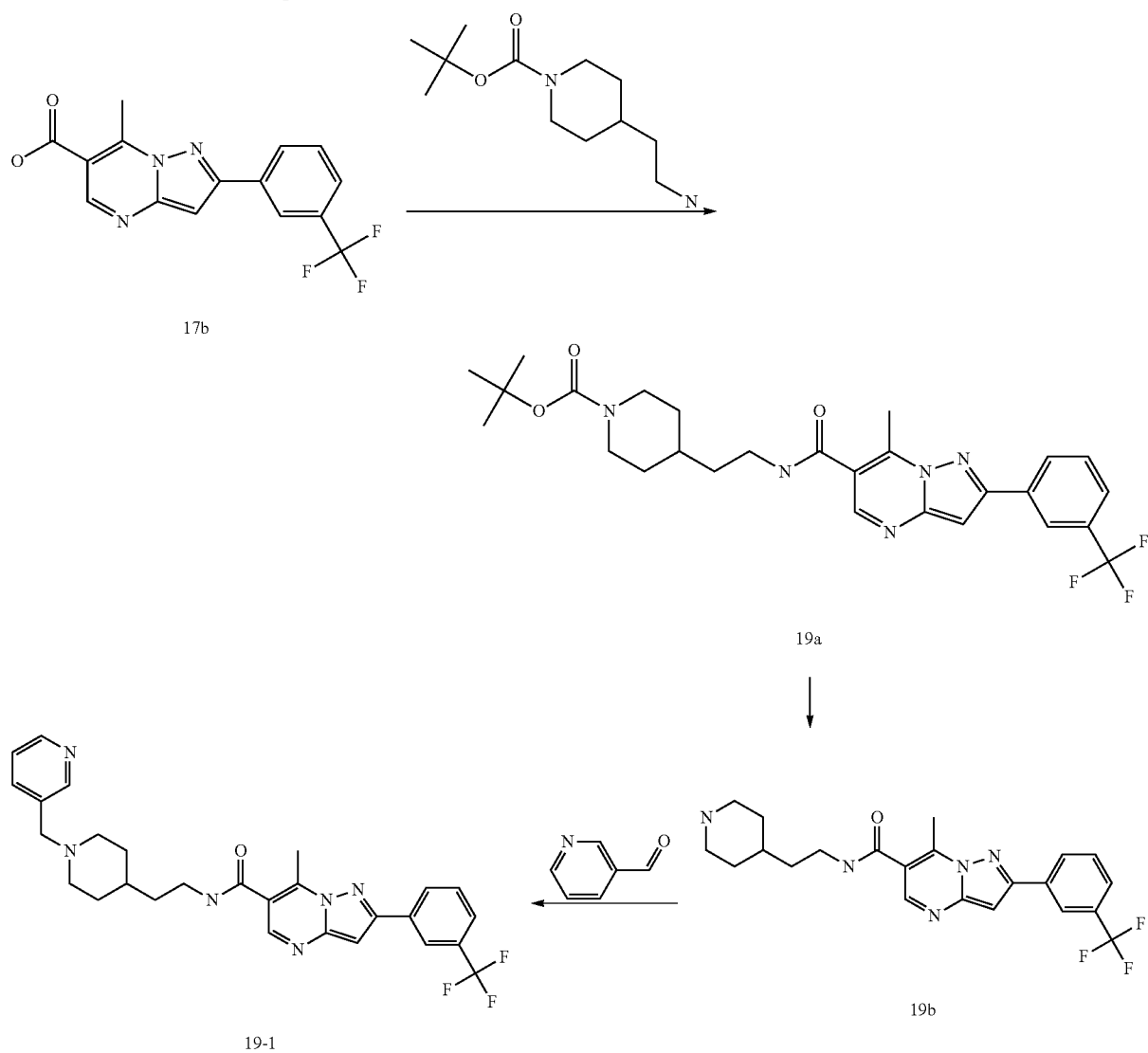

Step 19A: 7-methyl-N-[2-(piperidin-4-yl)ethyl]-2-[3-(trifluoromethyl)phenyl]pyrazolo[1,5-a]pyrimidine-6-carboxamide To a solution of 7-methyl-2-[3-(trifluoromethyl)phenyl]pyrazolo[1,5-a]pyrimidine-6-carboxylic acid 17b (0.09 g, 0.27 mmol, 1.0 eq) and tert-butyl 4-(2-aminoethyl)piperidine-1-carboxylate (0.07 g, 0.32 mmol, 1.2 eq) in methylene chloride was added triethylamine (0.11 mL, 0.81 mmol, 3.0 eq) followed by HATU (0.12 g, 0.32 mmol, 1.2 eq) and the reaction stirred at room temperature overnight. The reaction mixture diluted with sat. NH₄Cl and extracted with methylene chloride. The combined organic layers were dried over MgSO₄ and concentrated. Silica gel column was loaded using methylene chloride and run using an increasing gradient of MeOH (0-10%) in methylene chloride yielding tert-butyl 4-[2-({7-methyl-2-[3-(trifluoromethyl)phenyl]pyrazolo[1,5-a]pyrimidin-6-yl}formamido)ethyl]piperidine-1-carboxylate 19a. The chromatographed 19a was dissolved in 20% TFA in methylene chloride and stirred at RT overnight. The reaction mixture was concentrated, dissolved in MeOH, and made basic with the addition of MP-carbonate. Following removal of the resin and concentration of the filtrate, the free base of 7-methyl-N-[2-(piperidin-4-yl)ethyl]-1-2-[3-(trifluoromethyl)phenyl]pyrazolo[1,5-a]pyrimidine-6-carboxamide 19b (0.08 g, 0.19 mmol, 70% over two steps) was isolated as an oil.

Step 19B: 7-methyl-N-{2-[1-(pyridin-3-ylmethyl)piperidin-4-yl]ethyl}-2-[3-(trifluoromethyl)phenyl]pyrazolo[1,5-a]pyrimidine-6-carboxamide To NMP solutions of 7-methyl-N-[2-(piperidin-4-yl)ethyl]-2-[3-(trifluoromethyl)phenyl]pyrazolo[1,5-a]pyrimidine-6-carboxamide 19b (0.05 mL, 0.50 M, 1 eq) and pyridine-3-carbaldehyde (0.05 mL, 0.50 M, 1 eq) was added an ethanolic solution of borane-pyridine complex (0.10 mL, 0.50 M, 2 eq) followed by acetic acid (5 μL) and the mixture stirred at RT overnight. The reaction was diluted to a total volume of 1 mL using MeOH and submitted directly for preparative chromatography yielding 7-methyl-N-{2-[1-(pyridin-3-ylmethyl)piperidin-4-yl]ethyl}-2-[3-(trifluoromethyl)phenyl]pyrazolo[1,5-a]pyrimidine-6-carboxamide 19-1. The table below provides the observed (Obs) ion m/z ratio for 19-1 (first compound listed in Table 13) and other compounds that were made according to the procedure as described in this example.

TABLE 13

| Cpd. No. | Compound Name | Obs Ion (m/z) |
|---|---|---|
| 19-1 | 7-methyl-N-{2-[1-(pyridin-3-ylmethyl)piperidin-4-yl]ethyl}-2-[3-(trifluoromethyl)phenyl]pyrazolo[1,5-a]pyrimidine-6-carboxamide | 523.1 |
| 19-2 | N-{2-[1-(2,3-dihydro-1,4-benzodioxin-5-ylmethyl)piperidin-4-yl]ethyl}-7-methyl-2-phenylpyrazolo[1,5-a]pyrimidine-6-carboxamide | 512.2 |
| 19-3 | N-{2-[1-(cyclohexylmethyl)piperidin-4-yl]ethyl}-7-methyl-2-[3-(trifluoromethyl)phenyl]pyrazolo[1,5-a]pyrimidine-6-carboxamide | 528.2 |
| 19-4 | N-(2-{1-[(2-hydroxyphenyl)methyl]piperidin-4-yl}ethyl)-7-methyl-2-phenylpyrazolo[1,5-a]pyrimidine-6-carboxamide | 470.1 |
| 19-5 | 7-methyl-N-{2-[1-(pyridin-4-ylmethyl)piperidin-4-yl]ethyl}-2-[3-(trifluoromethyl)phenyl]pyrazolo[1,5-a]pyrimidine-6-carboxamide | 523.2 |
| 19-6 | 7-methyl-N-{2-[1-(pyridin-2-ylmethyl)piperidin-4-yl]ethyl}-2-[3-(trifluoromethyl)phenyl]pyrazolo[1,5-a]pyrimidine-6-carboxamide | 523.2 |
| 19-7 | N-(2-{1-[(3-methoxyphenyl)methyl]piperidin-4-yl}ethyl)-7-methyl-2-phenylpyrazolo[1,5-a]pyrimidine-6-carboxamide | 484.3 |
| 19-8 | N-(2-{1-[(4-hydroxyphenyl)methyl]piperidin-4-yl}ethyl)-7-methyl-2-phenylpyrazolo[1,5-a]pyrimidine-6-carboxamide | 470.2 |

Example 20

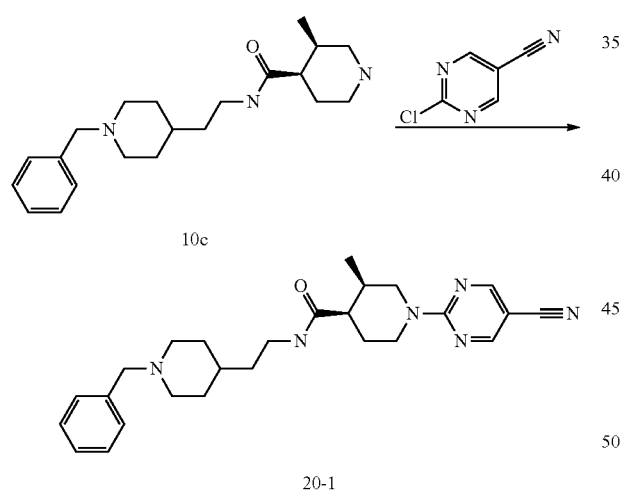

Step 20A: (3R)—N-[2-(1-benzylpiperidin-4-yl)ethyl]-1-(5-cyanopyrimidin-2-yl)-3-methylpiperidine-4-carboxamide To NMP solutions of (3R,4R)—N-[2-(1-benzylpiperidin-4-yl)ethyl]-3-methylpiperidine-4-carboxamide 10c (0.05 mL, 0.50 M, 1 eq) and 2-chloro-5-cyanopyrimidine (0.025 mmol, 1 eq) was added a NMP solution of trimethylamine (0.100 mL, 1.0 M, 4 eq) and the mixture stirred at 100° C. overnight. The reaction was diluted to a total volume of 1 mL using MeOH and submitted directly for preparative chromatography yielding (3R)—N-[2-(1-benzylpiperidin-4-yl)ethyl]-1-(5-cyanopyrimidin-2-yl)-3-methylpiperidine-4-carboxamide 20-1. The table below provides the observed (Obs) ion m/z ratio for 20-1 (first compound listed in Table 13) and other compounds that were made according to the procedure as described in this example.

TABLE 14

| Cpd. No. | Compound Name | Obs Ion (m/z) |
|---|---|---|
| 20-1 | (3R)-N-[2-(1-benzylpiperidin-4-yl)ethyl]-1-(5-cyanopyrimidin-2-yl)-3-methylpiperidine-4-carboxamide | 447.2 |
| 20-2 | (3R)-N-[2-(1-benzylpiperidin-4-yl)ethyl]-3-methyl-1-[5-(trifluoromethyl)pyrimidin-2-yl]piperidine-4-carboxamide | 490.14 |
| 20-3 | (3R)-N-[2-(1-benzylpiperidin-4-yl)ethyl]-1-(5-chloropyrimidin-2-yl)-3-methylpiperidine-4-carboxamide | 456.1 |

Example 21

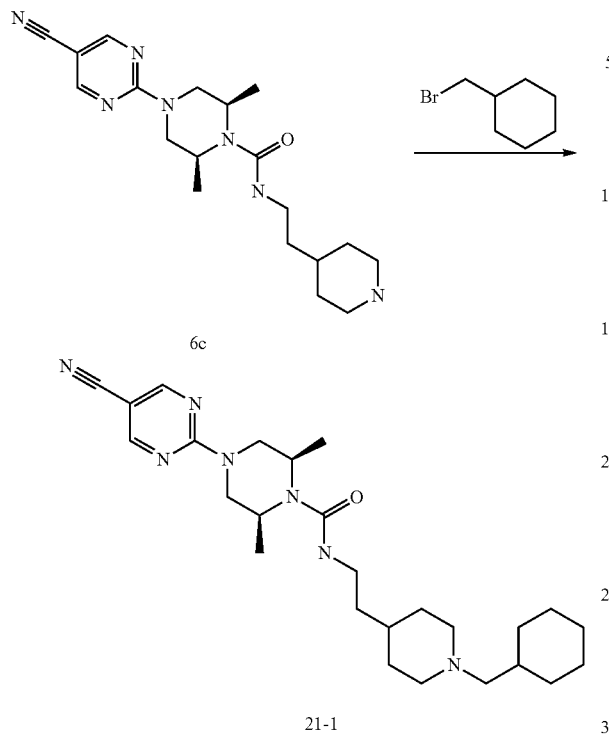

Step 21A: (2R,6S)-4-(5-cyanopyrimidin-2-yl)-N-{2-[1-(cyclohexylmethyl)piperidin-4-yl]ethyl-2,6-dimethyl piperazine-1-carboxamide To NMP solutions of (2S,6R)-4-(5-cyanopyrimidin-2-yl)-2,6-dimethyl-N-[2-(piperidin-4-yl)ethyl]piperazine-1-carboxamide 6c (0.20 mL, 0.12 M, 1.0 eq) and N,N-diisopropylethylamine (0.05 mL, 0.5 M, 4.0 eq) was added (bromomethyl)cyclohexane (4.4 mg, 0.025 mmol, 1.0 eq) and the reaction mixture heated at 50° C. overnight. The reaction mixture was diluted to a total volume of 1 mL using MeOH and submitted directly for preparative chromatography yielding (2R,6S)-4-(5-cyanopyrimidin-2-yl)-N-{2-[1-(cyclohexylmethyl)piperidin-4-yl]ethyl}-2,6-dimethylpiperazine-1-carboxamide 21-1. The table below provides the observed (Obs) ion m/z ratio for 21-1 (first compound listed in Table 15) and other compounds that were made according to the procedure as described in this example.

TABLE 15

| Cpd. No. | Compound Name | Obs Ion (m/z) |
| --- | --- | --- |
| 21-1 | (2R,6S)-4-(5-cyanopyrimidin-2-yl)-N-{2-[1-(cyclohexylmethyl)piperidin-4-yl]ethyl}-2,6-dimethylpiperazine-1-carboxamide | 468.1 |
| 21-2 | (2R,6S)-4-(5-cyanopyrimidin-2-yl)-2,6-dimethyl-N-(2-{1-[α,α-$^2$H-benzyl]piperidin-4-yl}ethyl)piperazine-1-carboxamide | 469.1 |
| 21-3 | (2R,6S)-4-(5-cyanopyrimidin-2-yl)-2,6-dimethyl-N-{2-[1-(pyridin-2-ylmethyl)piperidin-4-yl]ethyl}piperazine-1-carboxamide | 463.1 |
| 21-4 | (2R,6S)-4-(5-cyanopyrimidin-2-yl)-N-{2-[1-(2,3-dihydro-1H-inden-2-yl)piperidin-4-yl]ethyl}-2,6-dimethylpiperazine-1-carboxamide | 488.1 |
| 21-5 | (2R,6S)-4-(5-cyanopyrimidin-2-yl)-N-{2-[1-(cyclobutylmethyl)piperidin-4-yl]ethyl}-2,6-dimethylpiperazine-1-carboxamide | 440.4 |
| 21-6 | (2R,6S)-4-(5-cyanopyrimidin-2-yl)-2,6-dimethyl-N-{2-[1-(2-methylpropyl)piperidin-4-yl]ethyl}piperazine-1-carboxamide | 428.1 |
| 21-7 | (2R,6S)-4-(5-cyanopyrimidin-2-yl)-2,6-dimethyl-N-(2-{1-[2-(trimethylsilyl)ethyl]piperidin-4-yl}ethyl)piperazine-1-carboxamide | 472.1 |
| 21-8 | (2R,6S)-4-(5-cyanopyrimidin-2-yl)-2,6-dimethyl-N-{2-[1-(3-methylbutyl)piperidin-4-yl]ethyl}piperazine-1-carboxamide | 442.1 |
| 21-9 | (2R,6S)-4-(5-cyanopyrimidin-2-yl)-2,6-dimethyl-N-{2-[1-(oxan-2-ylmethyl)piperidin-4-yl]ethyl}piperazine-1-carboxamide | 470.1 |
| 21-10 | (2R,6S)-4-(5-cyanopyrimidin-2-yl)-2,6-dimethyl-N-(2-{1-[(3-methyloxetan-3-yl)methyl]piperidin-4-yl}ethyl)piperazine-1-carboxamide | 456.1 |
| 21-11 | (2R,6S)-4-(5-cyanopyrimidin-2-yl)-N-(2-{1-[(1,1-dioxo-1-thian-3-yl)methyl]piperidin-4-yl}ethyl)-2,6-dimethylpiperazine-1-carboxamide | 518.1 |
| 21-12 | (2R,6S)-N-[2-(1-{bicyclo[1.1.1]pentan-1-ylmethyl}piperidin-4-yl)ethyl]-4-(5-cyanopyrimidin-2-yl)-2,6-dimethylpiperazine-1-carboxamide | 452.1 |
| 21-13 | (2R,6S)-N-{2-[1-(cuban-1-ylmethyl)piperidin-4-yl]ethyl}-4-(5-cyanopyrimidin-2-yl)-2,6-dimethylpiperazine-1-carboxamide | 488.1 |
| 21-14 | (2R)-2-methyl-N-(2-{1-[α,α-$^2$H-benzyl]piperidin-4-yl}ethyl)-4-[5-(trifluoromethyl)pyrimidin-2-yl]piperazine-1-carboxamide | 493.1 |

TABLE 15-continued

| Cpd. No. | Compound Name | Obs Ion (m/z) |
|---|---|---|
| 21-15 | (2R,6S)-4-(5-cyanopyrimidin-2-yl)-2,6-dimethyl-N-(2-{1-[α,α-²H-benzyl]piperidin-4-yl}ethyl)piperazine-1-carboxamide | 464.2 |
| 21-16 | (2R)-4-[4-amino-5-(trifluoromethyl)pyrimidin-2-yl]-2-methyl-N-(2-{1-[α,α-²H-benzyl]piperidin-4-yl}ethyl)piperazine-1-carboxamide | 507.3 |
| 21-17 | (2R)-4-[4-amino-5-(trifluoromethyl)pyrimidin-2-yl]-2-methyl-N-(2-{1-[α,α-²H-benzyl]piperidin-4-yl}ethyl)piperazine-1-carboxamide | 512.3 |

Example 22

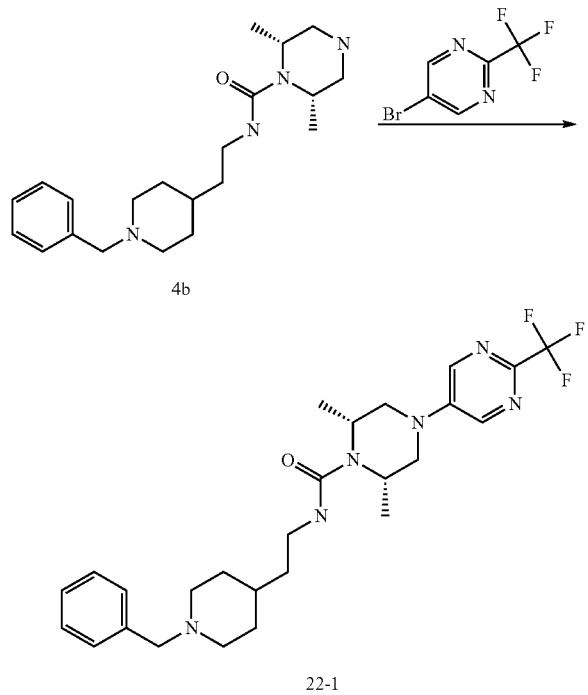

Step 22A: (2R,6S)—N-[2-(1-benzylpiperidin-4-yl)ethyl]-2,6-dimethyl-4-[2-(trifluoromethyl)pyrimidin-5-yl]piperazine-1-carboxamide To a solid mixture of (2S,6R)—N-[2-(1-benzylpiperidin-4-yl)ethyl]-2,6-dimethylpiperazine-1-carboxamide 4b (15 mg, 0.04 mmol, 1.0 eq), 5-bromo-2-(trifluoromethyl)pyrimidine (9.4 mg, 0.04 mmol, 1.0 eq), sodium tert-butoxide (11 mg, 0.12 mmol, 3.0 eq), and lastly bis(tri-tert-butylphosphine)palladium(0) (3.1 mg, 0.006 mmol, 0.15 eq) was added dioxane (1 mL) and reaction mixture stirred vigorously at 50° C. overnight. The resulting dark suspension was cooled, passed through an HPLC filter and concentrated in vacuo. The crude material was treated with 1.5 mL of MeOH, passed through an additional HPLC filter (leaving any precipitate behind), and purified by preparative chromatography yielding (2R,6S)—N-[2-(1-benzylpiperidin-4-yl)ethyl]-2,6-dimethyl-4-[2-(trifluoromethyl)pyrimidin-5-yl]piperazine-1-carboxamide 22-1. The table below provides the observed (Obs) ion m/z ratio for 22-1 (first compound listed in Table 16) and other compounds that were made according to the procedure as described in this example. For some less reactive halides, methanesulfanato (2-di-t-butylphosphino-2',4',6'-tri-i-propyl-1,1'-biphenyl)(2'amino-1,1'-biphenyl-2-yl) palladium (II) was used in place of bis(tri-tert-butylphosphine)palladium(0). These reactions were carried out at 100° C. for 1-2 hrs.

TABLE 16

| Cpd. No. | Compound Name | Obs Ion (m/z) |
|---|---|---|
| 22-1 | (2R,6S)-N-[2-(1-benzylpiperidin-4-yl)ethyl]-2,6-dimethyl-4-[2-(trifluoromethyl)pyrimidin-5-yl]piperazine-1-carboxamide | 505.1 |
| 22-2 | (2R,6S)-N-[2-(1-benzylpiperidin-4-yl)ethyl]-4-(4-cyanophenyl)-2,6-dimethylpiperazine-1-carboxamide | 460.1 |
| 22-3 | (2R,6S)-N-[2-(1-benzylpiperidin-4-yl)ethyl]-4-(4-cyano-2-fluorophenyl)-2,6-dimethylpiperazine-1-carboxamide | 478.1 |
| 22-4 | (2R,6S)-N-[2-(1-benzylpiperidin-4-yl)ethyl]-4-(4-cyano-3-fluorophenyl)-2,6-dimethylpiperazine-1-carboxamide | 478.1 |
| 22-5 | (2R,6S)-N-[2-(1-benzylpiperidin-4-yl)ethyl]-4-(3,5-difluoropyridin-2-yl)-2,6-dimethylpiperazine-1-carboxamide | 472.1 |
| 22-6 | (2R,6S)-N-[2-(1-benzylpiperidin-4-yl)ethyl]-2,6-dimethyl-4-(2,4,5-trifluorophenyl)piperazine-1-carboxamide | 489.2 |
| 22-7 | (2R,6S)-N-[2-(1-benzylpiperidin-4-yl)ethyl]-4-(3-chloro-4,5-difluorophenyl)-2,6-dimethylpiperazine-1-carboxamide | 505.1 |
| 22-8 | (2R,6S)-N-[2-(1-benzylpiperidin-4-yl)ethyl]-4-(6-chloro-5-fluoropyridin-3-yl)-2,6-dimethylpiperazine-1-carboxamide | 488.0 |
| 22-9 | (2R,6S)-N-[2-(1-benzylpiperidin-4-yl)ethyl]-4-(4-cyano-3,5-difluorophenyl)-2,6-dimethylpiperazine-1-carboxamide | 496.1 |
| 22-10 | (2R)-N-[2-(1-benzylpiperidin-4-yl)ethyl]-4-(4-cyano-2,5-difluorophenyl)-2-methylpiperazine-1-carboxamide | 482.1 |

TABLE 16-continued

| Cpd. No. | Compound Name | Obs Ion (m/z) |
|---|---|---|
| 22-11 | (2R)-N-[2-(1-benzylpiperidin-4-yl)ethyl]-4-(6-chloropyridin-3-yl)-2-methylpiperazine-1-carboxamide | 456.1 |
| 22-12 | (2R)-N-[2-(1-benzylpiperidin-4-yl)ethyl]-4-(4-cyano-3,5-difluorophenyl)-2-methylpiperazine-1-carboxamide | 482.1 |
| 22-13 | (2R)-N-[2-(1-benzylpiperidin-4-yl)ethyl]-4-(4-chloro-3,5-difluorophenyl)-2-methylpiperazine-1-carboxamide | 491.1 |
| 22-14 | (2R)-N-[2-(1-benzylpiperidin-4-yl)ethyl]-4-(4-chloro-3-fluorophenyl)-2-methylpiperazine-1-carboxamide | 473.1 |
| 22-15 | (2R)-N-[2-(1-benzylpiperidin-4-yl)ethyl]-4-(4-cyano-3-fluorophenyl)-2-methylpiperazine-1-carboxamide | 464.1 |
| 22-16 | (2R)-N-[2-(1-benzylpiperidin-4-yl)ethyl]-4-(2-methoxypyridin-4-yl)-2-methylpiperazine-1-carboxamide | 452.1 |
| 22-17 | (2R)-N-[2-(1-benzylpiperidin-4-yl)ethyl]-4-[4-cyano-3-(trifluoromethoxy)phenyl]-2-methylpiperazine-1-carboxamide | 530.1 |
| 22-18 | (2R)-N-[2-(1-benzylpiperidin-4-yl)ethyl]-4-(2-fluoropyridin-4-yl)-2-methylpiperazine-1-carboxamide | 440.1 |
| 22-19 | (2R)-N-[2-(1-benzylpiperidin-4-yl)ethyl]-2-methyl-4-(pyrimidin-5-yl)piperazine-1-carboxamide | 423.1 |
| 22-20 | (2R)-N-[2-(1-benzylpiperidin-4-yl)ethyl]-4-(2-methoxypyrimidin-5-yl)-2-methylpiperazine-1-carboxamide | 453.0 |
| 22-21 | (2R)-N-[2-(1-benzylpiperidin-4-yl)ethyl]-4-[2-(dimethylamino)pyrimidin-5-yl]-2-methylpiperazine-1-carboxamide | 466.3 |
| 22-22 | (2R)-N-[2-(1-benzylpiperidin-4-yl)ethyl]-2-methyl-4-[5-(trifluoromethyl)pyrazin-2-yl]piperazine-1-carboxamide | 491.1 |
| 22-23 | (2R,6S)-N-[2-(1-benzylpiperidin-4-yl)ethyl]-2,6-dimethyl-4-[5-(trifluoromethyl)pyrazin-2-yl]piperazine-1-carboxamide | 505.1 |
| 22-24 | (2R,6S)-N-[2-(1-benzylpiperidin-4-yl)ethyl]-4-(3-cyano-4-methoxyphenyl)-2,6-dimethylpiperazine-1-carboxamide | 490.1 |
| 22-25 | N-[2-(1-benzylpiperidin-4-yl)ethyl]-4-[5-(trifluoromethyl)pyrazin-2-yl]piperazine-1-carboxamide | 476.9 |
| 22-26 | (2R)-N-[2-(1-benzylpiperidin-4-yl)ethyl]-4-[4-cyano-3-(dimethylamino)phenyl]-2-methylpiperazine-1-carboxamide | 489.1 |
| 22-27 | (2R)-N-[2-(1-benzylpiperidin-4-yl)ethyl]-4-(5-cyanopyrazin-2-yl)-2-methylpiperazine-1-carboxamide | 448.1 |
| 22-28 | (2R)-N-[2-(1-benzylpiperidin-4-yl)ethyl]-4-(4-cyano-3-methoxyphenyl)-2-methylpiperazine-1-carboxamide | 476.0 |
| 22-29 | (2R)-N-[2-(1-benzylpiperidin-4-yl)ethyl]-2-methyl-4-[2-(trifluoromethyl)pyridin-4-yl]piperazine-1-carboxamide | 490.0 |
| 22-30 | (2R)-N-[2-(1-benzylpiperidin-4-yl)ethyl]-4-(2,6-difluoropyridin-4-yl)-2-methylpiperazine-1-carboxamide | 458.1 |
| 22-31 | (2R)-N-[2-(1-benzylpiperidin-4-yl)ethyl]-4-[4-cyano-3-(trifluoromethyl)phenyl]-2-methylpiperazine-1-carboxamide | 514.1 |
| 22-32 | (2R)-N-[2-(1-benzylpiperidin-4-yl)ethyl]-4-(4-cyano-3-fluoro-5-methoxyphenyl)-2-methylpiperazine-1-carboxamide | 494.1 |

Example 23

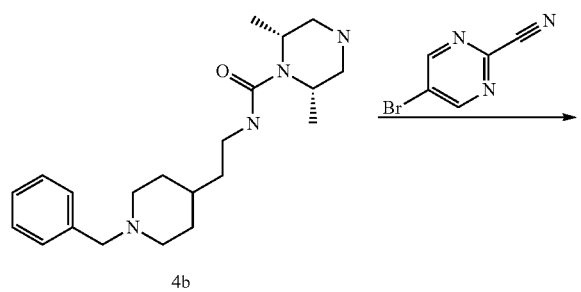

4b

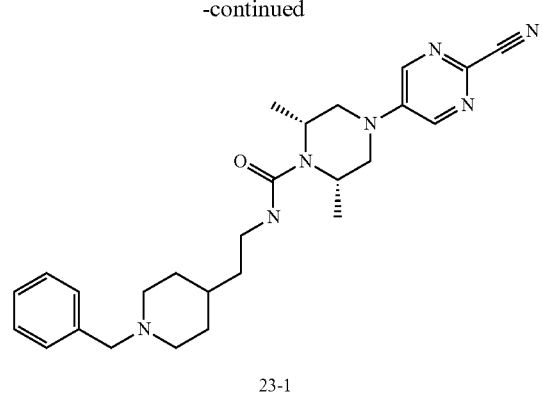

23-1

Step 23A: (2S,6R)—N-[2-(1-benzylpiperidin-4-yl)ethyl]-4-(2-cyanopyrimidin-5-yl)-2,6-dimethylpiperazine-1-carboxamide To a solid mixture of (2S,6R)—N-[2-(1-benzylpiperidin-4-yl)ethyl]-2,6-dimethylpiperazine-1-carboxamide 4b (30 mg, 0.08 mmol, 1.0 eq), 5-bromopyrimidine-2-carbonitrile (22 mg, 0.12 mmol, 1.5 eq) and cesium carbonate (39 mg, 0.12 mmol, 1.5 eq) was added NMP (1 mL) and reaction mixture stirred at 45° C. over the weekend. The resulting suspension was cooled, passed through an HPLC filter diluting to 1 mL with MeOH and submitted for directly for preparative chromatography yielding (2S,6R)—N-[2-(1-benzylpiperidin-4-yl)ethyl]-4-(2-cyanopyrimidin-5-yl)-2,6-dimethylpiperazine-1-carboxamide 23-1. The table below provides the observed (Obs) ion m/z ratio for 23-1 (first compound listed in Table 17) and other compounds that were made according to the procedure as described in this example.

TABLE 17

| Cpd. No. | Compound Name | Obs Ion (m/z) |
|---|---|---|
| 23-1 | (2S,6R)-N-[2-(1-benzylpiperidin-4-yl)ethyl]-4-(2-cyanopyrimidin-5-yl)-2,6-dimethylpiperazine-1-carboxamide | 462.2 |
| 23-2 | (2R,6S)-N-[2-(1-benzylpiperidin-4-yl)ethyl]-4-(5-cyanopyrazin-2-yl)-2,6-dimethylpiperazine-1-carboxamide | 462.1 |
| 23-3 | (2R,6S)-N-[2-(1-benzylpiperidin-4-yl)ethyl]-4-(6-cyanopyridazin-3-yl)-2,6-dimethylpiperazine-1-carboxamide | 462.1 | mmol, 5.0 eq) and reaction mixture stirred at room temperature overnight. The resulting suspension was filtered to remove triethylamine hydrochloride and concentrated to yield 2-[(3R,5R)-3,5-dimethylpiperazin-1-yl]pyrimidine-5-carbonitrile 24a as an orange solid. The crude material was carried to Example 26 without further purification.

Other compounds made using the above synthetic scheme include:

2-[(3R,5R)-3,5-dimethylpiperazin-1-yl]-5-(trifluoromethyl)pyrimidin-4-amine 24b;

2-[(3R,5R)-3,5-dimethylpiperazin-1-yl]-5-(trifluoromethyl)pyrimidine 24c; and

2-[(3S,5S)-3,5-dimethylpiperazin-1-yl]pyrimidine-5-carbonitrile 24d.

Example 24

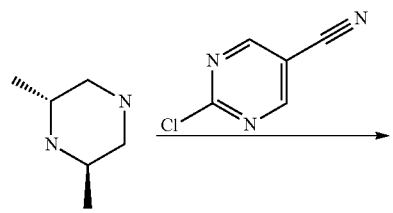

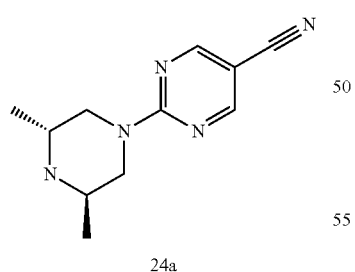

24a

Step 24A: 2-[(3R,5R)-3,5-dimethylpiperazin-1-yl]pyrimidine-5-carbonitrile

To a suspension of (2R,6R)-2,6-dimethylpiperazine dihydrochloride (0.250 g, 1.34 mmol, 1.0 eq) and 2-chloropyrimidine-5-carbonitrile (0.187 g, 1.34 mmol, 1.0 eq) in acetonitrile (5 mL) was added triethylamine (0.93 mL, 6.7

Example 25

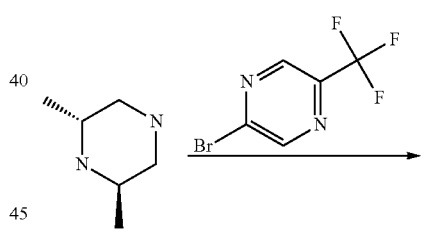

25a

Step 25A: 2-[(3R,5R)-3,5-dimethylpiperazin-1-yl]-5-(trifluoromethyl)pyrazine To a solid mixture of (2R,6R)-2,6-dimethylpiperazine dihydrochloride (0.08 g, 0.44 mmol, 1.0 eq), sodium tert-butoxide (0.21 g, 2.2 mmol, 5.0 eq) and bis(tri-tert-butylphosphine)palladium(0) (34 mg, 0.07 mmol, 0.15 eq) was added dioxane (4 mL) followed by 2-bromo-5-(trifluoromethyl)pyrazine (0.10 g, 0.44 mmol, 1.0 eq) and the reaction mixture stirred at 50° C. overnight. The resulting suspension was filtered thru a pad of celite using EtOAc and concentrated. Silica gel column (24 g) was loaded using methylene chloride and run using an increasing gradient of MeOH (0-20%) in methylene chloride over 25 min. Following concentration of the product eluents, 2-[(3R,5R)-3,5-dimethylpiperazin-1-yl]-5-(trifluoromethyl)pyrazine 25a (0.09 g, 0.33 mmol, 75%) was isolated as a yellow oil. The purified material was carried to Example 26.

5-[(3R,5R)-3,5-dimethylpiperazin-1-yl]-2-(trifluoromethyl)pyrimidine 25b was made in a similar fashion.

Example 26

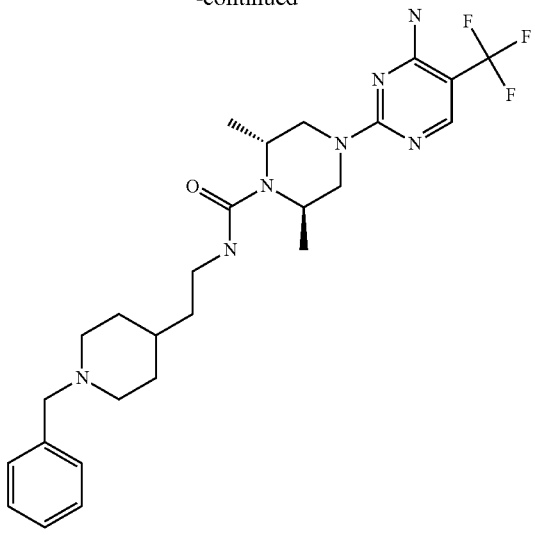

26-1

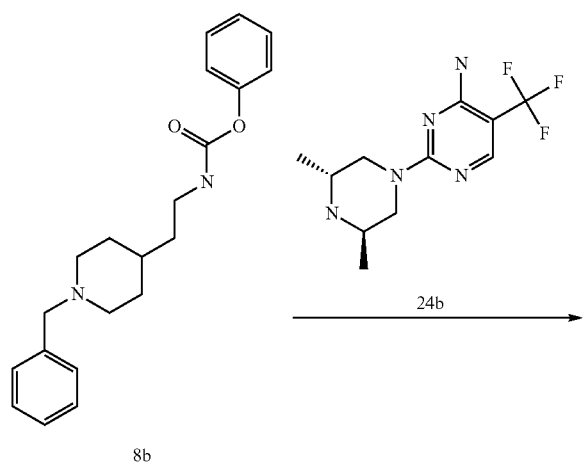

Step 26A: (2R,6R)-4-[4-amino-5-(trifluoromethyl)pyrimidin-2-yl]-N-[2-(1-benzylpiperidin-4-yl)ethyl]-2,6-dimethylpiperazine-1-carboxamide To a solution of phenyl N-[2-(1-benzylpiperidin-4-yl)ethyl]carbamate 8b (15 mg, 0.04 mmol, 1.0 eq) and crude 2-[(3R,5R)-3,5-dimethylpiperazin-1-yl]-5-(trifluoromethyl)pyrimidin-4-amine 24b (22 mg, 0.08 mmol, 2.0 eq) in NMP (0.50 mL) was added triethylamine (0.02 mL, 0.16 mmol, 4.0 eq) and reaction mixture stirred at 100° C. overnight. The reaction mixture was filtered and diluted to a total volume of 1 mL using MeOH and submitted directly for preparative chromatography yielding (2R,6R)-4-[4-amino-5-(trifluoromethyl)pyrimidin-2-yl]-N-[2-(1-benzylpiperidin-4-yl)ethyl]-2,6-dimethylpiperazine-1-carboxamide 26-1. The table below provides the observed (Obs) ion m/z ratio for 26-1 (first compound listed in Table 18) and other compounds that were made according to the procedure as described in this example.

TABLE 18

| Cpd. No. | Compound Name | Obs Ion (m/z) |
|---|---|---|
| 26-1 | (2R,6R)-4-[4-amino-5-(trifluoromethyl)pyrimidin-2-yl]-N-[2-(1-benzylpiperidin-4-yl)ethyl]-2,6-dimethylpiperazine-1-carboxamide | 520.1 |
| 26-2 | (2R,6R)-N-[2-(1-benzylpiperidin-4-yl)ethyl]-4-(5-cyanopyrimidin-2-yl)-2,6-dimethylpiperazine-1-carboxamide | 462.1 |
| 26-3 | (2S,6S)-N-[2-(1-benzylpiperidin-4-yl)ethyl]-4-(5-cyanopyrimidin-2-yl)-2,6-dimethylpiperazine-1-carboxamide | 462.1 |
| 26-4 | (2R,6R)-N-[2-(1-benzylpiperidin-4-yl)ethyl]-2,6-dimethyl-4-[5-(trifluoromethyl)pyrazin-2-yl]piperazine-1-carboxamide | 505.1 |
| 26-5 | (2R,6R)-N-[2-(1-benzylpiperidin-4-yl)ethyl]-2,6-dimethyl-4-[5-(trifluoromethyl)pyrimidin-2-yl]piperazine-1-carboxamide | 505.0 |
| 26-6 | (2R,6R)-N-[2-(1-benzylpiperidin-4-yl)ethyl]-2,6-dimethyl-4-[2-(trifluoromethyl)pyrimidin-5-yl]piperazine-1-carboxamide | 505.05 |

Example 27

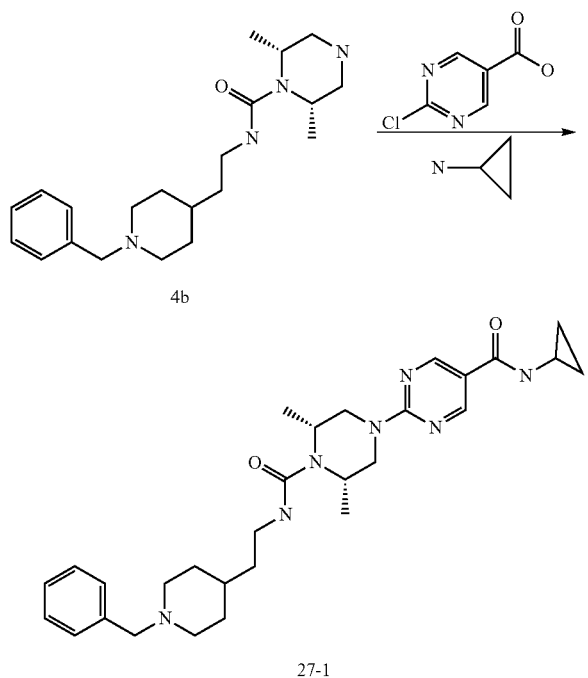

Step 27A: 2-[(3R,5S)-4-{[2-(1-benzylpiperidin-4-yl)ethyl]carbamoyl}-3,5-dimethylpiperazin-1-yl]-N-cyclopropylpyrimidine-5-carboxamide To a 0.5 M NMP solution of (2S,6R)—N-[2-(1-benzylpiperidin-4-yl)ethyl]-2,6-dimethylpiperazine-1-carboxamide 4b (1.0 mL, 0.50 mmol, 1.0 eq) and triethylamine (0.28 mL, 2.0 mmol, 4 eq) was added 2-chloropyrimidine-5-carboxylic acid (79 mg, 0.50 mmol, 1.0 eq) and the reaction mixture stirred at 50° C. overnight. Then, a 75 µA aliquot was treated with NMP solutions of cyclopropylamine (0.10 mL, 0.5 M, 1.3 eq), triethylamine (0.10 mL, 2.0 M, 5.2 eq) and HATU (0.10 mL, 0.5 M, 1.3 eq) and again stirred at 50° C. overnight. The reaction mixture was passed through an HPLC filter diluting to 1 mL with MeOH and purified by preparative chromatography yielding 2-[(3R,5S)-4-{[2-(1-benzylpiperidin-4-yl)ethyl]carbamoyl}-3,5-dimethylpiperazin-1-yl]-N-cyclopropylpyrimidine-5-carboxamide 27-1. The table below provides the observed (Obs) ion m/z ratio for 27-1 (first compound listed in Table 19) and other compounds that were made according to the procedure as described in this example.

TABLE 19

| Cpd. No. | Compound Name | Obs Ion (m/z) |
|---|---|---|
| 27-1 | 2-[(3R,5S)-4-{[2-(1-benzylpiperidin-4-yl)ethyl]carbamoyl}-3,5-dimethylpiperazin-1-yl]-N-cyclopropylpyrimidine-5-carboxamide | 520.1 |
| 27-2 | (2R,6S)-N-[2-(1-benzylpiperidin-4-yl)ethyl]-2,6-dimethyl-4-[5-(pyrrolidine-1-carbonyl)pyrimidin-2-yl]piperazine-1-carboxamide | 534.1 |
| 27-3 | 2-[(3R,5S)-4-{[2-(1-benzylpiperidin-4-yl)ethyl]carbamoyl}-3,5-dimethylpiperazin-1-yl]-N-methyl-N-(propan-2-yl)pyrimidine-5-carboxamide | 536.2 |
| 27-4 | 2-[(3R,5S)-4-{[2-(1-benzylpiperidin-4-yl)ethyl]carbamoyl}-3,5-dimethylpiperazin-1-yl]-N-(prop-2-en-1-yl)pyrimidine-5-carboxamide | 520.2 |
| 27-5 | 2-[(3R,5S)-4-{[2-(1-benzylpiperidin-4-yl)ethyl]carbamoyl}-3,5-dimethylpiperazin-1-yl]-N-(cyclopropylmethyl)pyrimidine-5-carboxamide | 534.2 |
| 27-6 | 2-[(3R,5S)-4-{[2-(1-benzylpiperidin-4-yl)ethyl]carbamoyl}-3,5-dimethylpiperazin-1-yl]-N-cyclobutylpyrimidine-5-carboxamide | 534.1 |
| 27-7 | 2-[(3R,5S)-4-{[2-(1-benzylpiperidin-4-yl)ethyl]carbamoyl}-3,5-dimethylpiperazin-1-yl]-N-(2-fluoroethyl)pyrimidine-5-carboxamide | 526.1 |
| 27-8 | 2-[(3R,5S)-4-{[2-(1-benzylpiperidin-4-yl)ethyl]carbamoyl}-3,5-dimethylpiperazin-1-yl]-N-(butan-2-yl)pyrimidine-5-carboxamide | 536.2 |
| 27-9 | 2-[(3R)-4-{[2-(1-benzylpiperidin-4-yl)ethyl]carbamoyl}-3-methylpiperazin-1-yl]-N-ethyl-N-methylpyrimidine-5-carboxamide | 508.3 |
| 27-10 | 2-[(3R)-4-{[2-(1-benzylpiperidin-4-yl)ethyl]carbamoyl}-3-methylpiperazin-1-yl]-N-methylpyrimidine-5-carboxamide | 480.3 |
| 27-11 | 2-[(3R)-4-{[2-(1-benzylpiperidin-4-yl)ethyl]carbamoyl}-3-methylpiperazin-1-yl]-6-methyl-N-(2-methylpropyl)pyrimidine-4-carboxamide | 536.3 |
| 27-12 | 2-[(3R)-4-{[2-(1-benzylpiperidin-4-yl)ethyl]carbamoyl}-3-methylpiperazin-1-yl]-N-(2-methylpropyl)pyrimidine-5-carboxamide | 522.3 |
| 27-13 | 2-[(3R)-4-{[2-(1-benzylpiperidin-4-yl)ethyl]carbamoyl}-3-methylpiperazin-1-yl]-6-methyl-N-(propan-2-yl)pyrimidine-4-carboxamide | 522.2 |
| 27-14 | 2-[(3R)-4-{[2-(1-benzylpiperidin-4-yl)ethyl]carbamoyl}-3-methylpiperazin-1-yl]-N-cyclopropyl-6-methylpyrimidine-4-carboxamide | 520.3 |
| 27-15 | 2-[(3R)-4-{[2-(1-benzylpiperidin-4-yl)ethyl]carbamoyl}-3-methylpiperazin-1-yl]-N-(propan-2-yl)pyrimidine-5-carboxamide | 508.3 |

TABLE 19-continued

| Cpd. No. | Compound Name | Obs Ion (m/z) |
|---|---|---|
| 27-16 | 2-[(3R)-4-{[2-(1-benzylpiperidin-4-yl)ethyl]carbamoyl}-3-methylpiperazin-1-yl]-N-ethylpyrimidine-5-carboxamide | 494.2 |
| 27-17 | 2-[(3R)-4-{[2-(1-benzylpiperidin-4-yl)ethyl]carbamoyl}-3-methylpiperazin-1-yl]-N,N-dimethylpyrimidine-5-carboxamide | 494.2 |
| 27-18 | 2-[(3R)-4-{[2-(1-benzylpiperidin-4-yl)ethyl]carbamoyl}-3-methylpiperazin-1-yl]-N-ethyl-N,6-dimethylpyrimidine-4-carboxamide | 522.3 |
| 27-19 | 2-[(3R)-4-{[2-(1-benzylpiperidin-4-yl)ethyl]carbamoyl}-3-methylpiperazin-1-yl]-N-ethyl-6-methylpyrimidine-4-carboxamide | 508.3 |

BIOLOGY EXAMPLES

Binding Assay

Binding affinity (Ki) of compounds was measured by inhibition of radioligand binding to membranes from CHO cells expressing human M1, M2, M3, M4 and M5 receptors. Membranes were prepared by nitrogen cavitation and differential centrifugation as previously described (Hoare et al., Mol. Pharmacol. 2003 March; 63(3): 751-65). The radioligand employed was tritiated N-methylscopolamine, used at a concentration of 1.5 nM. A dose-response of twelve concentrations of compound was used, ranging from 10 µM to 32 µM. The assay buffer was 50 mM HEPES, 100 mM NaCl, 5 mM $MgCl_2$, 1 mM ethylenediaminetetraacetic acid, pH-adjusted to pH 7.4. Membranes, radioligand and compound were incubated together for 90 minutes at 37° C., in a total volume of 150 µl in a 96-well plate. Receptor-bound radioligand was then collected by harvesting the assay over glass fiber filters pretreated with polyethylenimine to trap the cell membranes, using rapid vacuum filtration. Harvesting and radioactivity counting was conducted as previously described (see, e.g., Hoare et al., *Mol. Pharmacol.* 2003 63(3):751-65); Erratum at *Mol. Pharmacol.* 2005 July; 68(1): 260).

Binding affinities of all the exemplified compounds, which are described in the examples and listed in the tables above, are less than 1 µM against the M4 receptor. More specifically, specificity for the M4 receptor for each of the compounds listed in Table 20 is as follows: (1) "+" means the compound had a Ki against the M4 receptor of less than 1 µM (1,000 nM) but greater or equal to 100 nM; (2) "++" means the compound had a Ki against the M4 receptor of less than 100 nM but greater or equal to 10 nM; and (3) "+++" means that the compound had a Ki against the M4 receptor of less than 10 nM.

TABLE 20

| Cpd. No. | Ki |
|---|---|
| 3-1 | +++ |
| 3-2 | ++ |
| 3-3 | + |
| 3-4 | + |
| 3-5 | +++ |
| 3-6 | ++ |
| 3-7 | ++ |
| 3-8 | +++ |
| 3-9 | +++ |
| 3-10 | +++ |
| 3-11 | +++ |
| 3-12 | +++ |
| 3-13 | +++ |
| 3-14 | +++ |
| 3-15 | ++ |
| 3-16 | +++ |
| 3-17 | +++ |
| 3-18 | +++ |
| 3-19 | +++ |
| 3-20 | ++ |
| 3-21 | +++ |
| 3-22 | +++ |
| 3-23 | +++ |
| 4-1 | +++ |
| 4-2 | + |
| 4-4 | + |
| 4-5 | +++ |
| 4-6 | +++ |
| 4-8 | + |
| 4-9 | + |
| 4-10 | +++ |
| 4-11 | +++ |
| 4-12 | +++ |
| 4-13 | +++ |
| 4-14 | +++ |
| 4-15 | +++ |
| 4-16 | +++ |
| 4-17 | +++ |
| 4-18 | +++ |
| 4-19 | +++ |
| 4-20 | +++ |
| 4-21 | +++ |
| 4-22 | +++ |
| 4-23 | + |
| 4-24 | ++ |
| 4-25 | ++ |
| 4-26 | ++ |
| 4-27 | ++ |
| 4-28 | ++ |
| 4-28 | ++ |
| 4-30 | ++ |
| 4-31 | ++ |
| 4-33 | ++ |
| 4-34 | ++ |
| 4-35 | ++ |
| 4-36 | ++ |
| 4-37 | ++ |
| 4-38 | ++ |
| 4-39 | ++ |
| 4-40 | ++ |
| 4-41 | ++ |
| 4-43 | ++ |
| 4-44 | ++ |
| 4-45 | ++ |
| 4-46 | ++ |
| 4-47 | ++ |
| 4-48 | ++ |
| 4-49 | + |
| 4-51 | + |
| 4-52 | +++ |
| 4-53 | +++ |
| 4-54 | +++ |
| 4-55 | + |
| 4-56 | + |
| 4-60 | +++ |
| 4-61 | + |

TABLE 20-continued

| Cpd. No. | Ki |
|---|---|
| 4-62 | + |
| 4-63 | + |
| 4-64 | + |
| 4-68 | +++ |
| 4-69 | ++ |
| 4-70 | ++ |
| 4-71 | +++ |
| 4-72 | +++ |
| 4-73 | +++ |
| 4-74 | ++ |
| 4-75 | ++ |
| 4-76 | +++ |
| 4-77 | +++ |
| 4-78 | ++ |
| 4-79 | +++ |
| 4-80 | +++ |
| 5-1 | +++ |
| 5-2 | + |
| 5-3 | + |
| 5-4 | ++ |
| 5-5 | +++ |
| 5-6 | ++ |
| 5-7 | ++ |
| 5-8 | +++ |
| 5-9 | + |
| 5-10 | + |
| 5-11 | + |
| 5-12 | + |
| 5-13 | ++ |
| 5-14 | +++ |
| 5-15 | ++ |
| 5-16 | ++ |
| 5-17 | +++ |
| 5-18 | +++ |
| 5-19 | ++ |
| 5-20 | +++ |
| 5-21 | + |
| 5-22 | +++ |
| 5-23 | +++ |
| 5-24 | +++ |
| 5-25 | + |
| 5-26 | + |
| 5-27 | +++ |
| 5-28 | +++ |
| 5-29 | +++ |
| 5-30 | +++ |
| 5-31 | +++ |
| 5-32 | +++ |
| 5-33 | ++ |
| 5-34 | + |
| 6-1 | +++ |
| 6-2 | + |
| 6-3 | +++ |
| 6-4 | +++ |
| 6-5 | ++ |
| 6-6 | ++ |
| 6-7 | ++ |
| 6-8 | ++ |
| 6-9 | ++ |
| 6-10 | ++ |
| 6-11 | ++ |
| 6-12 | ++ |
| 6-13 | ++ |
| 6-14 | ++ |
| 6-15 | ++ |
| 6-16 | ++ |
| 6-17 | ++ |
| 6-18 | ++ |
| 6-19 | + |
| 6-20 | + |
| 6-21 | + |
| 6-22 | + |
| 6-23 | + |
| 6-24 | + |
| 6-25 | + |
| 6-26 | +++ |
| 6-27 | +++ |
| 6-28 | + |
| 6-29 | + |
| 6-30 | + |
| 6-31 | + |
| 6-32 | ++ |
| 6-33 | + |
| 6-34 | + |
| 6-35 | +++ |
| 6-36 | +++ |
| 6-37 | +++ |
| 6-38 | ++ |
| 6-39 | + |
| 6-40 | +++ |
| 6-41 | ++ |
| 6-42 | +++ |
| 6-43 | ++ |
| 6-44 | + |
| 6-45 | + |
| 6-46 | +++ |
| 6-47 | +++ |
| 6-48 | +++ |
| 6-49 | + |
| 6-50 | +++ |
| 6-51 | ++ |
| 6-52 | ++ |
| 6-53 | ++ |
| 6-54 | ++ |
| 6-55 | ++ |
| 6-56 | ++ |
| 6-57 | ++ |
| 6-58 | + |
| 6-59 | ++ |
| 6-60 | ++ |
| 6-61 | + |
| 6-62 | + |
| 6-63 | + |
| 6-64 | + |
| 6-65 | ++ |
| 6-66 | + |
| 6-67 | ++ |
| 7-1 | +++ |
| 7-2 | ++ |
| 7-3 | ++ |
| 7-4 | ++ |
| 7-5 | + |
| 7-6 | + |
| 7-7 | + |
| 7-8 | + |
| 7-9 | +++ |
| 7-10 | +++ |
| 7-11 | +++ |
| 7-12 | +++ |
| 7-13 | + |
| 8-1 | +++ |
| 8-2 | ++ |
| 8-3 | ++ |
| 8-4 | ++ |
| 8-5 | + |
| 8-6 | + |
| 8-7 | + |
| 8-8 | ++ |
| 8-9 | ++ |
| 8-10 | ++ |
| 8-11 | ++ |
| 8-12 | ++ |
| 8-13 | ++ |
| 8-14 | ++ |
| 8-15 | ++ |
| 8-16 | ++ |
| 8-17 | ++ |
| 8-18 | ++ |
| 8-19 | ++ |
| 8-20 | + |
| 8-21 | + |
| 8-22 | + |
| 8-23 | + |
| 8-24 | + |
| 8-25 | + |
| 8-26 | + |

TABLE 20-continued

| Cpd. No. | Ki |
|---|---|
| 8-27 | + |
| 8-28 | + |
| 8-29 | + |
| 8-30 | + |
| 8-31 | + |
| 8-32 | + |
| 8-33 | + |
| 8-34 | + |
| 8-35 | + |
| 8-36 | + |
| 8-37 | + |
| 8-38 | + |
| 8-39 | + |
| 8-40 | + |
| 8-41 | + |
| 8-42 | + |
| 8-43 | + |
| 8-44 | + |
| 8-45 | + |
| 8-46 | + |
| 8-47 | + |
| 8-48 | +++ |
| 9-1 | +++ |
| 9-2 | + |
| 9-3 | + |
| 9-4 | + |
| 9-5 | +++ |
| 9-6 | +++ |
| 9-7 | +++ |
| 9-8 | +++ |
| 9-9 | +++ |
| 9-10 | +++ |
| 9-11 | ++ |
| 9-12 | ++ |
| 9-13 | ++ |
| 9-14 | ++ |
| 9-15 | ++ |
| 9-16 | ++ |
| 9-17 | ++ |
| 9-18 | + |
| 9-19 | + |
| 9-20 | + |
| 9-21 | ++ |
| 9-22 | ++ |
| 9-23 | ++ |
| 9-24 | ++ |
| 9-25 | ++ |
| 9-26 | ++ |
| 9-27 | ++ |
| 9-28 | ++ |
| 9-29 | ++ |
| 9-30 | ++ |
| 9-31 | ++ |
| 9-32 | ++ |
| 9-33 | ++ |
| 9-34 | + |
| 9-35 | + |
| 9-36 | + |
| 9-37 | + |
| 9-38 | + |
| 9-39 | ++ |
| 9-40 | ++ |
| 9-41 | ++ |
| 9-42 | + |
| 9-43 | + |
| 9-44 | ++ |
| 9-45 | ++ |
| 9-46 | ++ |
| 9-47 | + |
| 9-48 | + |
| 9-49 | + |
| 9-50 | + |
| 9-51 | + |
| 9-52 | + |
| 9-53 | + |
| 9-54 | + |
| 9-55 | + |
| 9-56 | + |

TABLE 20-continued

| Cpd. No. | Ki |
|---|---|
| 9-57 | + |
| 9-58 | + |
| 9-59 | + |
| 9-60 | + |
| 9-61 | + |
| 9-62 | +++ |
| 9-63 | +++ |
| 9-64 | +++ |
| 9-65 | + |
| 9-66 | + |
| 9-67 | + |
| 9-68 | + |
| 9-69 | + |
| 9-70 | +++ |
| 9-71 | +++ |
| 9-72 | +++ |
| 9-73 | +++ |
| 9-74 | + |
| 9-75 | + |
| 10-1 | ++ |
| 10-2 | + |
| 10-3 | + |
| 10-4 | + |
| 10-5 | +++ |
| 10-6 | +++ |
| 10-7 | +++ |
| 10-8 | +++ |
| 10-9 | +++ |
| 10-10 | +++ |
| 10-11 | +++ |
| 10-12 | +++ |
| 10-13 | +++ |
| 10-14 | +++ |
| 10-15 | + |
| 10-16 | + |
| 10-17 | + |
| 10-18 | +++ |
| 10-19 | +++ |
| 10-20 | +++ |
| 10-21 | +++ |
| 10-22 | +++ |
| 10-23 | +++ |
| 10-24 | ++ |
| 10-25 | ++ |
| 10-26 | + |
| 10-27 | + |
| 10-28 | + |
| 10-29 | ++ |
| 10-30 | ++ |
| 10-31 | ++ |
| 10-32 | ++ |
| 10-33 | ++ |
| 10-34 | ++ |
| 10-35 | ++ |
| 10-36 | ++ |
| 10-37 | ++ |
| 10-38 | ++ |
| 10-39 | ++ |
| 10-40 | ++ |
| 10-41 | ++ |
| 10-42 | +++ |
| 10-43 | +++ |
| 10-44 | +++ |
| 10-45 | ++ |
| 10-46 | ++ |
| 10-47 | ++ |
| 10-48 | + |
| 10-49 | + |
| 10-50 | + |
| 10-51 | + |
| 10-52 | + |
| 10-53 | + |
| 10-54 | +++ |
| 10-55 | ++ |
| 10-56 | +++ |
| 10-57 | +++ |
| 10-58 | +++ |
| 10-59 | + |

TABLE 20-continued

| Cpd. No. | Ki |
|---|---|
| 10-60 | + |
| 10-61 | + |
| 10-62 | + |
| 10-63 | + |
| 10-64 | + |
| 10-65 | + |
| 10-66 | + |
| 10-67 | + |
| 10-68 | + |
| 10-69 | + |
| 10-70 | + |
| 10-71 | + |
| 10-72 | + |
| 10-73 | + |
| 10-74 | + |
| 10-75 | + |
| 10-76 | ++ |
| 10-77 | ++ |
| 10-78 | ++ |
| 10-79 | +++ |
| 10-80 | +++ |
| 10-81 | +++ |
| 11-1 | ++ |
| 11-2 | ++ |
| 11-3 | ++ |
| 11-4 | + |
| 11-5 | + |
| 11-6 | ++ |
| 11-7 | ++ |
| 11-8 | + |
| 11-9 | + |
| 11-10 | + |
| 11-11 | + |
| 11-12 | + |
| 11-13 | + |
| 11-14 | + |
| 11-15 | + |
| 11-16 | + |
| 11-17 | + |
| 11-18 | + |
| 11-19 | + |
| 11-20 | + |
| 11-21 | + |
| 11-22 | + |
| 11-23 | + |
| 11-24 | + |
| 11-25 | + |
| 11-26 | + |
| 11-27 | + |
| 11-28 | + |
| 11-29 | + |
| 11-30 | + |
| 12-1 | ++ |
| 12-2 | + |
| 12-3 | + |
| 12-4 | ++ |
| 12-5 | + |
| 12-6 | + |
| 12-7 | + |
| 12-8 | + |
| 12-9 | + |
| 12-10 | + |
| 12-11 | ++ |
| 12-12 | ++ |
| 17-1 | +++ |
| 17-2 | + |
| 17-3 | +++ |
| 17-4 | ++ |
| 17-5 | +++ |
| 17-6 | +++ |
| 17-7 | + |
| 17-8 | ++ |
| 18-1 | +++ |
| 18-2 | + |
| 18-3 | + |
| 18-4 | +++ |
| 18-5 | +++ |
| 18-6 | ++ |

TABLE 20-continued

| Cpd. No. | Ki |
|---|---|
| 18-7 | ++ |
| 18-8 | ++ |
| 18-9 | ++ |
| 18-10 | ++ |
| 18-11 | ++ |
| 18-12 | ++ |
| 18-13 | ++ |
| 18-14 | ++ |
| 18-15 | + |
| 18-16 | +++ |
| 18-17 | +++ |
| 18-18 | + |
| 18-19 | + |
| 18-20 | ++ |
| 19-1 | + |
| 19-2 | ++ |
| 19-3 | + |
| 19-4 | + |
| 19-5 | + |
| 19-6 | + |
| 19-7 | + |
| 19-8 | + |
| 20-1 | ++ |
| 20-2 | +++ |
| 20-3 | +++ |
| 21-1 | ++ |
| 21-2 | +++ |
| 21-3 | + |
| 21-4 | ++ |
| 21-5 | + |
| 21-6 | + |
| 21-7 | +++ |
| 21-8 | + |
| 21-9 | + |
| 21-10 | + |
| 21-11 | + |
| 21-12 | + |
| 21-13 | ++ |
| 21-14 | +++ |
| 21-15 | +++ |
| 21-16 | +++ |
| 21-17 | +++ |
| 22-1 | ++ |
| 22-2 | +++ |
| 22-3 | +++ |
| 22-4 | +++ |
| 22-5 | +++ |
| 22-6 | ++ |
| 22-7 | +++ |
| 22-8 | +++ |
| 22-9 | +++ |
| 22-10 | +++ |
| 22-11 | ++ |
| 22-12 | +++ |
| 22-13 | +++ |
| 22-14 | +++ |
| 22-15 | +++ |
| 22-16 | ++ |
| 22-17 | +++ |
| 22-18 | ++ |
| 22-19 | ++ |
| 22-20 | NT |
| 22-21 | NT |
| 22-22 | +++ |
| 22-23 | +++ |
| 22-24 | +++ |
| 22-25 | +++ |
| 22-26 | ++ |
| 22-27 | ++ |
| 22-28 | ++ |
| 22-29 | ++ |
| 22-30 | +++ |
| 22-31 | +++ |
| 22-32 | +++ |
| 23-1 | + |
| 23-2 | ++ |
| 23-3 | ++ |
| 26-1 | +++ |

TABLE 20-continued

| Cpd. No. | Ki |
| --- | --- |
| 26-2 | +++ |
| 26-3 | + |
| 26-4 | +++ |
| 26-5 | +++ |
| 26-6 | +++ |
| 27-1 | ++ |
| 27-2 | + |
| 27-3 | + |
| 27-4 | + |
| 27-5 | + |
| 27-6 | + |
| 27-7 | + |
| 27-8 | + |
| 27-9 | + |
| 27-10 | + |
| 27-11 | ++ |
| 27-12 | ++ |
| 27-13 | + |
| 27-14 | + |
| 27-15 | + |
| 27-16 | + |
| 27-17 | + |
| 27-18 | + |
| 27-19 | + |

For the compounds of Table 20 above with Ki values against the M4 receptor of less than 10 nM (i.e., the "+++" compounds), their selectivity over the M1, M2, M3 and M5 receptors are set forth in Table 21 below. In Table 21, activity is expressed as follows: (1) "+++" means the compound had a Ki against the noted receptor of less than 10 nM; (2) "++" means the compound had a Ki against the noted receptor of less than 100 nM but greater than or equal to 10 nM; (3) "+" means the compound had a Ki against the noted receptor of less than 1 μM (1,000 nM) but greater or equal to 100 nM; and (4) "−" means the compound had a Ki against the noted receptor of 1 μM (1,000 nM) or greater or that activity was not detected against the noted receptor. ("NT" in Table 21 means that the compound was not tested agains the muscarinic receptor noted.)

TABLE 21

| Cpd No | M1 | M2 | M3 | M5 |
| --- | --- | --- | --- | --- |
| 3-1 | + | ++ | − | − |
| 3-5 | − | + | − | − |
| 3-8 | + | ++ | + | − |
| 3-9 | + | ++ | + | − |
| 3-10 | + | ++ | + | − |
| 3-11 | − | + | − | − |
| 3-12 | + | ++ | − | − |
| 3-13 | + | + | − | − |
| 3-14 | + | ++ | − | − |
| 3-16 | − | − | − | − |
| 3-17 | − | + | − | − |
| 3-18 | − | − | − | − |
| 3-19 | − | + | − | − |
| 3-21 | − | + | − | − |
| 3-22 | − | + | − | − |
| 3-23 | − | + | − | − |
| 4-1 | + | + | − | − |
| 4-5 | + | ++ | − | − |
| 4-6 | + | ++ | NT | − |
| 4-10 | + | ++ | + | + |
| 4-11 | + | ++ | − | − |
| 4-12 | + | ++ | + | − |
| 4-13 | − | + | − | − |
| 4-14 | − | + | NT | − |
| 4-15 | + | + | − | − |
| 4-16 | + | + | NT | − |
| 4-17 | − | + | − | − |
| 4-18 | − | + | − | − |
| 4-19 | + | + | − | − |
| 4-20 | + | ++ | − | − |
| 4-21 | + | ++ | + | − |
| 4-22 | − | + | − | + |
| 4-52 | + | ++ | + | − |
| 4-53 | + | ++ | + | + |
| 4-54 | + | + | − | − |
| 4-60 | + | ++ | + | + |
| 4-68 | + | + | − | − |
| 4-71 | + | + | − | − |
| 4-72 | + | + | NT | − |
| 4-73 | + | ++ | + | − |
| 4-76 | − | + | − | − |
| 4-77 | + | ++ | − | − |
| 4-79 | + | ++ | − | − |
| 4-80 | + | + | − | − |
| 5-1 | − | + | − | − |
| 5-5 | + | + | − | − |
| 5-8 | − | ++ | + | − |
| 5-14 | + | + | − | − |
| 5-17 | + | + | + | − |
| 5-18 | − | ++ | − | − |
| 5-20 | − | + | − | − |
| 5-22 | + | ++ | − | − |
| 5-23 | + | ++ | − | − |
| 5-24 | + | ++ | − | − |
| 5-27 | + | + | − | − |
| 5-28 | + | + | − | − |
| 5-29 | − | + | − | − |
| 5-30 | − | + | − | − |
| 5-31 | ++ | +++ | ++ | + |
| 5-32 | − | ++ | − | − |
| 6-1 | + | +++ | + | + |
| 6-3 | + | ++ | + | − |
| 6-4 | + | + | − | − |
| 6-26 | + | ++ | − | − |
| 6-27 | + | ++ | + | − |
| 6-35 | + | ++ | + | − |
| 6-36 | + | + | − | − |
| 6-37 | + | ++ | − | − |
| 6-40 | + | ++ | + | − |
| 6-42 | − | ++ | + | − |
| 6-46 | − | +++ | − | − |
| 6-47 | + | +++ | + | + |
| 6-48 | − | ++ | − | − |
| 6-50 | + | ++ | + | − |
| 7-1 | − | − | − | − |
| 7-9 | + | + | − | − |
| 7-10 | − | + | − | − |
| 7-11 | − | − | − | − |
| 7-12 | − | − | − | − |
| 8-1 | + | + | + | + |
| 8-48 | ++ | +++ | + | + |
| 9-1 | − | + | − | − |
| 9-5 | − | − | − | − |
| 9-6 | + | ++ | + | + |
| 9-7 | + | + | − | − |
| 9-8 | − | + | − | − |
| 9-9 | + | + | − | − |
| 9-10 | + | + | + | − |
| 9-62 | + | + | − | − |
| 9-63 | ++ | +++ | ++ | + |
| 9-64 | + | + | − | − |
| 9-70 | + | + | − | − |
| 9-71 | − | + | − | − |
| 9-72 | + | + | − | − |
| 9-73 | − | + | − | − |
| 10-5 | + | ++ | − | − |
| 10-6 | + | + | − | − |
| 10-7 | − | + | − | − |
| 10-8 | − | + | − | − |
| 10-9 | − | + | − | − |
| 10-10 | + | + | − | − |
| 10-11 | + | + | − | − |
| 10-12 | + | ++ | + | + |
| 10-13 | + | + | − | − |
| 10-14 | − | + | − | − |
| 10-18 | − | + | − | − |

TABLE 21-continued

| Cpd No | M1 | M2 | M3 | M5 |
|---|---|---|---|---|
| 10-19 | + | + | − | − |
| 10-20 | − | + | − | − |
| 10-21 | − | + | − | − |
| 10-22 | − | + | − | − |
| 10-23 | + | ++ | − | − |
| 10-42 | + | + | − | − |
| 10-43 | − | + | − | − |
| 10-44 | − | + | − | − |
| 10-54 | + | ++ | − | − |
| 10-56 | + | ++ | + | − |
| 10-57 | + | ++ | − | − |
| 10-58 | − | − | − | − |
| 10-79 | + | ++ | − | + |
| 10-80 | ++ | ++ | + | + |
| 10-81 | ++ | ++ | ++ | + |
| 17-1 | − | + | − | − |
| 17-3 | + | + | − | − |
| 17-5 | + | ++ | − | − |
| 17-6 | − | + | − | − |
| 18-1 | − | ++ | − | − |
| 18-4 | + | + | − | − |
| 18-5 | − | + | − | − |
| 18-16 | − | + | − | − |
| 18-17 | − | + | − | − |
| 20-2 | ++ | ++ | ++ | + |
| 20-3 | + | + | + | − |
| 21-2 | − | + | − | − |
| 21-7 | ++ | +++ | ++ | + |
| 21-14 | + | ++ | + | − |
| 21-15 | − | + | − | − |
| 21-16 | ++ | +++ | ++ | + |
| 21-17 | ++ | +++ | ++ | + |
| 22-2 | − | + | − | − |
| 22-3 | − | + | − | − |
| 22-4 | − | ++ | − | − |
| 22-5 | + | ++ | − | + |
| 22-7 | + | ++ | + | + |
| 22-8 | + | ++ | − | − |
| 22-9 | + | ++ | − | − |
| 22-10 | − | + | − | − |
| 22-12 | − | ++ | − | + |
| 22-13 | + | ++ | + | + |
| 22-14 | + | ++ | + | + |
| 22-15 | + | ++ | − | + |
| 22-17 | + | ++ | − | + |
| 22-22 | + | ++ | − | − |
| 22-23 | + | +++ | + | + |
| 22-24 | + | ++ | − | − |
| 22-25 | − | ++ | − | − |
| 22-30 | + | ++ | − | − |
| 22-31 | ++ | ++ | − | + |
| 22-32 | + | + | − | + |
| 26-1 | + | ++ | − | − |
| 26-2 | − | + | − | − |
| 26-4 | − | + | − | − |
| 26-6 | ++ | ++ | + | + |

Functional Assay

Functional antagonism of acetylcholine responses were evaluated using a $^{35}$S-GTPγS binding assay. Acetylcholine binding to the muscarinic receptors activates G-proteins. Activation of G-proteins can be determined by their binding of the radiolabeled GTP analogue $^{35}$S-GTPγS. In the assay, acetylcholine stimulates the binding of $^{35}$S-GTPγS to G-proteins associated with cell membranes, and the incorporated $^{35}$S-GTPγS can be collected by harvesting the membranes. Antagonist activity of the compounds was determined as the IC50 for inhibition of the acetylcholine response. The assay buffer used was 50 mM HEPES, 100 mM NaCl, 5 mM $MgCl_2$, 1 mM ethylenediaminetetraacetic acid, pH-adjusted to pH 7.4. Acetylcholine, compound (a dose-response of twelve concentrations ranging from 10 µM to 32 pM) and membranes from CHO cells expressing M4 or M2 receptors were incubated together in 150 µl buffer for 30 minutes at 30° C. in a 96-well plate. $^{35}$S-GTPγS was then added, to a final concentration of 0.2 nM and a final volume of 175 µl. Twenty minutes later, membranes were harvested by rapid vacuum filtration onto non-treated glass fiber filters, as previously described (see, e.g., Hoare et al., *Mol. Pharmacol.* 2003 63(3):751-65); Erratum at *Mol. Pharmacol.* 2005 July; 68(1): 260). The concentration of acetylcholine used was that which stimulated 80% of the maximal response (3 µM for the M4 receptor, 1 µM for M2). Many of the compounds described above have been evaluated in the functional assay.

Electrophysiology Assay

Adult (>8 weeks) female Lister hooded rats (Harlan, UK) were killed by decapitation and the brain was removed and placed into ice-cold oxygenated sucrose Krebs' medium containing (mM): sucrose 202, KCl 2, $KH_2PO_4$ 1.25, $MgSO_4$ 10, $CaCl_2$ 0.5, $NaHCO_3$ 26, glucose 10. The brain was hemisected along the midline and 300 µM parasagittal slices were prepared with an oscillating microtome (Integraslice; Campden Instruments Ltd., Loughborough, UK). Slices were then transferred to a recovery chamber at room temperature containing oxygenated Krebs' solution (mM): NaCl 124, KCl2, $KH_2PO_4$ 1.25, $MgSO_4$ 1, $CaCl_2$ 2, $NaHCO_3$ 26, glucose 10. Following at least 1 hour of recovery, individual slices were transferred to an interface recording chamber where they were perfused with Krebs' solution (33° C.). Extracellular field potential recordings were made with an Axoprobe 1A amplifier (Axon Instruments Ltd., USA) via a Krebs'-filled glass micropipette (resistance 2-5 MΩ) positioned in the stratum radiatum of the CAl, digitized (10 kHz) via a CED1401 interface and stored on a computer with Spike2 software (Cambridge Electronic Design Ltd., Cambridge, UK). Field excitatory postsynaptic potential (fEPSP) responses were evoked (pair of 0.02 ms pulses, separated by 40 ms; applied every 10s; adjusted to approximately 60% of the maximal spike-free response) by a bipolar stimulating electrode positioned in the stratum radiatum near the CA3-CA1 border.

The cholinergic agonist carbachol (aza-acetylcholine, resistant to degradation by acetylcholinesterase) was used to stimulate muscarinic receptors. The M1 muscarinic receptor was blocked using 5 µM VU0255035, a selective M1 antagonist. The resulting inhibitory signal was primarily M4-mediated, based on its sensitivity to the M4 activator VU010010. The effect of M4 antagonists on this M4-mediated inhibition of fEPSPs was measured by adding M4 compound 20 minutes prior to application of carbachol.

6-OHDA Surgical Lesion and Behavioral Testing Procedures

6-OHDA Lesion protocol: Male Sprague-Dawley rats were anesthetized with isoflurane and placed into the stereotaxic frame. Thirty minutes prior the injection of 6-OHDA, rats received desipramine (15 mg/kg, i.p.) to prevent the entry of the toxin into the noradrenergic cells. A unilateral lesion was induced by injections of 6-OHDA (8 µg/4 µl/site/rat; flow rate 1 µl/min; dissolved in 0.9% NaCl with 0.02% ascorbic acid) or vehicle into the left and right medial forebrain bundle at the following coordinates: AP−4.4. mm; L±1.2 mm; V−7.8 mm relative to Bregma (Paxinos and Watson, 2007). The rats were allowed to recover for 14 days and were then tested for locomotor activity induced by novelty (placing the rat in a new cage, 30 min) and for contraversive (contralateral) rotational behavior induced by apomorphine (0.2 mg/kg, s.c.).

Experimental animal selection criteria: Only the rats with activity higher than 5 turns/min following apomorphine treatment were enrolled in the study; rats not fulfilling the criteria were excluded from the study (typically 20%). Turning activity was then recorded for each group once per week for four consecutive weeks.

Locomotor Activity

Young adult male, Sprague-Dawley rats (240-250 g) were purchased from Charles River Laboratories and assessed in the Open Field (Kinder Scientific, CA) task during the light hours of a 12:12 L:D cycle and were tested under bright light conditions. Animals were allowed to acclimate to the facility for at least one week prior to use. On the day of testing, animals were acclimated to the test room for at least 1 hour and were then treated orally with the Neurocrine compound and placed into the test chamber 30 minutes later. Animals were allowed to freely ambulate for 60 minutes. Measurements taken included, but were not limited to, total horizontal and vertical beam breaks.

The various embodiments described above can be combined to provide further embodiments. All U.S. patents, U.S. patent application publications, U.S. patent applications, foreign patents, foreign patent applications, and non-patent publications referred to in this specification and/or listed in the Application Data Sheet are incorporated herein by reference in their entirety. Aspects of the embodiments can be modified, if necessary to employ concepts of the various patents, applications and publications to provide yet further embodiments.

The disclosures of U.S. provisional patent application Ser. No. 62/252,179, filed Nov. 6, 2015, and U.S. provisional patent application Ser. No. 62/275,708, filed Jun. 1, 2016, are incorporated herein by reference in their entirety.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled.

Accordingly, the claims are not limited by the disclosure.

We claim the following:

1. A compound having the structure of the following formula (VII):

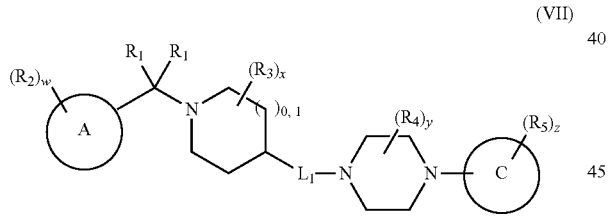

(VII)

or a stereoisomer, solvate, or pharmaceutically acceptable salt thereof, wherein:

A and C are each independently a carbocyclyl or heterocyclyl, $R_1$ is, at each occurrence, H, $C_{1-4}$alkyl, C(=O)O$C_{1-4}$alkyl or aryl;

$R_2$, $R_3$, $R_4$ and $R_5$ are each independently —OH, —NH$_2$, —NH($C_{1-4}$alkyl),—N($C_{1-4}$alkyl)$_2$, —C≡N, —C(=O)NH$_2$, halo, $C_{1-4}$alkyl, $C_{1-4}$alkyl—OH, $C_{1-4}$haloalkyl, $C_{1-4}$alkoxy, or $C_{1-4}$haloalkoxy; and w, x, y and z are each independently 0, 1, 2 or 3; and $L_1$ is selected from

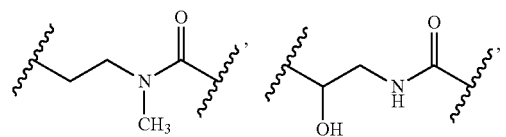

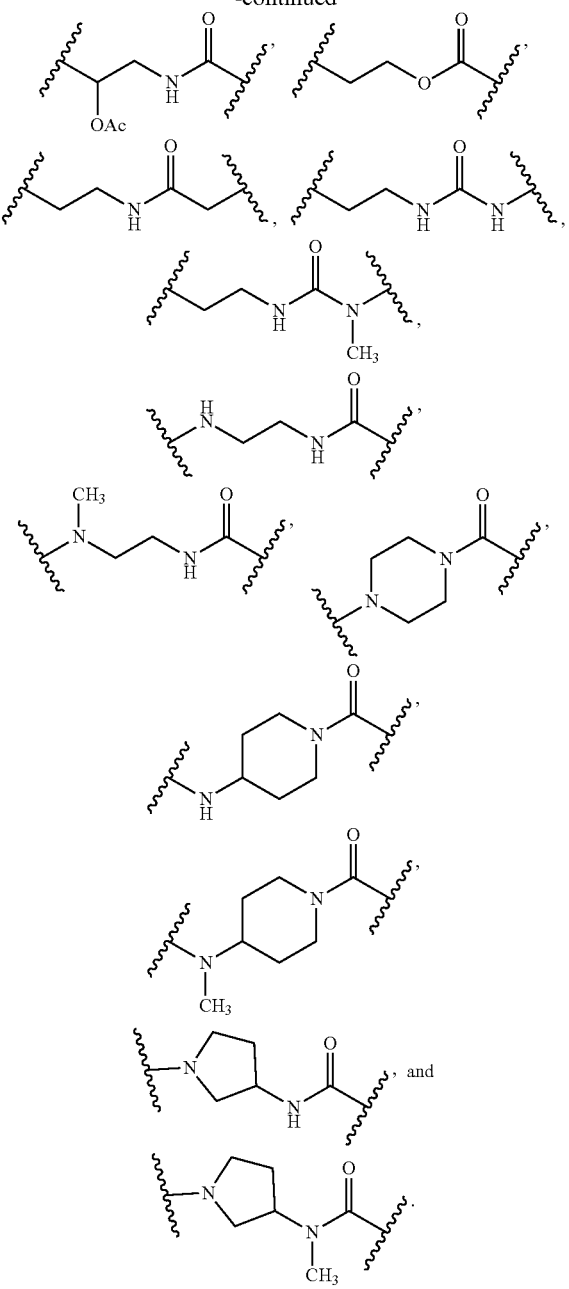

2. A compound having the structure of the following formula (VIII):

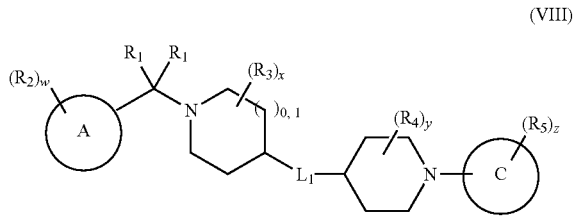

(VIII)

or a stereoisomer, solvate, or pharmaceutically acceptable salt thereof, wherein:

A and C are each independently a carbocyclyl or heterocyclyl;

$R_1$ is, at each occurrence, H, $C_{1-4}$alkyl, $C(=O)OC_{1-4}$alkyl or aryl;

$R_2$, $R_3$, $R_4$ and $R_5$ are each independently —OH, —NH$_2$, —NH($C_{1-4}$alkyl),—N($C_{1-4}$alkyl)$_2$, —C≡N, —C(=O)NH$_2$, halo, $C_{1-4}$alkyl, $C_{1-4}$alkyl—OH, $C_{1-4}$haloalkyl, $C_{1-4}$alkoxy, or $C_{1-4}$haloalkoxy; and w, x, y and z are each independently 0, 1, 2 or 3; and $L_1$ is selected from

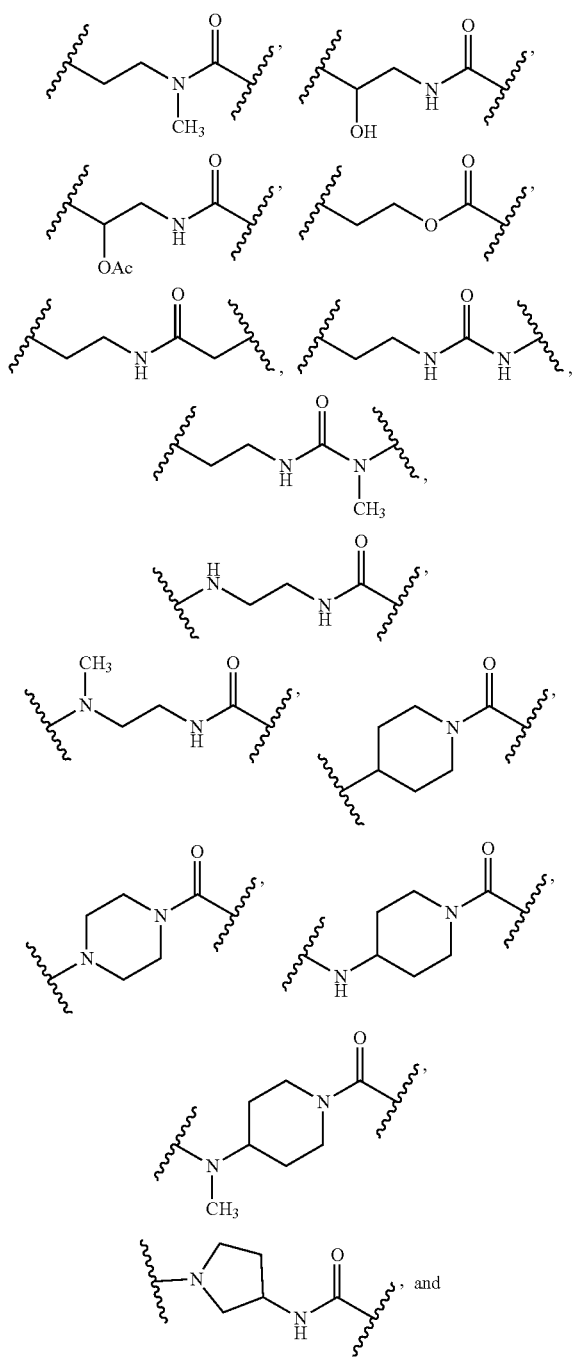

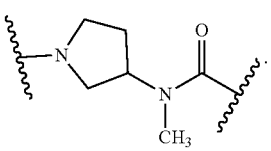

3. A compound having the structure of the following formula (IX):

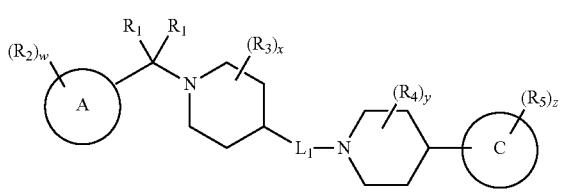

(IX)

or a stereoisomer, solvate, or pharmaceutically acceptable salt thereof, wherein:

A and C are each independently a carbocyclyl or heterocyclyl, $R_1$ is, at each occurrence, H, $C_{1-4}$alkyl, $C(=O)OC_{1-4}$alkyl or aryl;

$R_2$, $R_3$, $R_4$ and $R_5$ are each independently —OH, —NH$_2$, —NH($C_{1-4}$alkyl),—N($C_{1-4}$alkyl)$_2$, —C≡N, —C(=O)NH$_2$, halo, $C_{1-4}$alkyl, $C_{1-4}$alkyl—OH, $C_{1-4}$haloalkyl, $C_{1-4}$alkoxy, or $C_{1-4}$haloalkoxy; and w, x, y and z are each independently 0, 1, 2 or 3; and $L_1$ is selected from:

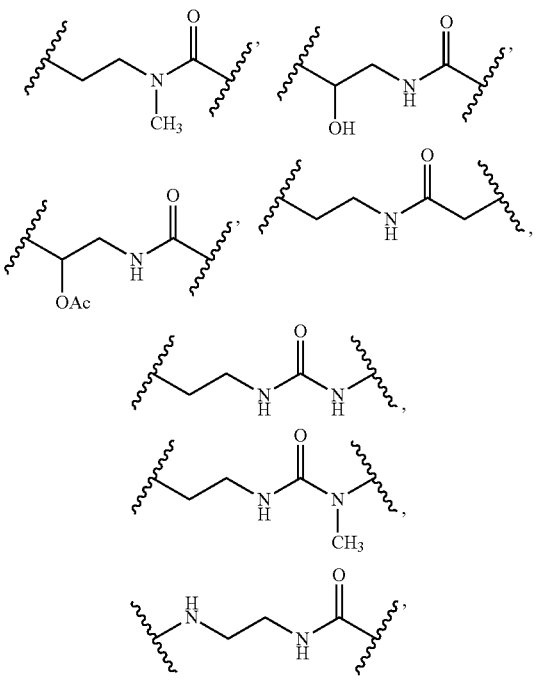

113

-continued

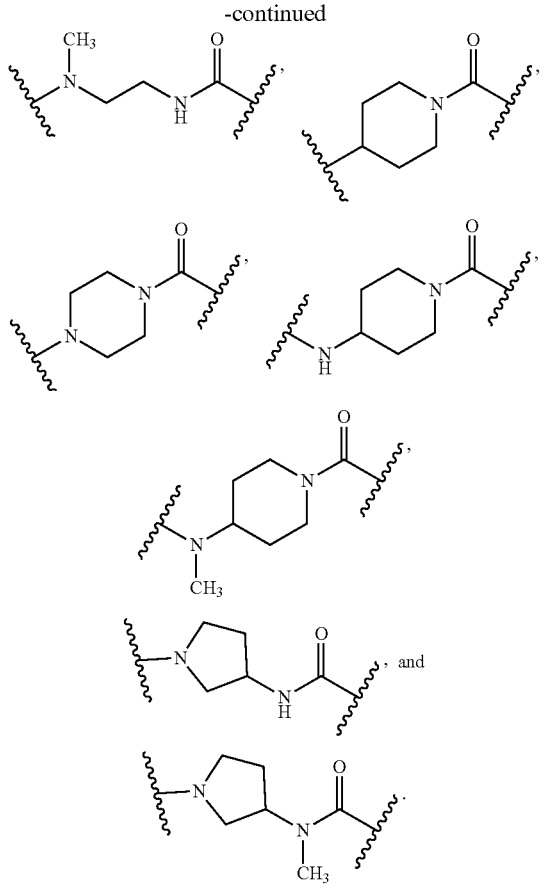

4. A compound having the structure of the following formula (XI):

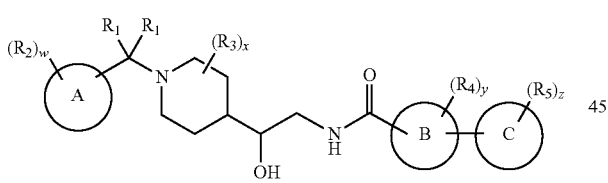

(XI)

or a stereoisomer, solvate, or pharmaceutically acceptable salt thereof, wherein:

A, B and C are each independently a carbocyclyl or heterocyclyl;

$R_1$ is, at each occurrence, H, $C_{1-4}$alkyl, C(=O)OC$_{1-4}$alkyl or aryl;

$R_2$, $R_3$, $R_4$ and $R_5$ are each independently —OH, —NH$_2$,—NH(C$_{1-4}$alkyl)$_2$, —C≡N, —C(=O)NH$_2$, halo, C$_{1-4}$alkyl, C$_{1-4}$alkyl— OH, C$_{1-4}$haloalkyl, C$_{1-4}$alkoxy, or C$_{1-4}$haloalkoxy; and w, x, y and z are each independently 0, 1, 2 or 3.

5. A compound having the structure of the following formula (XII):

114

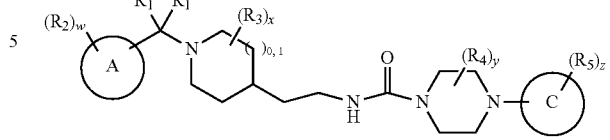

(XII)

or a stereoisomer, solvate, or pharmaceutically acceptable salt thereof, wherein:

A and C are each independently a carbocyclyl or heterocyclyl;

$R_1$ is, at each occurrence, H, c$_{1-4alkyl}$, C(=O)OC$_{1-4alkyl}$ or aryl;

$R_2$, $R_3$, $R_4$ and $R_5$ are each independently —OH, —NH$_2$, —NH(C$_{1-4}$alkyl), —N(C$_{1-4}$alkyl)$_2$, —C≡N, —C(=O)NH$_2$, halo, C$_{1-4}$alkyl, C$_{1-4}$alkyl—OH, C$_{1-4}$haloalkyl, C$_{1-4}$alkoxy or C$_{1-4}$haloalkoxy; and w, x, y and z are each independently 0, 1, 2 or 3.

6. A compound having the structure of the following formula (XIII):

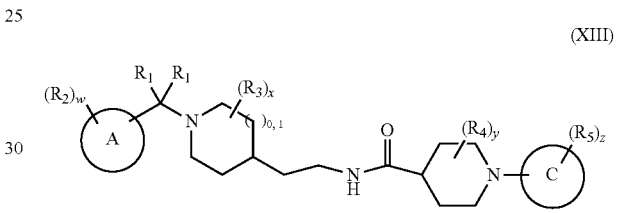

(XIII)

or a stereoisomer, solvate, or pharmaceutically acceptable salt thereof, wherein:

A and C are each independently a carbocyclyl or heterocyclyl;

$R_1$ is, at each occurrence, H, C$_{1-4}$alkyl, C(=O)OC$_{1-4}$alkyl or aryl;

$R_2$, $R_3$, $R_4$ and $R_5$ are each independently —OH, —NH$_2$, —NH(C$_{1-4}$alkyl)$_2$, —N(C$_{1-4}$alkyl)$_2$, —C≡N, —C(=O)NH$_2$, halo, C$_{1-4}$alkyl, C$_{1-4}$alkyl— OH, C$_{1-4}$haloalkyl, C$_{1-4}$alkoxy or C$_{1-4}$haloalkoxy; and w, x, y and z are each independently 0, 1, 2, 3, wherein at least one of y or z is 1, 2, or 3.

7. A compound having the structure of the following formula (XIV):

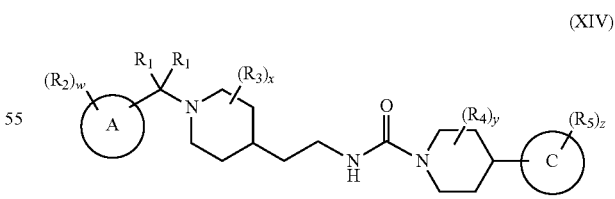

(XIV)

or a stereoisomer, solvate, or pharmaceutically acceptable salt thereof, wherein:

A and C are each independently a carbocyclyl or heterocyclyl;

$R_1$ is, at each occurrence, C$_{1-4}$alkyl,C(=O)OC$_{1-4}$alkyl or aryl;

$R_2$, $R_3$, $R_4$ and $R_5$ are each independently —OH, —NH$_2$, —NH(C$_{1-4}$alkyl), —N(C$_{1-4}$alkyl)$_2$ —C≡N, —C(=O)NH₂, halo, $C_{1-4}$alkyl, $C_{1-4}$alkyl—OH, $C_{1-4}$haloalkyl, $C_{1-4}$alkoxy, or $C_{1-4}$haloalkoxy; and w, x, y and z are each independently 0, 1, 2 or 3, wherein at least one of y or z is 1, 2 or 3.

8. A pharmaceutical composition comprising a compound of any one of claims 1-7, or a stereoisomer, solvate or pharmaceutically acceptable salt thereof, and at least one pharmaceutically acceptable excipient.

9. A method for antagonizing a muscarinic receptor of a cell comprising contacting the cell with a compound of any one of claims 1-7, or a stereoisomer, solvate or pharmaceutically acceptable salt thereof.

10. A method for treating or a neurological disease or disorder in a subject in need thereof, comprising administering to the subject a therapeutically effective amount of a compound of any one of claims 1-7, or a stereoisomer, solvate or pharmaceutically acceptable salt thereof, wherein the neurological disease or disorder is selected from the group consisting of Alzheimer's Disease, Lewy body dementia, a cognitive deficit associated with schizophrenia, Parkinson's disease. drug induced Parkinsonism, dyskinesia, dystonia, chorea, cerebral palsy, progressive supranuclear palsy, and Huntinoton's disease.

11. The method of claim 10, wherein the.

12. A compound, which is:

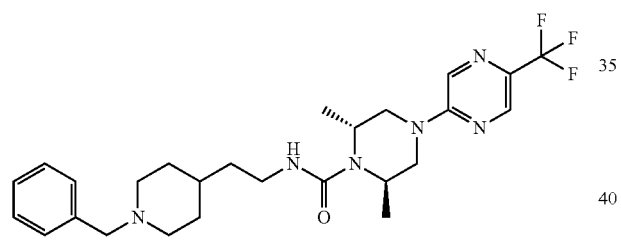

(2R, 6R)-N-[2-(1-benzylpiperidin-4-yl)ethyl]-2,6-dimethyl-4-[5-(trifluoromethyl)pyrazin-2-yl]piperazine-1-carboxamide, or a solvate or pharmaceutically acceptable salt thereof.

13. A compound, which is:

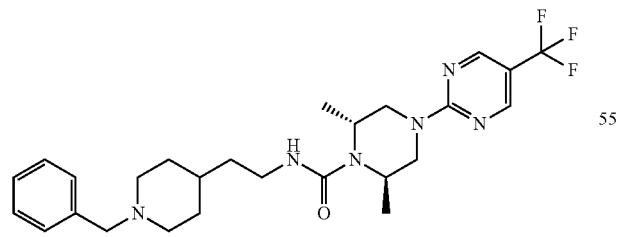

(2R,6R)-N-[2-(1-benzylpiperidin-4-yl)ethyl]-2,6-dimethyl-4-[5-(trifluoromethyl)pyrimidin-2-yl]piperazine-1-carboxamide, or a solvate or pharmaceutically acceptable salt thereof.

14. A compound, which is:

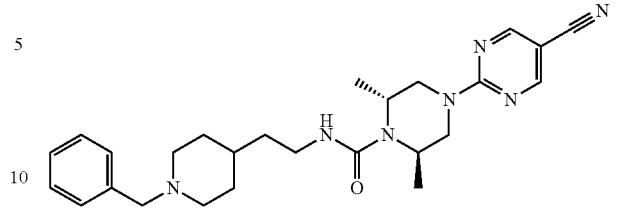

(2R,6R)-N-(2-4-benzylpiperidin-4-yl)ethyl)-4-(5-cyanopyrimidin-2-yl)-2,6-dimethylpiperazine-1-carboxamide, or a solvate or pharmaceutically acceptable salt thereof.

15. A compound, which is:

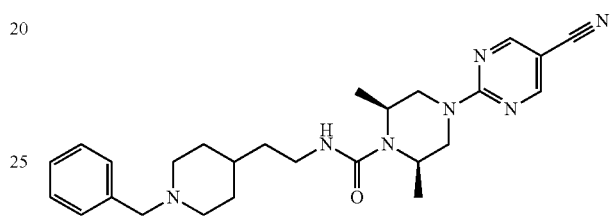

(2S,6R)-N-(2-(1-benzylpiperidin-4-yl)ethyl)-4-(5-cyanopyrimidin-2-yl)-2,6-dimethylpiperazine- 1-carboxamide, or a solvate or pharmaceutically acceptable salt thereof.

16. A compound, which is:

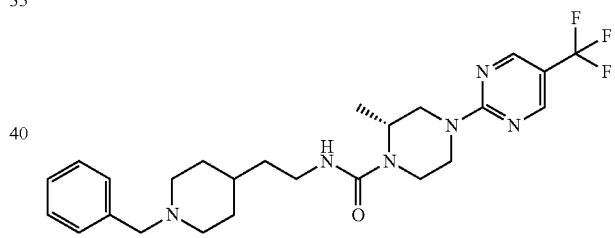

(2R)-N[2-(1-benzylpiperidin-4-yl)ethyl]-2,6-dimethyl-4-]5-(trifluoromethyl)pyrazin-2-yl]-1-carboxamide, or a solvate or pharmaceutically acceptable salt thereof.

17. A compound, which is:

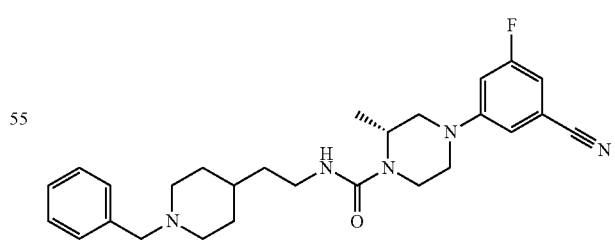

(2R)-N-[2-1-benzylpiperidin-4-yl)ethyl]-4-(3-cyano-5fluorophenyl)-2-methylpiperazine-carboxamide, or a solvate or pharmaceutically acceptable salt thereof.

* * * * *